United States Patent [19]
Chance et al.

[11] Patent Number: 5,514,646
[45] Date of Patent: May 7, 1996

[54] INSULIN ANALOGS MODIFIED AT POSITION 29 OF THE B CHAIN

[76] Inventors: Ronald E. Chance, 19303 Flippin Rd., Westfield, Ind. 46074; Richard D. DiMarchi, 3815 Wolf Creek Cir., Carmel, Ind. 46032; Bruce H. Frank, 8025 Claridge Rd., Indianapolis, Ind. 46260; James E. Shields, 17808 Grassy Branch Rd., Noblesville, Ind. 46060

[21] Appl. No.: 57,201

[22] Filed: May 5, 1993

Related U.S. Application Data

[63] Continuation of Ser. No. 686,632, Apr. 17, 1991, abandoned, which is a continuation-in-part of Ser. No. 388,201, Aug. 4, 1989, abandoned, which is a continuation-in-part of Ser. No. 308,352, Feb. 9, 1989, abandoned.

[51] Int. Cl.$^6$ .............................. C07K 7/40; D61K 37/26
[52] U.S. Cl. ........................... 514/3; 435/68.1; 435/69.4; 530/303; 514/4
[58] Field of Search ........................ 514/3, 4; 405/68.1, 405/69.4; 530/303

[56] References Cited

U.S. PATENT DOCUMENTS

| | | |
|---|---|---|
| 4,639,333 | 1/1987 | Obermeier et al. |
| 4,946,828 | 8/1990 | Markussen et al. .................. 514/3 |
| 5,126,249 | 6/1992 | Becker et al. ..................... 435/68.1 |
| 5,164,366 | 11/1992 | Balschmidt et al. ................ 514/3 |

FOREIGN PATENT DOCUMENTS

| | | |
|---|---|---|
| 055945 | 12/1981 | European Pat. Off. . |
| 214826 | 3/1987 | European Pat. Off. . |
| 254516 | 1/1988 | European Pat. Off. . |
| 280534 | 8/1988 | European Pat. Off. . |
| 375437 | 6/1990 | European Pat. Off. . |
| WO90/07522 | 7/1990 | WIPO . |

OTHER PUBLICATIONS

Randle, P. J., Assay of Plasm Insulin Activity by the Rat-Diaphragm Method, *Brit. Med. J.* 1:1237 (1954).
Steinke, J. et al., Assay of Crystalline Insulin and of Serum Insulin-Like Activity of Different Species on Adipose Tissue of the Rat, Mouse and Guinea Pig, *N.E.J. Med.* 273:1464 (1965).
Sheps, M. C. et al., Measurement of Small Quantities of Insulin-Like Activity Using Rat Adipose Tissue. II. Evaluation of Performance, *J. Clin. Investigation* 39:1499 (1960).
Burke, G. T. et al., Superactive Insulins, *Biochem. Biophys. Res. Comm.* 173:982 (1990).
Brange, J. et al., Monomeric Insulins and Their Experimental and Clinical Implications, *Diabetes Care* 13:923 (1990).
Bruce H. Frank, Text and Slide Copies of Lecture given at the Conference on Insulin, Self Association and Conformational Studies on Human Proinsulin and Insulin Analogs, University of York, Aug. 29–Sep. 1, 1989.
J. Brange, et al., Monomeric Insulins Obtained by Protein Engineering and their Medical Implications, *Nature*, 333:679 (1988).
J. Brange, et al., 65. Insulin Analogues with Reduced Association Tendency: Biological Acitvity and Absorption Rate After Subcutaneous Administration, *Abstracts*, 503A.
Rinderknecht E. et al., The Amino Acid Sequence of Human Insulin-like Growth Factor I and Its Structural Homology with Proinsulin, 253:8, 2769–2776 (1978).
Brange J. et al., Monomeric Insulins by Protein Engineering, *Protein Engineering*, 1:3, 238, Abstract No. 3.
Brange J. et al., Insulin Analogues with Reduced Association Tendency: Biological Activity and Absorption Rate After Subcutaneous Administration, *PostGrad. Med. J.*, 64:3, 18 (1988).

*Primary Examiner*—Howard E. Schain

[57] ABSTRACT

Analogs of human insulin modified at position 29 of the B chain thereof and, optionally, at other positions, have modified physico-chemical and pharmacokinetic properties and are useful in the treatment of hyperglycemia.

81 Claims, 20 Drawing Sheets

Figure 15

```
      HindIII  NdeI                                          DraIII
5'    |AGCTTCAT|ATGTATTTTGTTAACCAACACCTGTGCGGCTCCCACCTG|GTGGAAGCTCT
             AGTA TACATAAAACAATTGGTTGTGGACACGCCGAGGGTGGAC CACCTTCGAGA GTACCTGGTGTGCGGTGAACGTGGCTTCTTCTACACCCCGAAGACCCGCCGTGAGGCA
      CATGGACCACACGCCACTTGCACCGAAGAAGATGTGGGGCTTCTGGGCGGCACTCCGT
         AvaII                              XmaI
      GAG|GACCTGCAGGTGGGTCAGGTGGAGCTGGGCGGTGGC|CCGGGTGCAGGCAGCCTGC
      CTC CTGGACGTCCACCCAGTCCACCTCGACCCGCCACCG GGCCCACGTCCGTCGGACG AGCCGCTGGCCCTGGAGGGTTCCCTGCAGAAGCGTGGCATTGTGGAACAATGCTGTAC
      TCGGCGACCGGGACCTCCCAAGGGACGTCTTCGCACCGTAACACCTTGTTACGACATG
                                                BamHI
      CAGCATCTGCTCCCTGTACCAGCTGGAGAACTACTGCAACTAG|GATCCG        3'
      GTCGTAGACGAGGGACATGGTCGACCTCTTGATGACGTTGATC CTAGGCTTAA|   5'
                                                         EcoRI
```

INSULIN ANALOGS MODIFIED AT POSITION 29 OF THE B CHAIN

CROSS-REFERENCE

This application is a continuation of application Ser. No. 07/686,632, filed of Apr. 17, 1991, now abandoned, which is a continuation-in-part of application Ser. No. 07/388,201, filed Aug. 4, 1989, now abandoned, which is a continuation-in-part of application Ser. No. 07/308,352 filed Feb. 9, 1989 now abandoned.

BACKGROUND OF THE INVENTION

The present invention relates to analogs of insulin modified at amino acid position 29 of the native human insulin B chain and optionally at other positions. Said insulin analogs are less prone to dimerization or self-association to higher molecular weight forms thereby possessing a comparatively more rapid onset of activity while retaining the biological activity of native human insulin.

SUMMARY OF THE INVENTION

The present invention provides insulin analogs of the formula

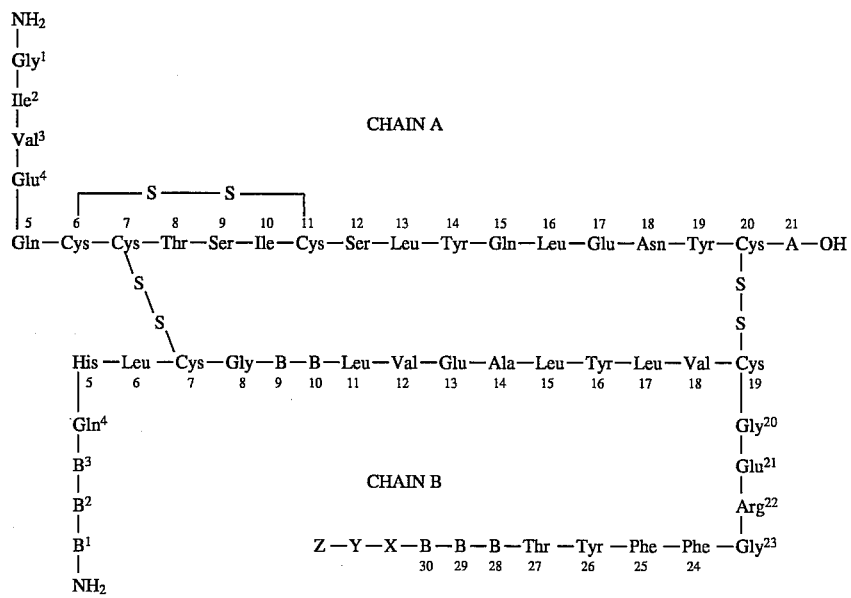

(I)

wherein A21 is alanine, asparagine, aspartic acid, glutamine, glutamic acid, glycine, threonine, or serine; B1 is phenylalanine, aspartic acid, or is absent; B2 is valine or may be absent when B1 is absent; B3 is asparagine or aspartic acid; B9 is serine or aspartic acid; B10 is histidine or aspartic acid; B28 is any amino acid, B29 is L-proline, D-proline, D-hydroxyproline, or L-hydroxyproline; B30 is alanine, threonine or is absent; Z is —OH, —NH$_2$, —OCH$_3$, or —OCH$_2$CH$_3$; X is Arg, Arg-Arg, Lys, Lys-Lys, Arg-Lys, Lys-Arg, or is absent; and Y may be present only when X is present and, if present, is Glu or an amino acid sequence which comprises all or a portion of the sequence -Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg- and which begins at the N-terminus Glu of such sequence.

Also disclosed and claimed is a method of treating hyperglycemia by administering to a patient in need thereof an effective amount of an insulin analog of formula I. Further, pharmaceutical compositions containing an effective amount of an insulin analog of formula I in combination with one or more pharmaceutically acceptable excipients are disclosed and claimed.

BRIEF DESCRIPTION OF THE DRAWINGS

The figures provided herein are not drawn exactly to scale.

FIG. 15—The nucleotide sequence of the synthetic human proinsulin gene.

DETAILED DESCRIPTION OF THE INVENTION

Figure 1:
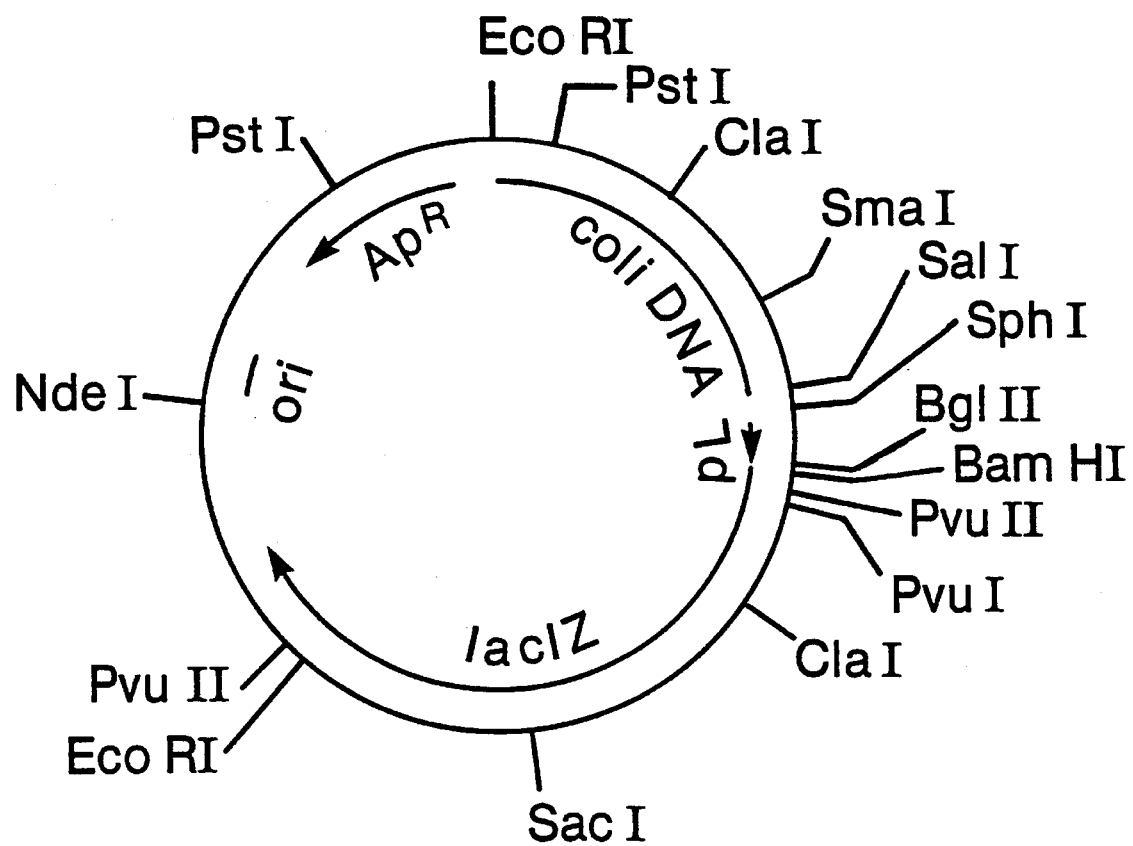
FIG. 1—A restriction site and function map of plasmid pKC283.

Formula I is a short-hand representation of the amino acid sequence of the insulin analogs of the present invention. The amino acid abbreviations have the following conventional meanings:

| Abbreviation | Amino Acid |
| --- | --- |
| Aba | α-Aminobutyric acid |
| Ala | Alanine |
| Arg | Arginine |
| Asn | Asparagine |
| Asp | Aspartic acid |
| Cya | Cysteic acid |
| Cys | Cysteine |
| Gln | Glutamine |
| Glu | Glutamic acid |
| Gly | Glycine |
| His | Histidine |
| Ile | Isoleucine |
| Leu | Leucine |
| Lys | Lysine |
| Met | Methionine |
| Nle | Norleucine |
| Nva | Norvaline |
| Orn | Ornithine |
| Phe | Phenylalanine |
| Pro | Proline |
| Ser | Serine |
| Thr | Threonine |
| Trp | Tryptophan |
| Tyr | Tyrosine |
| Val | Valine |

B28 may be any natural or non-naturally occurring amino acid. Preferably, said amino acid is aspartic acid, valine, leucine, isoleucine, norleucine, proline, arginine, histidine, citrulline, ornithine, lysine, phenylalanine, alanine or glycine. Of the above amino acids, a particularly preferred subgroup thereof is aspartic acid, valine, leucine, isoleucine, norleucine, proline, arginine, histidine, ornithine or lysine. Lysine is the most particularly preferred amino acid at B28. B29 preferably is L-proline, D-proline, D-hydroxyproline or L-hydroxyproline. A particularly preferred insulin analog of the present invention is one wherein B28 is lysine and B29 is proline, i.e., an inversion of the native human insulin amino acid sequence at positions 28 and 29 of the B-chain.

Further modifications of the insulin analogs of the present invention are also contemplated hereunder, i.e., modifications to the insulin analogs at positions other than at positions B28 and B29. Specifically, it may be desirable to optionally substitute the Asn residue from position 21 of the A chain (i.e., the carboxy terminus) with Ala, Asp, Gln, Glu, Gly, Thr or Ser, and, if so substituted, preferably with Ala. Similarly, it may be desirable to substitute the Asn residue at position 3 of the B-chain with aspartic acid (Asp). Such optional substitutions have the effect of increasing the stability of the analogs at pH extremes since Asn is particularly sensitive to deamidation and rearrangement reactions at both low and high pH. The skilled artisan will also readily appreciate that the glutamine residues of the insulin analogs may similarly be sensitive to deamidation and rearrangement. Accordingly, the substitution therefor by glutamic acid is also within the scope of the present invention. Additional, optional modifications to the insulin analogs of the present invention include (in any combination) replacement of the histidine residue at position B10 with the amino acid aspartic acid; replacement of the phenylalanine residue at position B1 with aspartic acid; replacement of the threonine residue at position B30 with alanine; replacement of the serine residue at position B9 with aspartic acid; deletion of amino acids at position B1 (des-B1) alone or in combination with a deletion at position B2 (des-B2); and deletion of threonine from position B-30 (des-B30).

The insulin analogs of this invention may also be modified at the B30 terminus by addition of any of the following amino acids or dipeptides: Arg, Arg-Arg, Lys, Lys-Lys, Arg-Lys, or Lys-Arg. These, when present, are designated in Formula I by the group X. Preferably, when such an extension is present, it is Arg-Arg.

In addition, should the foregoing extension at B30 be present, the analog may be further modified by addition at the resulting B30-lengthened terminus of glutamic acid (Glu) or of an amino acid sequence comprising all or a portion of the sequence -Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-, which sequence begins at its N-terminus Glu. This amino acid or sequence, when present, is designated in Formula I by the group Y. When the sequence represents only a portion of the foregoing, it will be any of those portions which begin at the N-terminus of the sequence, i.e., at the glutamic acid (Glu) residue.

In the foregoing, X or the combination of X and Y represents all or a portion of the connecting peptide found in human proinsulin, a molecule which is the biological precursor in the formation of native human insulin.

Preferred sequences for Y are:
-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-;
-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-;
-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-;
-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-;
-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-;
and
-Glu-Ala-Glu-Asp-Leu-Gln-Val-Gly-Gln-Val-Glu-.

In addition, whether X alone or X and Y together are present or absent, the terminus group Z may be any of the following: —OH, —NH$_2$, —OCH$_3$, or —OCH$_2$CH$_3$. Preferably, Z is —OH.

As mentioned hereinabove, the invention includes pharmaceutically acceptable salts of the insulin analogs. Preferred such salts are those of zinc, sodium, potassium, magnesium, calcium, or combinations of these salts.

The insulin analogs of this invention can be prepared by any of a variety of recognized peptide synthesis techniques including classical (solution) methods, solid-phase methods, semisynthetic methods and the more recently available recombinant DNA methods.

In the solid-phase technique, the amino acid sequence is constructed sequentially from an initial, insoluble, resin-supported C-terminal amino acid. Techniques for the solid phase method are described by J. Stewart et al., *Solid-Phase Peptide Synthesis*, Freeman and Co., San Francisco, 1969.

In general, in the solid-phase method, the amino acid corresponding to the C-terminal amino acid residue of the desired peptide is anchored to an insoluble resin support, and the peptide chain then is formed beginning at the resin-supported C-terminal amino acid. Individual amino acids are introduced sequentially until the desired amino acid sequence is obtained. Alternatively, small peptide fragments can be prepared and introduced into the peptide chain in the desired order. The peptide chain remains attached to the resin throughout synthesis, and, upon completion of the chain, the peptide is cleaved from the resin.

The peptide chain is attached to the polystyrene resin by means of an ester linkage formed between the carboxyl group of the C-terminal moiety and a specific methylene group present on the resin matrix as a site for such attachment.

The amino acids are coupled using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, or isobutyl chloroformate. Alternatively, the amino acid can be converted to an active ester such as a 2,4,5-trichlorophenyl ester, a pentachlorophenyl ester, a p-nitrophenyl ester, a N-hydroxysuccinimide ester, or an ester formed from 1-hydroxybenzotriazole, Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. See Schroder and Lubke, *The Peptides*, Academic Press, 1965, Chapter III which is incorporated herein by reference.

It should be recognized that the $\alpha$-amino group of each amino acid employed in the peptide synthesis must be protected during the coupling reaction to prevent side reactions involving the reactive $\alpha$-amino function. It should also be recognized that certain amino acids contain reactive side-chain functional groups (e.g., sulfhydryl, $\epsilon$-amino, $\beta$-and $\alpha$-carboxyl, imidazole, guanido and hydroxyl), and that such functional groups must also be protected both during the initial and subsequent coupling steps. Suitable protecting groups are known in the art. See for example, *Protective Groups In Organic Chemistry*, M. McOmie, Editor, Plenum Press, N.Y., 1973 and U.S. Pat. No. 4,617,149 which is incorporated herein by reference.

In selecting a particular protecting group, certain conditions must be observed. An $\alpha$-amino protecting group (1) must render the $\alpha$-amino function inert under the conditions employed in the coupling reaction, (2) must be readily removable after the coupling reaction under conditions that will not remove side chain protecting groups and will not alter the structure of the peptide fragment, and (3) must eliminate the possibility of racemization upon activation immediately prior to coupling. A side chain protecting group (1) must render the side chain functional group inert under the conditions employed in the coupling reaction, (2) must be stable under the conditions employed in removing the $\alpha$-amino protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity to the agents employed for their removal. For example, certain protecting groups, such as triphenyl methyl and 2-(p-biphenylyl)isopropyloxycarbonyl are very labile and can be cleaved under mild acid conditions. Other protecting groups, such as t-butyloxycarbonyl, t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl, halobenzyloxycarbonyl, p-nitrobenzyloxycarbonyl, cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid anhydrous hydrogen fluoride. This reagent not only will cleave the peptide from the resin but will also remove all protecting groups. Hence, use of this reagent will directly afford the fully deprotected peptide. When it is desired to cleave the peptide without removing protecting groups, the protected peptide-resin can undergo methanolysis to give the protected peptide in which the C-terminal carboxyl group is methylated. The methyl ester can then be hydrolyzed under mild, alkaline conditions to give the free C-terminal carboxyl. The protecting groups on the peptide chain then can be removed by treatment with a strong acid, such as liquid hydrogen fluoride. A particularly useful technique for methanolysis is that of G. Moore et al., *Peptides*, Proc. 5th Amer. Pept. Symp., M. Goodman and J. Meienhofer, Eds., John Wiley, N.Y., 1977, pp. 518–521, in which the protected peptideresin is treated with methanol and potassium cyanide in the presence of crown ether.

Another method for cleaving the protected peptide from the resin is by ammonolysis or by treatment with hydrazine. If desired, the resulting C-terminal amide or hydrazide can be hydrolyzed to the free C-terminal carboxyl, and the protecting groups can be removed conventionally.

It will also be recognized that the protecting group present on the N-terminal $\alpha$-amino group may be removed preferentially either before or simultaneously with the cleavage of the protected peptide from the resin support.

The A and B chains of the insulin analogs of the present invention can also be prepared via recombinant DNA methodology. In their preparation, a nucleotide sequence coding for the desired peptide of the A or B chain is prepared using now-routine techniques for such synthesis. These methods generally involve preparation of oligonucleotides coding both for fragments of the desired coding sequence and for the complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the peptide product for which it codes to be expressed. A suitable cloning vector contains at least a portion of a gene's expression control sequence.

The A and B chains of the insulin analogs of the present invention may also be prepared via a proinsulin-like precursor molecule using recombinant DNA techniques. See Frank et al., *Peptides: Synthesis-Structure-Function*, Proc. Seventh Am. Pept. Symp., Eds. D. Rich and E. Gross (1981) which is incorporated herein by reference.

The step of combining the individual A and B chains, however produced, may be achieved by the method of Chance et al., *Peptides:Synthesis, Structure and Function:Proc. of Seventh American Peptide Symposium* (1981) which is incorporated herein by reference.

The following examples are provided as a means of illustrating the present invention and are not to be construed as a limitation thereon.

EXAMPLE 1

Lys(B28), Pro(B29) Human Insulin

A. Preparation of Recombinant-Derived A Chain

Human insulin A-chain was prepared via recombinant DNA technology from the chemical synthesis of the gene encoding the A-chain and the expression thereof in *E. coli*. Briefly, the gene for the A-chain was synthesized from various trinucleotides into synthetic fragments, deca-to pentadecanucleotides in length, by a block phosphotriester method. The gene had single-stranded cohesive termini for the Eco RI and Bam HI restriction endonucleases. Insertion thereof into an appropriate expression vector containing the β-galactosidase gene (β-gal) rendered a chimeric plasmid having the A-chain linked to the β-gal gene via a methionine codon. Preferably, the tryptophan synthetase gene (trp LE') is used as a promoter rather than the β-gal gene to achieve higher levels of expression. The chimeric plasmid was transformed into *E. coli* resulting in the expression of a precursor protein, i.e., β-gal-met-A-chain (or trp LE'-met-A-chain when the trp LE' promoter system is used). Treatment of the precursor protein with cyanogen bromide cleaved the methionine bond to render, after purification, the human insulin A-chain. Oxidative sulfitolysis rendered the S-sulfonated A-chain which was utilized for combination with the B-chain (S-sulfonate) as described, infra.

For complete details on the chemical synthesis of the genes for the human insulin A-chain see Crea et al., *Proc. Natl. Acad. Sci. USA*, 75, 5765–5769, 1978 and references cited therein which are incorporated herein by reference. For complete details of the expression in *E. coli* of the chemically synthesized gene for the human insulin A-chain see Goeddel et al., *Proc. Natl. Acad. Sci. USA*, 76, 101–110, 1979 and references cited therein which are incorporated herein by reference.

B. Preparation of B Chain Analog [Lys(B28), Pro(B29)]

An Applied Biosystems 430A peptide synthesizer (including software revision 1.4) was used to prepare a crude peptidyl resin. 0.5 millimoles (mMol) of the starting solid phase resin (t-BOC-Thr(Bzl)OCH$_2$ Pam resin) was used (0.76 mMol/g×658 g). All amino acids used were BOC protected and, except for glutamic acid and histidine, all were used directly as received (i.e., in cartridges from Applied Biosystems, Inc., each cartridge contained approximately 2 mmol of protected amino acid). Glutamic acid and histidine were obtained from Peptides International Corporation and transferred to cartridges such that each cartridge contained approximately 2 mMol of the desired protected amino acid. After drying of the crude peptidyl resin (under vacuum at room temperature overnight) its weight was determined and compared to the starting weight to assure reasonable weight gain. A small portion of sample was submitted for amino acid analysis to ensure that the desired amino acids were added in the correct amounts.

The peptide was cleaved from the peptidyl resin and side-chain deprotected by stirring for approximately 1 hour at 0° C. in a solution of 10 parts (v/w) HF (containing 5% v/v ethyl mercaptan and 5% v/v m-cresol) to 1 part peptidyl resin. After removal of most of the HF by vacuum the peptide was precipitated in ethyl ether. After several rinses with ethyl ether followed by vacuum filtration, the peptide was dissolved in approximately 200 ml of 7M deionized urea containing 0.1M tris, 0.1M Na$_2$SO$_3$ and 0.01M Na$_2$S$_4$O$_6$. The solution was adjusted to pH 8.5 with 5N NaOH and allowed to stir vigorously overnight at 4° C.

The resulting S-sulfonated peptide solution was loaded onto a 5×215 cm column of Sephadex G-25 (Fine) at room temperature. The sample was eluted at 20 ml/min at room temperature using 50 mM ammonium bicarbonate. The effluent was monitored at 276 nm. 20 ml fractions were collected and a pool of the desired fractions was made and further purified by high performance liquid chromatography (HPLC) as follows.

The pool of the desired fractions was pumped onto a 2.5×30 cm DuPont C8, 9–12μ HPLC column and eluted using a linear gradient of increasing acetonitrile in 100 mM ammonium bicarbonate at room temperature (2.6 ml/min). The effluent was monitored at 280 nm. 25 ml fractions were collected. Analytical HPLC analyses were conducted on selected fractions to determine which fractions to retain. The desired fractions were pooled and lyophilized and used in the following combination with the A chain prepared as described above.

C. Preparation of Lys(B28), Pro(B29) Human Insulin

The combination of the A and B chain was accomplished by the procedure of Chance et al., supra. 700 mg of the recombinant DNA-derived A-chain S-sulfonate and 140 mg of the synthetic Lys(B28), Pro(B29) B-chain S-sulfonate (both obtained as described above) were each dissolved in 70 ml and 14 ml, respectively, of 0.1M glycine buffer at ambient temperature, each adjusted to pH 10.5 with 5N NaOH and then cooled to 5° C. 6 ml of a dithiothreitol (DTT) solution at 10.5 mg/ml was prepared in 0.1M glycine buffer at ambient temperature, adjusted to pH 10.5 with 5N NaOH and then cooled to 5° C.

The A- and B-chain solutions were combined, then 5.21 ml of the DTT solution was quickly added (SH/SSO$_3^-$= 0.90). The reaction solution was stirred at 5° C. in an open 200 ml glass centrifuge bottle for 2.5 hours at 5° C. 45 ml of glacial acetic acid was added and the solution was allowed to stand at 5° C. overnight.

The resultant precipitated mixture was centrifuged for 20 minutes at 2000 rpm at 5° C. The supernatant was combined with a 1M acetic acid wash of the pellet and placed on a 5×200 cm Sephadex G-50 (super-fine) column in molar acetic acid at 5° C. and eluted by gravity. Twenty-minute fractions were collected for three days. The fractions were examined at 276 nm and some by analytical HPLC. The fractions containing the Lys(B28), Pro(B29) sequence of the insulin analog were pooled and lyophilized giving a 125 mg sample. This sample was further purified by reverse-phase HPLC (using a 2.12×25 cm DuPont C8 column eluted at room temperature, at 2.6 ml/min, using a linear gradient of increasing acetonitrile in 0.1M $NaH_2PO_4$, pH 2.2). The effluent was monitored at 276 nm. Selected fractions were assayed by analytical HPLC. The desired fractions were pooled and further purified using pH 7 HPLC as follows.

The pool from the low pH HPLC preparation run was diluted approximately 2 times in an ice bath with 0.1M $(NH_4)_2HPO_4$. The pH was adjusted to 7 with cold 2N NaOH in an ice bath. The sample was loaded onto and eluted from the same HPLC column using the same conditions as the low pH preparation run except the eluting buffer was 0.1M, pH 7 $(NH_4)_2HPO_4$/acetonitrile.

The pool from the pH 7 HPLC preparative run was chilled in an ice bath and diluted two times with 0.1% aqueous trifluoroacetic acid (TFA). 1N HCl was added (cold, sample in ice bath) to lower the pH to 3. The sample was loaded onto a Vydac C4 or, alternatively a DuPont C8 HPLC column (2.12×25 cm) and eluted with a linear gradient of increasing acetonitrile in 0.1% aqueous TFA. The effluent was monitored at 214 nm or 276 nm. The desired fractions were pooled and lyophilized giving a sample yield of 41 mg of the desired analog of greater than 97 percent purity by reversephase HPLC.

EXAMPLE 2

Lys(B28), Pro(B29) Human Insulin

A second method for preparing Lys(B28), Pro(B29) human insulin employed enzymatic semisynthesis (reverse proteolysis) to combine des-octapeptide insulin ($A_{1-21}$-B1-22) with a synthetic octapeptide. The des-octapeptide insulin was obtained from a tryptic digest of natural pork or human insulin as described by Bromer and Chance, "Preparation and Characterization of Des-octapeptide-Insulin, *Biochim. Biophys. Acta*, 133:219–223 (1967) which is incorporated herein by reference. The synthetic octapeptide, Gly-Phe-Phe-Tyr-Thr-Lys -Pro-Thr, was prepared by automatic solid-phase synthesis in the manner described above.

Des-octapeptide insulin (435 mg) and 465 mg of synthetic Gly-Phe-Phe-Tyr-Thr-Lys-Pro-Thr were combined in 15 ml of a solution containing 1 part dimethyl sulfoxide, 2 parts 1,4-butanediol and 1 part 0.25M tris acetate buffer pH 7.3. The peptides were completely dissolved by warming the solution on a hot plate. The solution was then incubated at 37° C. and 90 mg of pork trypsin was added. The solution was stirred occasionally for 90 minutes at 37° C. The reaction was stopped by combining the solution with 135 ml of 0.05N HCl.

The titled insulin analog was purified by loading the acidified solution containing the analog onto a 2.5×25 cm C-8 Zorbax HPLC column and eluting it with a linear gradient of increasing acetonitrile in 0.1M sodium monobasic phosphate pH 2.2 buffer. The effluent was monitored at 276 nm. The desired fractions were pooled, diluted two-fold with water and loaded onto a 1×25 cm C-8 Ultrasphere HPLC column. The analog was eluted with a linear gradient of increasing acetonitrile in 0.5% aqueous TFA. The effluent was monitored at 276 nm. The desired fractions were again pooled and lyophilized to give 125 mg of the purified analog. The structure was verified by amino acid analysis (Table II) and mass spectroscopy (MS).

MS: 5809.2 (Theory: 5808.7).

Fast Atom Bombardment—Mass Spectroscopy analyses provided herein were determined using a VG-ZAB-25E double focusing mass spectrometer at a resolution of approximately 1500. The human insulin analogs were dissolved in a mixture of glycerol and thioglycerol containing oxalic acid. Cesium iodide was used to calibrate the instrument which was scanned magnetically from m/z 5300 to m/z 6500. Resulting data are presented as average mass+1.

EXAMPLE 3

Aba(B28), Pro(B29) Human Insulin

Pork des-octapeptide insulin (384 rag) and synthetic octapeptide Gly-Phe-Phe-Tyr-Thr-Aba-Pro-Thr (362 mg) were combined in 13 ml of a solution containing one part dimethyl sulfoxide, two parts 1,4-butanediol, and one part 0.25M tris pH 7.3 buffer at 37° C. Pork trypsin (75 mg) was added. The solution was mixed well and stirred occasionally for 120 min. at 37° C.

The reaction was stopped at this time by adding the mixture to 137 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 59 mg. The structure was verified by amino acid analysis (Table II) and mass spectroscopy (MS).

MS: 5765.7 (Theory: 5765.6).

EXAMPLE 4

Ala(B28), Pro(B29) Human Insulin

Pork des-octapeptide insulin (290 mg) and synthetic octapeptide Gly-Phe-Phe-Tyr-Thr-Ala-Pro-Thr (310 mg) were combined in 10 ml of a solution containing one part dimethyl sulfoxide, two parts 1,4-butanediol, and one part 0.25M tris pH 7.3 buffer at 37° C. Pork trypsin (60 mg) was added. The solution was mixed well and stirred occasionally for 60 min. at 37° C.

The reaction was stopped at this time by adding the mixture to 90 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 10×250 mm C-8 Ultrasphere column. The desalted protein was eluted from the column with an acetonitrile gradient in 0.5% trifluoroacetic acid. The fractions containing the purified insulin analog were pooled and lyophilized to yield 43 mg. The structure was verified by amino acid analysis (Table II) and mass spectroscopy (MS).

MS: 5752.3 (Theory: 5751.6).

EXAMPLE 5

Arg(B28), Pro(B29) Human Insulin

Pork des-octapeptide insulin (290 mg) and synthetic octapeptide Gly-Phe-Phe-Tyr-Thr-Arg-Pro-Thr (310 mg) were combined in 10 ml of a solution containing one part dimethyl sulfoxide, two parts 1,4-butanediol, and one part 0.25M tris pH 7.3 buffer at 37° C. Pork trypsin (60 mg) was added. The solution was mixed well and stirred occasionally for 60 min. at 37° C.

The reaction was stopped at this time by adding the mixture to 90 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 10×250 mm C-8 Ultrasphere column. The desalted protein was eluted from the column with an acetonitrile gradient in 0.5% trifluoroacetic acid. The fractions containing the purified insulin analog were pooled and lyophilized to yield 103 mg. The structure was verified by amino acid analysis (Table II) and mass spectroscopy (MS).

MS: 5836.1 (Theory: 5836.7).

EXAMPLE 6

Asn(B28), pro(B29) Human Insulin

Pork des-octapeptide insulin (409 mg) and synthetic octapeptide Gly-Phe-Phe-Tyr-Thr-Asn-Pro-Thr (398 mg) were combined in 14 ml of a solution containing one part dimethyl sulfoxide, two parts 1,4-butanediol, and one part 0.25M tris pH 7.3 buffer at 37° C. Pork trypsin (81 mg) was added. The solution was mixed well and stirred occasionally for 120 min. at 37° C.

The reaction was stopped at this time by adding the mixture to 136 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 56 mg. The structure was verified by amino acid analysis (Table II) and mass spectroscopy (MS).

MS: 5794.7 (Theory: 5794.6).

EXAMPLE 7

Asp(B28), Pro(B29) Human Insulin

Pork des-octapeptide insulin (400 mg) and synthetic octapeptide Gly-Phe-Phe-Tyr-Thr-Asp-Pro-Thr (388 mg) were combined in 13 ml of a solution containing one part dimethyl sulfoxide, two parts 1,4-butanediol, and one part 0.25M tris pH 7.3 buffer at 37° C. Pork trypsin (78 mg) was added. The solution was mixed well and stirred occasionally for 120 min. at 37° C.

The reaction was stopped at this time by adding the mixture to 137 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.1% trifluoroacetic acid. The fractions containing the purified insulin analog were pooled and lyophilized to yield 85 mg. The structure was verified by amino acid analysis (Table II) and mass spectroscopy (MS).

MS: 5795.7 (Theory: 5795.6).

EXAMPLE 8

Asp(B10), Lys(B28), Pro(B29) Human Insulin

A. Preparation of Asp(B10), Lys(B28), Pro(B29) Human Insulin B-Chain.

An Applied Biosystems 430A peptide synthesizer (including software revision 1.4) was used to prepare a crude peptidyl resin. 0.5 Millimoles (mMol) of the starting solid phase resin (t-BOC-Thr(Bzl)OCH$_2$ Pam resin) was used (0.72 mMol/g x 705 g). All amino acids used were BOC protected and, except for glutamic acid, aspartic acid, and histidine, all were used directly as received (i.e., in cartridges from Applied Biosystems, Inc.; each cartridge contained approximately 2 mmol of protected amino acid). Glutamic acid, aspartic acid, and histidine were obtained from commercial sources and transferred to cartridges such that each cartridge contained approximately 2 mmol of the desired protected amino acid. The crude peptidyl resin was dried under vacuum at room temperature overnight and its weight compared to the starting weight to assure reasonable weight gain. A small portion of sample was submitted for amino acid analysis to ensure that the desired amino acids were added in the correct proportions.

The peptide was cleaved from the peptidyl resin and side-chain deprotected by stirring for approximately 1 hour at 0° C. in a solution of 10 parts (v/w) HF (containing 5% v/v p-thiocresol and 5% v/v m-cresol) to 1 part peptidyl resin. After removal of most of the HF by vacuum the peptide was precipitated in ethyl ether. After several rinses with ethyl ether followed by vacuum filtration, the peptide was dissolved in approximately 120 ml of 8M guanidine HCl, pH 11, containing 0.1M TRIS, 35 mg/ml Na$_2$SO$_3$ and 25 mg/ml Na$_2$S$_4$O$_6$. The solution was adjusted to pH 8.8 with 5N NaOH and allowed to stir vigorously for 3 hours at room temperature.

The resulting S-sulfonated peptide solution was loaded onto a 5×215 cm column of Sephadex G-25 (medium) at room temperature. The sample was eluted at 21 ml/min. at room temperature using 50 mM ammonium bicarbonate. The effluent was monitored at 276 nm. Fractions of 25 ml each were collected, and a pool of the desired fractions was made and further purified by high performance liquid chromatography (HPLC) as follows.

The pool of the desired fractions was pumped onto a 2.5×30 cm DuPont C8, 9–12µ HPLC column and eluted using a linear gradient of increasing acetonitrile in 100 mM ammonium bicarbonate at room temperature (2.6 ml/min.). The effluent was monitored at 280 nm. Fractions (25 ml each) were collected. Analytical HPLC analyses were conducted on selected fractions to determine which fractions to retain. The desired fractions were pooled and lyophilized and used in the following combination with the A chain.

B. Combination of Asp(B10), Lys(B28), Pro(B29) Human Insulin B-Chain with Human Insulin A-Chain.

The combination of the A and B Chains was accomplished by the procedure of Chance et al., supra. Two g of the recombinant DNA-derived A-chain S-sulfonate and 400 mg of the synthetic Asp(B10), Lys(B28), Pro(B29) B-chain S-sulfonate were each dissolved in 200 ml and 40 ml, respectively, of 0.1M glycine buffer at ambient temperature, each adjusted to pH 10.5 with 5N NaOH and then cooled to 5° C. A dithiothreitol (DTT) solution at 15.5 mg/ml was prepared in 0.1M glycine buffer at ambient temperature, adjusted to pH 10.5 with 5N NaOH and then cooled to 5° C.

The A- and B-chain solutions were combined, then 15.9 ml of the DTT solution were quickly added (SH/SSO$_3^-$ = 1.0). The reaction solution was stirred at 4° C. in an open 200 ml glass centrifuge bottle for 19.6 hours at 4° C. Glacial acetic acid (129 ml) was added, and the solution was allowed to stand at 4° C. for one hour.

The resultant precipitated mixture was centrifuged for 30 minutes at 2000 rpm at 4° C. The supernatant was combined with 292 ml milli-Q water and 73 ml acetonitrile and further purified by reversed-phase HPLC (using a 2.5×30 cm Vydac C18 column eluted at room temperature, at 2.6 ml/min., using a linear gradient of increasing acetonitrile in 0.1M NaH$_2$PO$_4$, pH 2.1). The effluent was monitored at 280 nm. Selected fractions were assayed by analytical HPLC and the desired fractions pooled and diluted two-fold with 0.1% aqueous trifluoroacetic acid (TFA), then loaded onto an Ultrasphere octyl HPLC column (1.0×25 cm) and eluted with a linear gradient of increasing acetonitrile in 0.1% aqueous TFA. The effluent was monitored at 280 nm. Selected fractions were assayed by analytical HPLC and the desired fractions pooled and repurified using the same column and conditions as above with a slightly different gradient of acetonitrile. The appropriate fractions were pooled and lyophilized giving a yield of 65 mg of the insulin analog of greater than 93% purity by reversed-phase HPLC. The structure was verified by amino acid analysis (Table II) and mass spectroscopy (MS).

MS: 5786.1 (Theory: 5786.7).

EXAMPLE 9

Cya(B28), Pro(B29) Human Insulin

Performic acid oxidation was performed to convert the cysteine of the octapeptide to the cysteic acid form. The synthetic octapeptide Gly-Phe-Phe-Tyr-Thr-Cys-Pro-Thr (363 mg) was dissolved in 36 ml freshly prepared performic acid in an ice-cooled flask, and allowed to stir gently for one hour. The oxidized material was diluted ten-fold with water and lyophilized. The lyophilizate was used in the semisynthesis.

Pork des-octapeptide insulin (222 mg) and synthetic octapeptide Gly-Phe-Phe-Tyr-Thr-Cya-Pro-Thr (225 mg) were combined in 18 ml of a solution containing one part dimethyl sulfoxide, two parts 1,4-butanediol, and one part 0.25M tris pH 7.3 buffer at 37° C. Pork trypsin (45 mg) was added. The solution was mixed well and stirred occasionally for 120 min. at 37° C.

The reaction was stopped at this time by adding the mixture to 242 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 16 mg. The structure was verified by amino acid analysis (Table II) and mass spectroscopy (MS).

MS: 5831.5 (Theory: 5831.7).

EXAMPLE 10

Gln(B28), Pro(B29) Human Insulin

Pork des-octapeptide insulin (290 mg) and synthetic octapeptide Gly-Phe-Phe-Tyr-Thr-Gln-Pro-Thr (310 mg) were combined in 10 ml of a solution containing one part dimethyl sulfoxide, two parts 1,4-butanediol, and one part 0.25M tris pH 7.3 buffer at 37° C. Pork trypsin (60 mg) was added. The solution was mixed well and stirred occasionally for 60 min. at 37° C.

The reaction was stopped at this time by adding the mixture to 90 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 10×250 mm C-8 Ultrasphere column. The desalted protein was eluted from the column with an acetonitrile gradient in 0.5% trifluoroacetic acid. The fractions containing the purified insulin analog were pooled and lyophilized to yield 87 mg. The structure was verified by amino acid analysis (Table II) and mass spectroscopy (MS).

MS: 5809.4 (Theory: 5808.6).

EXAMPLE 11

Glu (B28), Pro(B29) Human Insulin

Pork des-octapeptide insulin (402 mg) and synthetic octapeptide Gly-Phe-Phe-Tyr-Thr-Glu-Pro-Thr (398 mg) were combined in 14 ml of a solution containing one part dimethyl sulfoxide, two parts 1,4-butanediol, and one part 0.25M tris pH 7.3 buffer at 37° C. Pork trypsin (80 mg) was added. The solution was mixed well and stirred occasionally for 120 min. at 37° C.

The reaction was stopped at this time by adding the mixture to 136 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 59 mg. The structure was verified by amino acid analysis (Table II) and mass spectroscopy (MS).

MS: 5809.6 (Theory: 5809.6).

EXAMPLE 12

Gly(B28), Pro(B29) Human Insulin

Pork des-octapeptide insulin (412 mg) and synthetic octapeptide Gly-Phe-Phe-Tyr-Thr-Gly-Pro-Thr (376 mg) were combined in 13 ml of a solution containing one part dimethyl sulfoxide, two parts 1,4-butanediol, and one part 0.25M tris pH 7.3 buffer at 37° C. Pork trypsin (79 mg) was added. The solution was mixed well and stirred occasionally for 180 min. at 37° C.

The reaction was stopped at this time by adding the mixture to 147 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.1% trifluoroacetic acid. The fractions containing the purified insulin analog were pooled and lyophilized to yield 11 mg. The structure was verified by amino acid analysis (Table II) and mass spectroscopy (MS).

MS: 5737.2 (Theory: 5737.6).

EXAMPLE 13

His(B28), Pro(B29) Human Insulin

Pork des-octapeptide insulin (400 mg) and synthetic octapeptide Gly-Phe-Phe-Tyr-Thr-His-Pro-Thr (398 mg) were combined in 13 ml of a solution containing one part dimethyl sulfoxide, two parts 1,4-butanediol, and one part 0.25M tris pH 7.3 buffer at 37° C. Pork trypsin (79 mg) was added. The solution was mixed well and stirred occasionally for 120 min. at 37° C.

The reaction was stopped at this time by adding the mixture to 237 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.1% trifluoroacetic acid. The fractions containing the purified insulin analog were pooled and lyophilized to yield 79 mg. The structure was verified by amino acid analysis (Table II) and mass spectroscopy (MS).

MS: 5816.9 (Theory: 5817.7).

EXAMPLE 14

Ile(B28), Pro(B29) Human Insulin

Pork des-octapeptide insulin (409 mg) and synthetic octapeptide Gly-Phe-Phe-Tyr-Thr-Ile-Pro-Thr (398 mg) were combined in 13 ml of a solution containing one part dimethyl sulfoxide, two parts 1,4-butanediol, and one part 0.25M tris pH 7.3 buffer at 37° C. Pork trypsin (81 mg) was added. The solution was mixed well and stirred occasionally for 120 min. at 37° C.

The reaction was stopped at this time by adding the mixture to 136 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 57 mg. The structure was verified by amino acid analysis (Table II) and mass spectroscopy (MS).

MS: 5793.7 (Theory: 5793.7).

EXAMPLE 15

Leu(B28), Pro(B29) Human Insulin

Pork des-octapeptide insulin (418 mg) and synthetic octapeptide Gly-Phe-Phe-Tyr-Thr-Leu-Pro-Thr (410 mg) were combined in 14 ml of a solution containing one part dimethyl sulfoxide, two parts 1,4-butanediol, and one part 0.25M tris pH 7.3 buffer at 37° C. Pork trypsin (83 mg) was added. The solution was mixed well and stirred occasionally for 120 min. at 37° C.

The reaction was stopped at this time by adding the mixture to 136 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 74 mg. The structure was verified by amino acid analysis (Table II) and mass spectroscopy (MS).

MS: 5793.8 (Theory: 5793.7).

EXAMPLE 16

Nle(B28), Pro(B29) Human Insulin

Pork des-octapeptide insulin (290 mg) and synthetic octapeptide Gly-Phe-Phe-Tyr-Thr-Nle-Pro-Thr (310 mg) were combined in 10 ml of a solution containing one part dimethyl sulfoxide, two parts 1,4-butanediol, and one part 0.25M tris pH 7.3 buffer at 37° C. Pork trypsin (60 mg) was added. The solution was mixed well and stirred occasionally for 60 min. at 37° C.

The reaction was stopped at this time by adding the mixture to 90 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 10×250 mm C-8 Ultrasphere column. The desalted protein was eluted from the column with an acetonitrile gradient in 0.5% trifluoroacetic acid. The fractions containing the purified insulin analog were pooled and lyophilized to yield 54 mg. The structure was verified by amino acid analysis (Table II) and mass spectroscopy (MS).

MS: 5794.6 (Theory: 5793.7).

EXAMPLE 17

Met(B28), Pro(B29) Human Insulin

Pork des-octapeptide insulin (350 mg) and synthetic octapeptide Gly-Phe-Phe-Tyr-Thr-Met-Pro-Thr (366 mg) were combined in 12 ml of a solution containing one part dimethyl sulfoxide, two parts 1,4-butanediol, and one part 0.25M tris pH 7.3 buffer at 37° C. Pork trypsin (71 mg) was added. The solution was mixed well and stirred occasionally for 120 min. at 37° C.

The reaction was stopped at this time by adding the mixture to 118 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.1% trifluoroacetic acid. The fractions containing the purified insulin analog were pooled and lyophilized to yield 72 mg. The structure was verified by amino acid analysis (Table II) and mass spectroscopy (MS).

MS: 5811.8 (Theory: 5811.7).

EXAMPLE 18

Orn(B28), Pro(B29) Human Insulin

Pork des-octapeptide insulin (290 mg) and synthetic octapeptide Gly-Phe-Phe-Tyr-Thr-Orn-Pro-Thr (310 mg) were combined in 10 ml of a solution containing one part dimethyl sulfoxide, two parts 1,4-butanediol, and one part 0.25M tris pH 7.3 buffer at 37° C. Pork trypsin (60 mg) was added. The solution was mixed well and stirred occasionally for 90 min. at 37° C.

The reaction was stopped at this time by adding the mixture to 90 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 10×250 mm C-8 Ultrasphere column. The desalted protein was eluted from the column with an acetonitrile gradient in 0.5% trifluoroacetic acid. The fractions containing the purified insulin analog were pooled and lyophilized to yield 89 mg. The structure was verified by amino acid analysis (Table II) and mass spectroscopy (MS).

MS: 5795.2 (Theory: 5794.7).

EXAMPLE 19

Phe(B28), Pro(B29) Human Insulin

Pork des-octapeptide insulin (290 mg) and synthetic octapeptide Gly-Phe-Phe-Tyr-Thr-Phe-Pro-Thr (310 mg) were combined in 10 ml of a solution containing one part dimethyl sulfoxide, two parts 1,4-butanediol, and one part 0.25M tris pH 7.3 buffer at 37° C. Pork trypsin (60 mg) was added. The solution was mixed well and stirred occasionally for 80 min. at 37° C.

The reaction was stopped at this time by adding the mixture to 90 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.1% trifluoroacetic acid. The fractions containing the purified insulin analog were pooled and lyophilized to yield 17 mg. The structure was verified by amino acid analysis (Table II) and mass spectroscopy (MS).

MS: 5827.9 (Theory: 5827.7).

EXAMPLE 20

Pro(B29) Human Insulin

Pork des-octapeptide insulin (339 mg) and synthetic octapeptide Gly-Phe-Phe-Tyr-Thr-Pro-Pro-Thr (363 mg) were combined in 9 ml of a solution containing one part dimethyl sulfoxide, two parts 1,4-butanediol, and one part 0.25M tris pH 7.3 buffer at 37° C. Pork trypsin (70 mg) was added. The solution was mixed well and stirred occasionally for 80 min. at 37° C.

The reaction was stopped at this time by adding the mixture to 108 ml of 0.05N HCl. The entire solution was pumped onto a 10×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 10×250 mm C-8 Ultrasphere column. The desalted protein was eluted from the column with an acetonitrile gradient in 0.5% trifluoroacetic acid. The fractions containing the purified insulin analog were pooled and lyophilized to yield 97 mg. The structure was verified by amino acid analysis (Table II) and mass spectroscopy (MS).

MS: 5778.6 (Theory: 5777.6).

EXAMPLE 21

Ser(B28), Pro(B29) Human Insulin

Pork des-octapeptide insulin (412 mg) and synthetic octapeptide Gly-Phe-Phe-Tyr-Thr-Ser-Pro-Thr (390 mg) were combined in 13 ml of a solution containing one part dimethyl sulfoxide, two parts 1,4-butanediol, and one part 0.25M tris pH 7.3 buffer at 37° C. Pork trypsin (80 mg) was added. The solution was mixed well and stirred occasionally for 120 min. at 37° C.

The reaction was stopped at this time by adding the mixture to 137 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 37 mg. The structure was verified by amino acid analysis (Table II) and mass spectroscopy (MS).

MS: 5768.1 (Theory: 5767.6).

EXAMPLE 22

Thr(B28), Pro(B29) Human Insulin

Pork des-octapeptide insulin (437 mg) and synthetic octapeptide Gly-Phe-Phe-Tyr-Thr-Thr-Pro-Thr (420 mg) were combined in 14.5 ml of a solution containing one part dimethyl sulfoxide, two parts 1,4-butanediol, and one part 0.25M tris pH 7.3 buffer at 37° C. Pork trypsin (86 mg) was added. The solution was mixed well and stirred occasionally for 120 min. at 37° C.

The reaction was stopped at this time by adding the mixture to 135.5 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 78 mg. The structure was verified by amino acid analysis (Table II) and mass spectroscopy (MS).

MS: 5781.9 (Theory: 5781.6).

EXAMPLE 23

Trp(B28), Pro(B29) Human Insulin

Pork des-octapeptide insulin (310 mg) and synthetic octapeptide Gly-Phe-Phe-Tyr-Thr-Trp-Pro-Thr (325 mg) were combined in 10.5 ml of a solution containing one part dimethyl sulfoxide, two parts 1,4-butanediol, and one part 0.25M tris pH 7.3 buffer at 37° C. Pork trypsin (64 mg) was added. The solution was mixed well and stirred occasionally for 120 min. at 37° C.

The reaction was stopped at this time by adding the mixture to 140 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 47 mg. The structure was verified by amino acid analysis (Table II) and mass spectroscopy (MS).

MS: 5866.2 (Theory: 5866.7).

EXAMPLE 24

Tyr(B28), Pro(B29) Human Insulin

Pork des-octapeptide insulin (391 mg) and synthetic octapeptide Gly-Phe-Phe-Tyr-Thr-Tyr-Pro-Thr (400 mg) were combined in 13 ml of a solution containing one part dimethyl sulfoxide, two parts 1,4-butanediol, and one part 0.25M tris pH 7.3 buffer at 37° C. Pork trypsin (79 mg) was added. The solution was mixed well and stirred occasionally for 120 min. at 37° C.

The reaction was stopped at this time by adding the mixture to 137 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 30 mg. The structure was verified by amino acid analysis (Table II) and mass spectroscopy (MS).

MS: 5843.7 (Theory: 5843.7).

EXAMPLE 25

Val(B28), pro(B29) Human Insulin

Pork des-octapeptide insulin (400 mg) and synthetic octapeptide Gly-Phe-Phe-Tyr-Thr-Val-Pro-Thr (383 mg) were combined in 12 ml of a solution containing one part dimethyl sulfoxide, two parts 1,4-butanediol, and one part 0.25M tris pH 7.3 buffer at 37° C. Pork trypsin (78 mg) was added. The solution was mixed well and stirred occasionally for 120 min. at 37° C.

The reaction was stopped at this time by adding the mixture to 238 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted four-fold with water, and pumped onto a 25×300 mm C-18 Vydac column. The desalted protein was eluted from the column with an acetonitrile gradient in 0.1% trifluoroacetic acid. The fractions containing the purified insulin analog were pooled and lyophilized to yield 74 mg. The structure was verified by amino acid analysis (Table II) and mass spectroscopy (MS).

MS: 5780.0 (Theory: 5779.6).

EXAMPLE 26

Nva(B28), Pro(B29) Human Insulin

Pork des-octapeptide insulin (292 mg) and synthetic octapeptide Gly-Phe-Phe-Tyr-Thr-Nva-Pro-Thr (279 mg) were combined in 10 ml of a solution containing one part dimethyl sulfoxide, two parts 1,4-butanediol, and one part 0.25M tris pH 7.3 buffer at 37° C. Pork trypsin (57 mg) was added. The solution was mixed well and stirred occasionally for 120 min. at 37° C.

The reaction was stopped at this time by adding the mixture to 240 ml of 0.05N HCl. The entire solution was pumped onto a 21×250 mm C-8 Zorbax column, and the products were eluted in a shallow acetonitrile gradient in 0.1M sodium monobasic phosphate, pH 2 buffer.

The appropriate fractions, as determined by analytical HPLC, were pooled, diluted two-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 51 mg. The structure was verified by amino acid analysis (Table II) and mass spectroscopy (MS).

MS: 5780.0 (Theory: 5779.6).

EXAMPLE 27

Utilizing the procedures set forth herein, the following additional insulin analogs are prepared:

(a) Asp(B1),Lys(B28),Pro(B29) Human Insulin (b) des(Phe-B1),Lys(B28),Pro(B29) Human Insulin (c) des(Phe-B1),Asp(B10),Lys(B28),Pro(B29) Human Insulin (d) des(Phe-B1,Val-B2),Lys(B28),Pro(B29) Human Insulin (e) des(Phe-B1,Val-B2),Asp(B10),Lys(B28), Pro(B29) Human Insulin (f) Gly(A21),Asp(B10),Lys(B28),Pro(B29) Human Insulin (g) Ala(A21),Asp(B10),Lys(B28),Pro(B29) Human Insulin (h) des(Thr-B30),Lys(B28),Pro(B29) Human Insulin (i) Asp(B10),Arg(B28),Pro(B29) Human Insulin (j) Ala(A21),Arg(B28),Pro(B29) Human Insulin (k) Asp(B1),Arg(B28),Pro(B29) Human Insulin

EXAMPLE 28

Lys(B28), Pro(B29) Human Insulin

Construction of Recombinant Vectors and Hosts

A. Construction of Plasmid pCZR126S

1. Isolation of Plasmid pKC283

Lyophils of *E. coli* K12 BE1201/pKC283 are obtained from the Northern Regional Research Laboratory, Peoria, Illinois 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 µg/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 µg/ml ampicillin in a manner so as to obtain a single colony isolate of *E. coli* K12 BE1201/pKC283. The single colony obtained was inoculated into 10 ml of LB medium containing 50 µg/ml ampicillin and incubated overnight at 32° C. with vigorous shaking. The 10 ml overnight culture was inoculated into 500 ml LB medium containing 50 µg/ml ampicillin and incubated at 32° C. with vigorous shaking until the culture reached stationary phase.

The following procedure is adapted from Maniatis et al., 1982, *Molecular Cloning* (Cold Spring Harbor Laboratory).

The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl, pH 7.8; and 1 mMEDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentraton was about 600 µg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 µg/µl. A restriction site and function map of plasmid pKC283 is presented in FIG. 1 of the accompanying drawings.

2. Construction of Plasmid pKC283PX

About 10 µl of the plasmid pKC283 DNA prepared in Example 28A1 were mixed with 20 µl 10×medium-salt restriction buffer (500 mM NaCl; 100 mM Tris-HCl, pH 7.5; 100 mM MgCl$_2$; and 10 mM DTT), 20 µl mg/ml BSA, 5 µl restriction enzyme PvuII (~50 Units, as defined by Bethesda Research Laboratories (BRL), from which all restriction enzymes used herein were obtained), and 145 µl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 µl of TE buffer.

About 600 picomoles (pM) of XhoI linkers (5'-CCTC-GAGG-3') were kinased in a mixture containing 10 µl 15×Kinase Buffer (300 mM Tris-HCl, pH 7.8; 50 mM MgC$_2$; and 25 mMDTT), 5 µl 15 mM ATP, 24 µl H$_2$O, 0.5 µl of T4 polynucleotide kinase (about 2.5 units as defined by P-L Biochemicals), 5 µl mg/ml BSA, and 5 µl of 10 mM spermidine by incubating the mixture at 37° C. for 30 minutes.

About 12.5 µl of the kinased XhoI linkers were added to the 5 µl of PvuII-digested plasmid pKC283 DNA, and then 2.5 µl of 10×ligase buffer (300 mM Tris-HCl, pH 7.6; 100 mM MgCl$_2$; and 50 mM DTT), 2.5 µl of 1 mg/ml BSA, 7 µl of 5 mM ATP, 2.5 µl (about 2.5 units as defined by P-L Biochemicals) of T4 DNA ligase, 2.5 µl of 10 mM spermidine, and 3 µl of water were added to the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10.0 mM MgCl$_2$; and 1 mM DTT). About 10 µl (100 units) of restriction enzyme XhOI were added to the mixture, and the resulting reaction was incubated at 37° C. for 2 hours.

Figure 2:
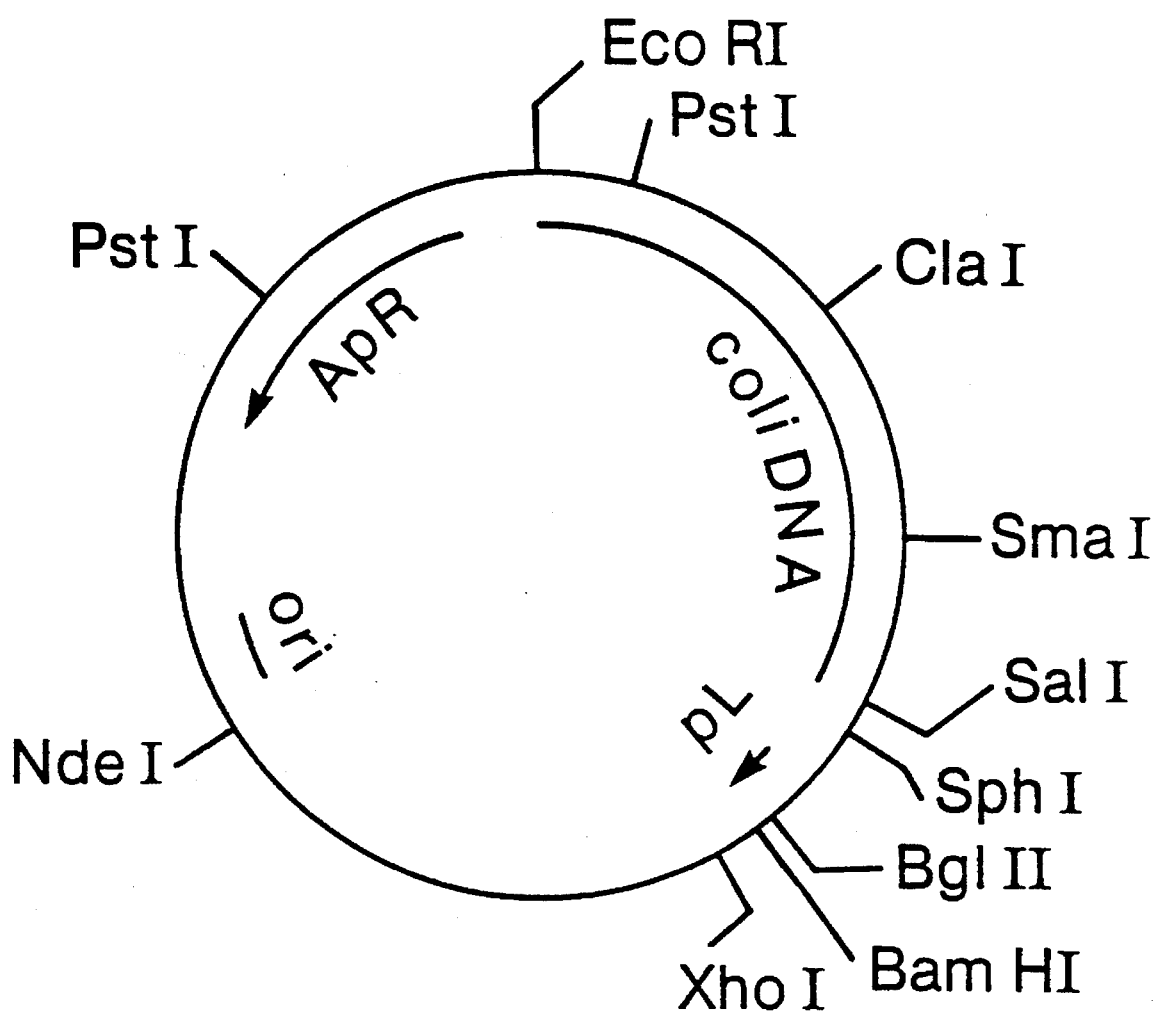
FIG. 2—A restriction site and function map of plasmid pKC283PX.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 2 of the accompanying drawings.

3. Construction of *E. coli* K12 MO(λ⁺)/pKC283PX

*E. coli* K12 MO(λ⁺) can be obtained from the Northern Regional Research Laboratories in lyophylized form under the accession number NRRL B-15993. *E. coli* K12 MO(λ⁺) comprises the wild-type lambda pL cI repressor gene, so that transcription from the hybrid pL-lpp promoter of the present invention does not occur in *E. coli* K12 MO(λ⁺) cells. The lyophils are reconstituted, single colonies of MO(λ⁺) are isolated, and a 10 ml overnight culture of the MO(λ⁺)cells is prepared in substantial accordance with the procedure of Example 28A1, except that the temperature of incubation is 37° C. and no ampicillin is used in the growth media.

Fifty µl of the overnight culture were used to inoculate 5 ml of LB media which also contained 10 mM $MgSO_4$ and 10 mM $MgCl_2$. The culture was incubated at 37° C. overnight with vigorous shaking. The following morning, the culture was diluted to 200 ml with LB media containing 10 mM $MgSO_4$ and 10 mM $MgCl_2$. The diluted culture was incubated at 37° C. with vigorous shaking until the absorbance at 550 nm ($A_{550}$) was about 0.5, which indicated a cell density of about $1 \times 10^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM $MgSO_4$ and then immediately re-pelleted by centrifugation. The cell pellet was resuspended in 100 ml of 30 mM $CaCl_2$ and incubated on ice for 20 minutes.

The cells were again collected by centrifugation and resuspended in 10 ml of 30 mM $CaCl_2$. A one-half ml aliquot of the cells was added to the ligated DNA prepared in Example 28A2; the DNA had been made 30 mM in $CaCl_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred µl aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 28A1, but the CsCl gradient step was omitted until the desired *E. coli* K12 MO(λ⁺)/pKC283PX transformants were identified. A restriction site and function map of plasmid pKC283PX is presented in FIG. 2 of the accompanying drawings.

Construction of *E. coli* K12 MO(λ⁺)/pKC283-L

Ten µg of plasmid pKC283PX DNA prepared in accordance with the procedure of Example 28A1 were dissolved in 20 µl of 10X high-salt buffer, 20 µl mg/ml BSA, 5 µl (~50 units) restriction enzyme BglII, 5µl (~50 units) restriction enzyme XhoI, and 150 µl of water, and the resulting reaction was incubated at 37° C. for two hours. The reaction was stopped, and after precipitating the BglII-XhoI digested DNA, the DNA was resuspended in 5 µl of TE buffer.

A DNA linker with single-stranded DNA ends characteristic of BglII and XhoI restriction enzyme cleavage was synthesized and kinased. The linker was kinased in substantial accordance with the procedure of Example 28A2. The DNA linker had the following structure:

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, *Science* 198:1056 and in Crea et al., 1978, *Proc. Nat'l Acad. Sci. USA* 75:5765. In addition, an especially preferred method of synthesizing DNA is disclosed in Hsiung et al., 1983, *Nuc. Acid Res.* 11:3227 and Narang et al., 1980, *Methods in Enzymology* 68:90.

Figure 3:
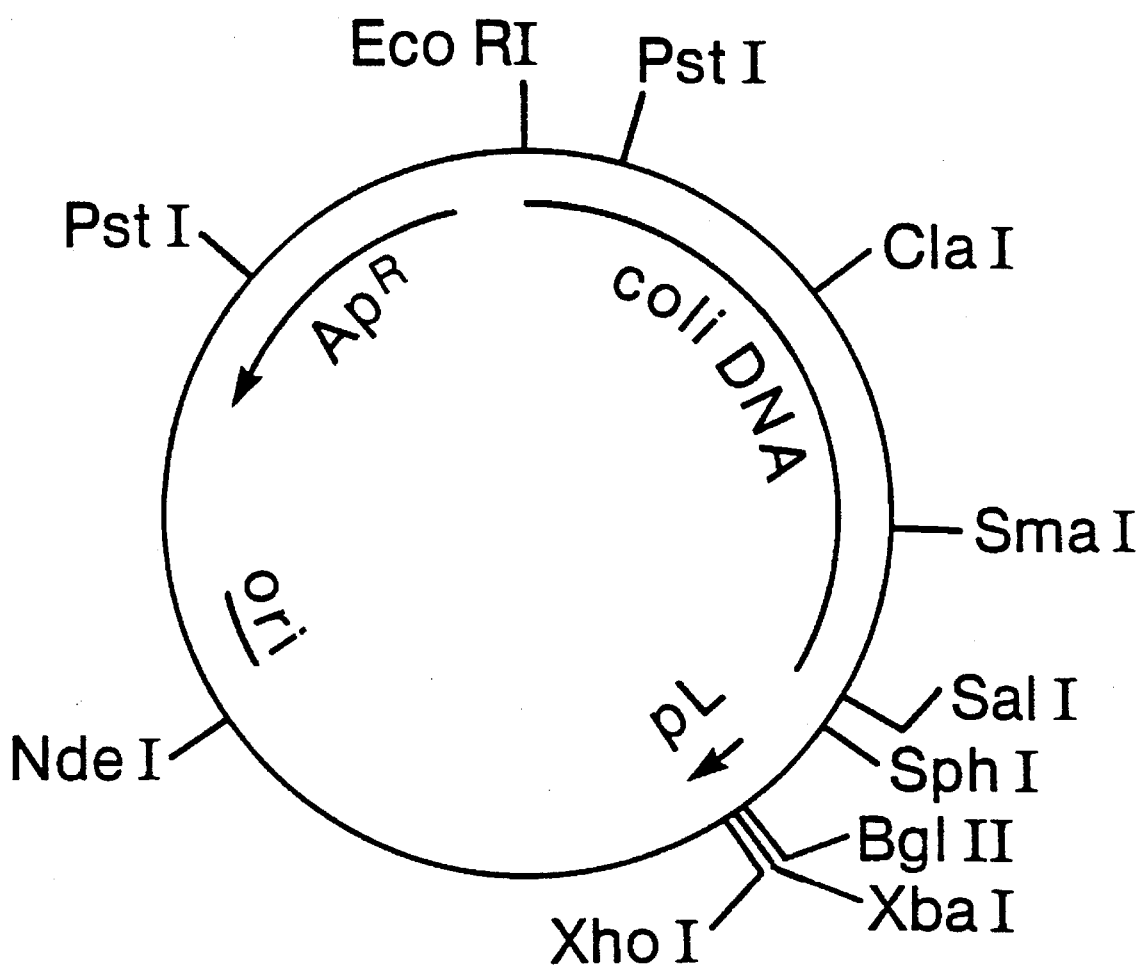
FIG. 3—A restriction site and function map of plasmid pKC283-L.

The linker and BglII-XhoI-digested plasmid pKC283PX were ligated in substantial accordance with the procedure of Example 28A2. The ligated DNA constituted the desired plasmid pKC283-L. A restriction site and function map of plasmid pKC283-L is presented in Figure 3 of the accompanying drawings. The plasmid pKC283-L DNA was used to transform *E. coli* K12 MO(λ⁺) and the resulting *E. coli* K12 MO(λ⁺)/pKC283-L transformants were identified in substantial accordance with the procedure of Example 28A3.

5. Construction of *E. coli* K12 MO(λ⁺)/pKC283-LB

About 10 µg of plasmid pKC283-L DNA, prepared in substantial accordance with the procedures of Example 28A1, were dissolved in 20 µl 10× high-salt buffer, 20 µl 1 mg/ml BSA, 5 µl 1 (~50 units) restriction enzyme xhoI, and 155 µl 1 of $H_2O$, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubation in a dry ice-ethanol bath for five minutes, and centrifugation. The resulting DNA pellet was washed with 70% ethanol, dried, and resuspended in 2 µl 10×nick-translation buffer (0.5M Tris-HCl, pH 7.2; 0.1 M $MgSO_4$; and 1 mM DTT), 1 µl of a solution 2 mM in each of the deoxynucleotide triphosphates, 15 µl of $H_2O$, 1 µl (~6 units as defined by P-L Biochemicals) of Klenow, which is the large fragment of *E. coli* DNA polymerase I, and 1 µl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the procedure of Example 28A2. After the ligation reaction, the DNA was digested with about 100 units of BamHI for about 2 hours at 37° C. in high-salt buffer. After the BamHI digestion, the DNA was prepared for ligation in substantial accordance with the procedure of Example 28A2.

Figure 4:
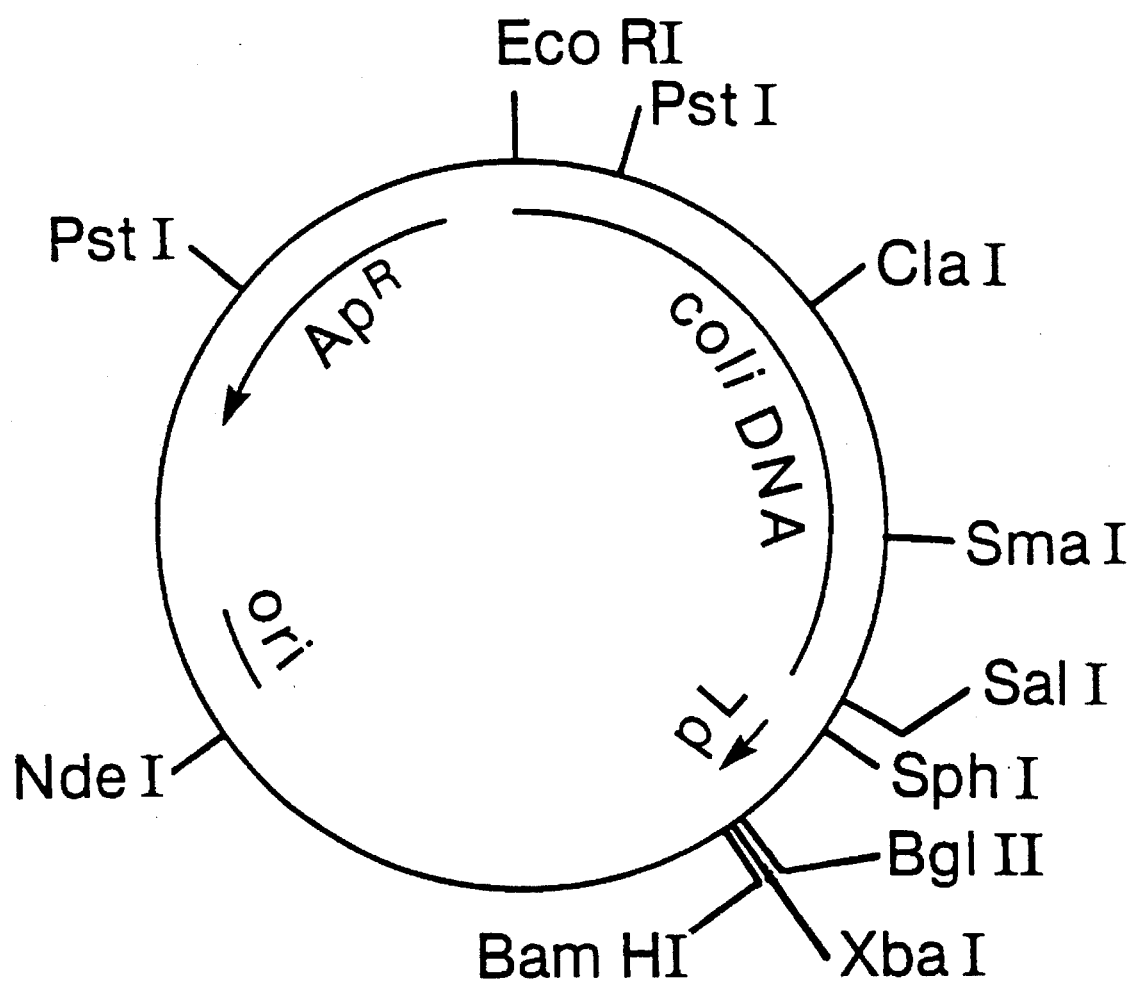
FIG. 4—A restriction site and function map of plasmid pKC283-LB.

The ~5.9 kb BamHI restriction fragment was circularized by ligation and transformed into *E. coli* K12 MO(λ⁺) in substantial accordance with the procedures of Examples 28A2 and 28A3. The *E. coli* K12 MO(λ⁺)/pKC283-LB transformants were identified, and then plasmid pKC283-LB DNA was prepared in substantial accordance with the procedure of Example 28A1. A restriction site and function map of plasmid pKC283-LB is presented in FIG. 4 of the accompanying drawings.

6. Construction of *E. coli* K12 MO(λ⁺)/pL32

Figure 5:
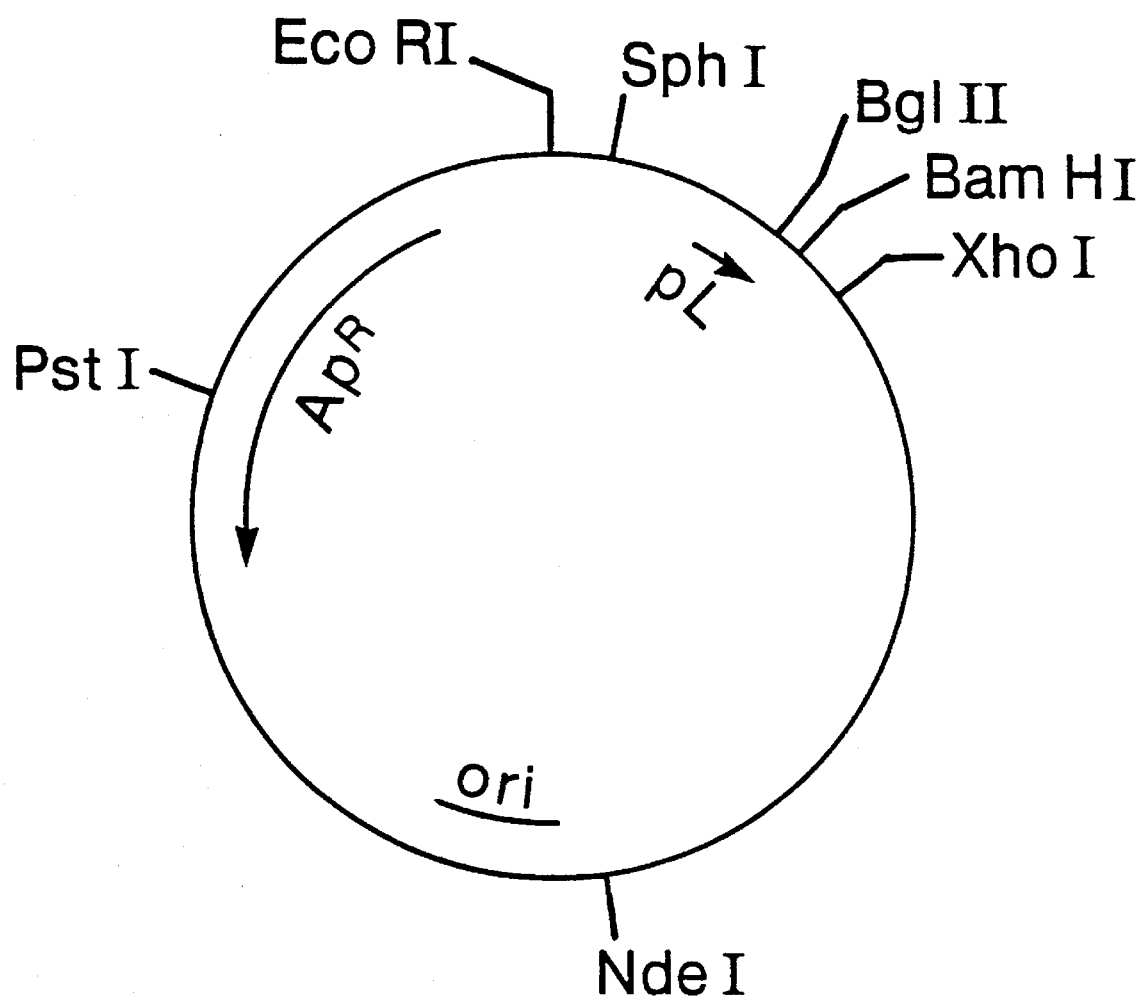
FIG. 5—A restriction site and function map of plasmid pKC283-PRS.

About 10 μg of plasmid pKC283PX were digested with restriction enzyme SalI in high-salt buffer, treated with Klenow, and ligated to EcoRI linkers (5'-GAGGAATTC-CTC-3') in substantial accordance with the procedure of Example 28A5, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform *E. coli* K12 MO(λ⁺) in substantial accordance with the procedure of Example 28A3. After the *E. coli* K12 MO(λ⁺)/pKC283PRS transformants were identified, plasmid pKC283PRS DNA was prepared in substantial accordance with the procedure of Example 28A1. A restriction site and function map of plasmid pKC283PRS is presented in FIG. 5 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Maine 04841) gel for 2–3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HC1, pH 7.6, was added to the tube containing the segment. The segment was then melted by incubation at 72° C. About 1 μg of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

Figure 6:
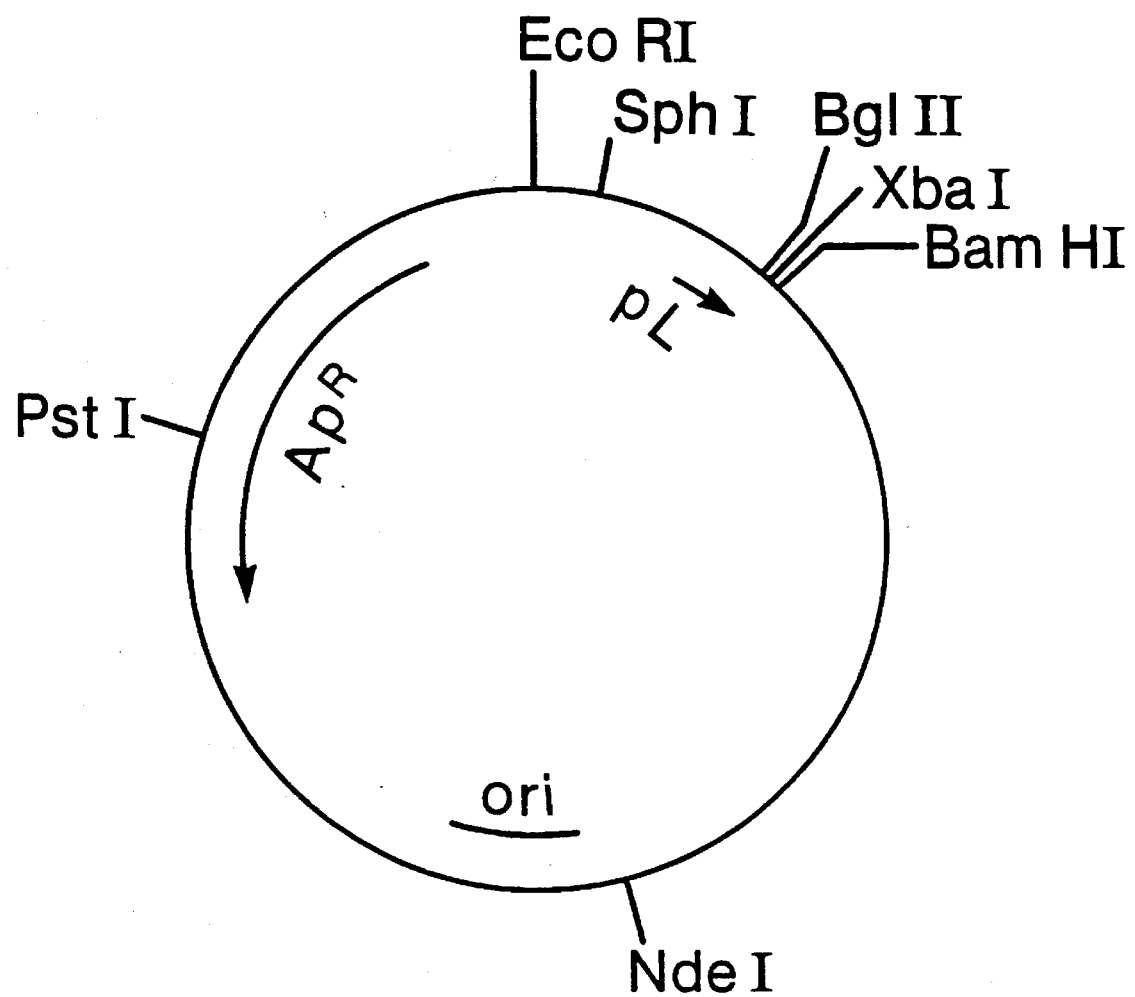
FIG. 6—A restriction site and function map of plasmid pL32.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 28A2. The ligated DNA constituted the desired plasmid pL32. A restriction site and function map of plasmid pL32 is presented in FIG. 6 of the accompanying drawings. Plasmid pL32 was transformed into *E. coli* K12 MO(λ⁺) cells in substantial accordance with the procedure of Example 28A3. Plasmid pL32 DNA was prepared from the *E. coli* K12 MO(λ⁺)/pL32 transformants in substantial accordance with the procedure of Example 28A1. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together. Alternatively, plasmid pL32 may be constructed by carrying out the SalI-EcoRI excision and ligation of the first paragraph of this Example upon plasmid pKC283-LB.

7. Construction of *E. coli* K12 MO(λ⁺)/pL47

Figure 7:
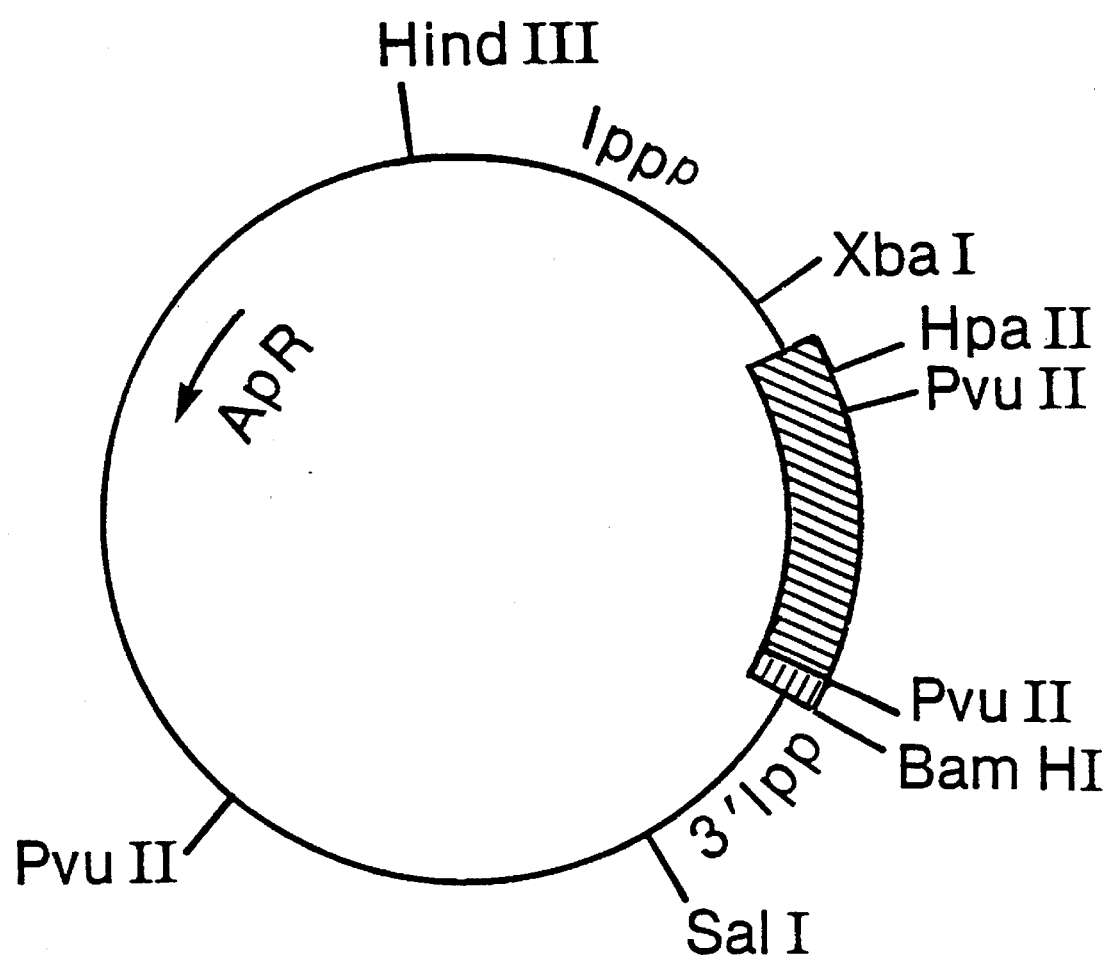
FIG. 7—A restriction site and function map of plasmid pNM789.
Figure 8:
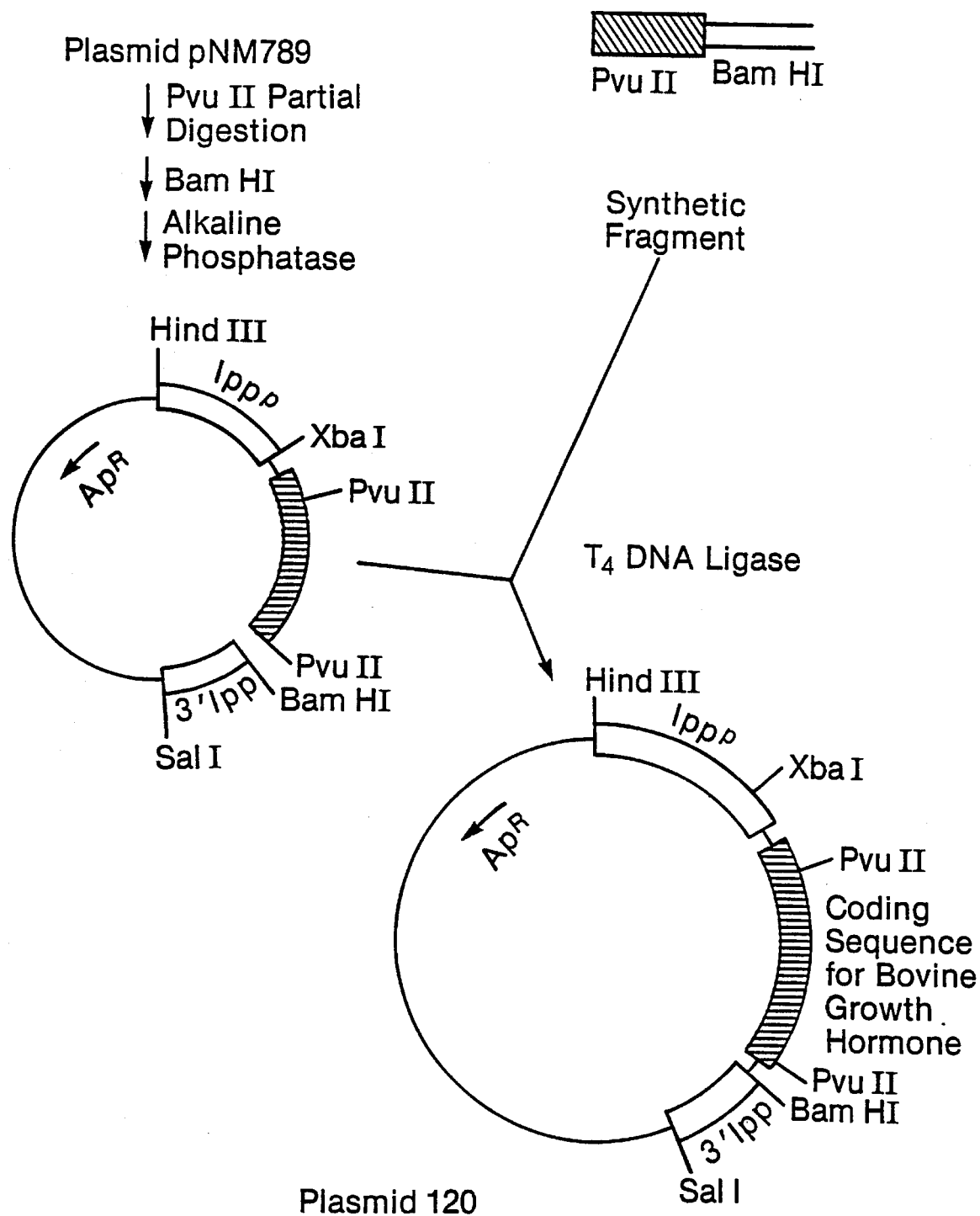
FIG. 8—A schematic outline of the construction of plasmid 120.

*E. coli* K12 RV308/pNM789 can be obtained from the Northern Regional Research Laboratories in lyophilized form under the accession number NRRL B-18216. A restriction site and function map of pNM789 is presented in FIG. 7 of the accompanying drawings. Plasmid DNA is extracted from the culture in substantial accordance with the teaching of Example 28A1, except that the temperature of incubation is 37° C. Ten micrograms of pNM789 are suspended in 200 μl PvuII buffer (50 mM Tris-HCl (pH 7.5), 60 mM NaCl and 6 mM MgCl₂). One unit of PvuII is added and the reaction mix is incubated for 5 minutes at 37° C. The enzyme is inactivated by heating 10 minutes at 65° C. 30 μl of 10×BamHI buffer (200 mM Tris-HCl (pH 8.0), 1M NaCl and 70 mM MgCl₂), 70 μl H₂O and 10 units of BamHI are next added and the reaction is incubated for 1 hour at 37° C. This is followed by the addition of 5 units of alkaline phosphatase and incubation for 1 hour at 65° C. The DNA fragments are separated on a 1 percent agarose gel, and a DNA fragment (FIG. 8) the size of a single cut fragment is purified.

A DNA linker with a blunt end and a BamHI end is synthesized in substantial accordance with the teaching of Example 28A4. This linker (shown at 118 in FIG. 8) has the following structure:

The linker is kinased and ligated into the BamHI-PvuII digested plasmid pNM789 in substantial accordance with the teaching of Example 28A2. This ligation mixture is used to transform *E. coli* K12 RV308 cells and plasmid isolation is performed upon these transformants in substantial accordance with the teaching of Example 28A3. Several plasmids are selected which contain the appropriate size PvuII fragment (494bp) and Xba I-BamHI fragment (628bp). The sequence of at least two of these is determined by sequencing from the BamHI site toward the unique SmaI site and one clone is selected with the desired sequence. This intermediate plasmid is designated plasmid 120. A schematic outline of this procedure and a restriction site and function map of plasmid 120 is presented in FIG. 8 of the accompanying drawings.

To isolate the EK-BGH-encoding DNA, about 10 μg of plasmid 120 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated and prepared for ligation in substantial accordance with the procedure of Example 28A6.

Figure 9:
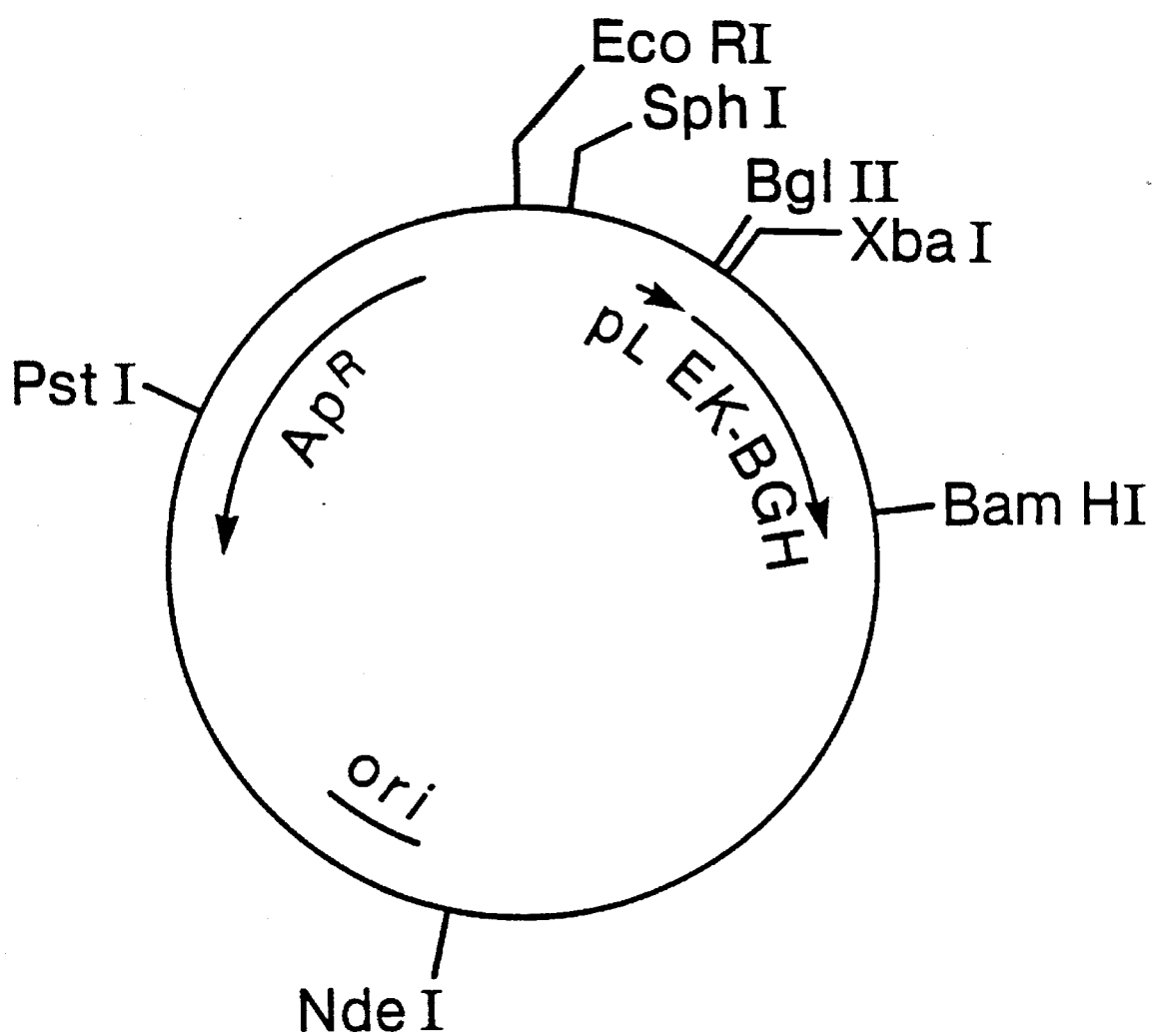
FIG. 9—A restriction site and function map of plasmid pL47.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid 120 in substantial accordance with the procedure of Example 28A2 to yield plasmid pL47. A restriction site and function map of plasmid pL47 is presented in FIG. 9 of the accompanying drawings. Plasmid pL47 was transformed into *E. coli* K12 MO(λ⁺) in substantial accordance with the procedure of Example 28A3, and the *E. coli* K12 MO(λ⁺)/pL47 transformants were identified. Plasmid pL47 DNA was prepared from the transformants in substantial accordance with the procedures of Example 28A1.

8. Construction of *E. coli* K12 RV308/pPR12AR1

Figure 10:
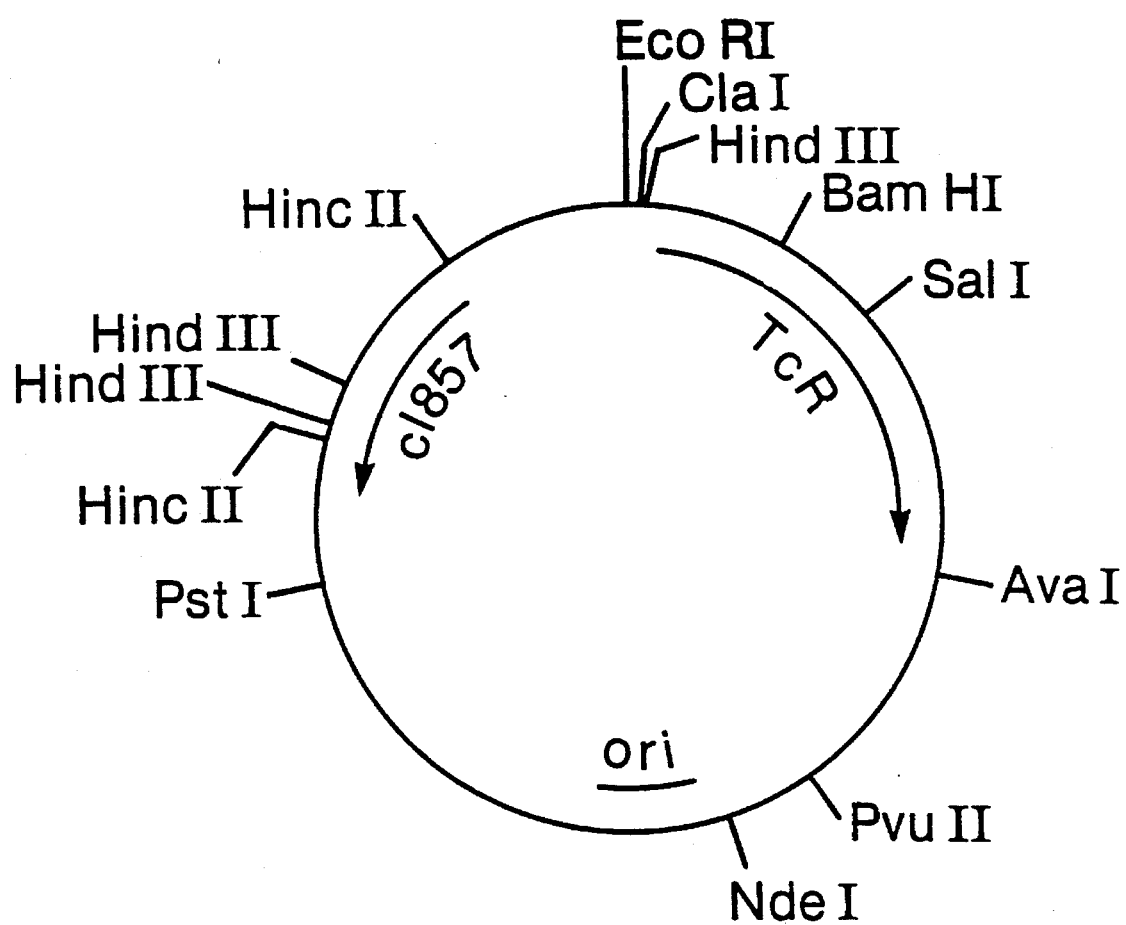
FIG. 10—A restriction site and function map of plasmid pPR12.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued 13 March 1984. A restriction site and function map of plasmid pPR12 is presented in FIG. 10 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and treated with Klenow in substantial accordance with the procedure of Example 28A5. After the Klenow reaction, the EcoRI-digested, Klenow-treated plasmid pPR12 DNA was recircularized by ligation in substantial accordance with the procedure of Example 28A2. The ligated DNA, which constituted the desired plasmid pPR12ΔR1, was used to transform *E. coli* K12 RV308 in substantial accordance with the procedure of Example 28A3, except that selection was based on tetracycline (5 μg/ml) resistance, not ampicillin resistance. *E. coli* K12 RV308 is available from the NRRL under the accession number NRRL B-15624. After the *E. coli* K12 RV308/pPR12ΔR1 transformants were identified, plasmid pPR12ΔR1 DNA was prepared from the transformants in substantial accordance with the procedure of Example 28A11.

Figure 11:
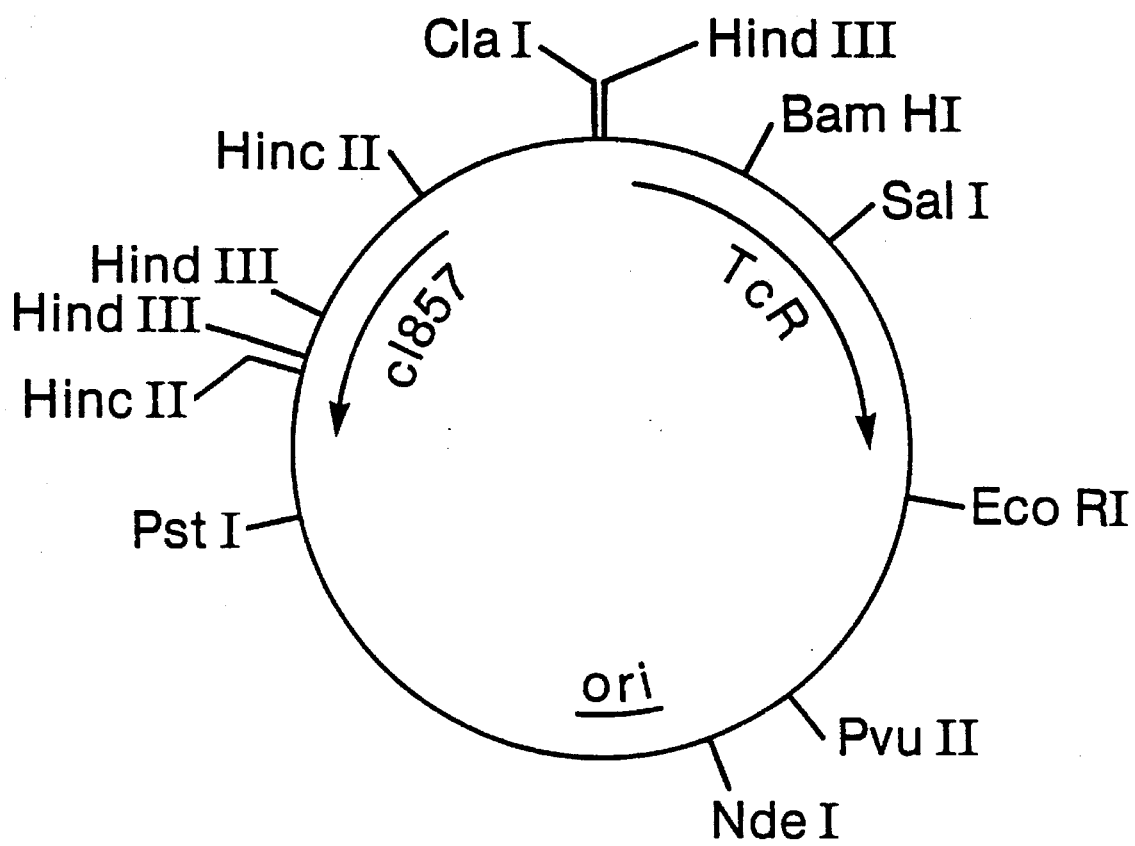
FIG. 11—A restriction site and function map of plasmid pPR12AR1.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 28A5. After the Klenow reaction, the AvaI-digested, Klenow-treated plasmid pPR12ΔR1 DNA was ligated to EcoRI linkers (5'-GAGGAATTCCTC-3') in substantial accordance with the procedure of Example 28A2. After the linker ligation, the DNA was precipitated and then resuspended in about 200 μl of high-salt buffer containing about 50 units of restriction enzyme EcoR1. The resulting reaction was incubated at 37° C. for about 2 hours. After the EcoR1 digestion, the reaction mixture was loaded onto an agarose gel, and the ~5.1 kb EcoR1 restriction fragment was purified in substantial accordance with the procedure of Example 29A6. The ~5.1 kb EcoR1 restriction fragment was recircularized by ligation in substantial accordance with the procedure of Example 28A2. The ligated DNA constituted the desired plasmid pPR12AR1. The plasmid pPR12AR1 DNA was transformed into *E. coli* K12 RV308 in substantial accordance with the procedure of Example 28A3, except that selection was based on tetracycline resistance, not ampicillin resistance. After identifying the *E. coli* K12 RV308/pPR12AR1 transformants, plasmid pPR12AR1 DNA was prepared in substantial accordance with the procedure of Example 28A1. A restriction site and function map of plasmid pPR12AR1 is presented in FIG. 11 of the accompanying drawings.

9. Construction of *E. coli* K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoR1 restriction fragment of plasmid pPR12AR1 was isolated and prepared for ligation in substantial accordance with the procedure of Example 28A6.

About 10 μg of plasmid pL47 were digested with restriction enzymes PStI and BamHI in 200 ul of high-salt buffer at 37° C. for two hours. The PstI-BamHI-digested DNA was loaded onto an agarose gel, and the ~2.7 kb PStI-BamHI restriction fragment that comprised the origin of replication and a portion of the ampicillin resistance-conferring gene was isolated and prepared for ligation in substantial accordance with the procedure of Example 28A6. In a separate reaction, about 10 ug of plasmid pL47 DNA were digested with restriction enzymes EcoRI and BamI in 200 ul of high-salt buffer at 37° C. for two hours, and the ~1.03 kb EcoRI-BamHI restriction fragment that comprised the novel transcriptional and translational activating sequence and the EK-BGH-encoding DNA was isolated and prepared for ligation in substantial accordance with the procedure of Example 28A6. The ~2 ug of the ~1.03 kb ECoRI-BamHI restriction fragment obtained were used in the construction of plasmid pL110.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 28A2 and 28A3, except that tetracycline resistance, not ampicillin resistance, was used as the basis for selecting transformants.

Figure 12:
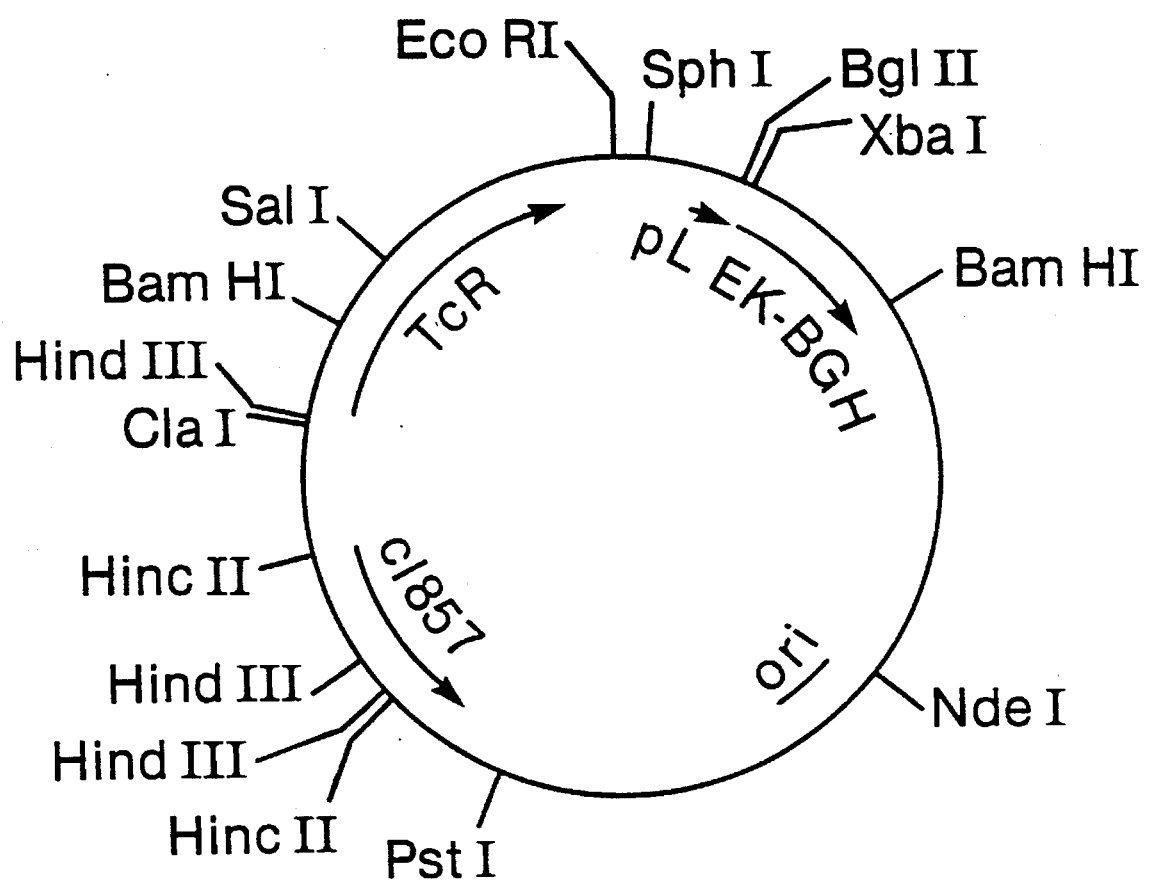
FIG. 12—A restriction site and function map of plasmid pL110.

Two PstI restriction enzyme recognition sites are present in the EK-BGH coding region that are not depicted in the restriction site and function maps presented in the accompanying drawings. A restriction site and function map of plasmid pL110 is presented in FIG. 12 of the accompanying drawings.

10. Construction of *E. coli* K12 RV308/pL110C a. Construction of *E. coli* K12 RV308/pL110A About 1 μg of plasmid pL110 DNA was digested with restriction enzyme NdeI in 20 μl total volume containing 2 μl of 10×high-salt buffer (1.0M NaCl; 0.50M Tris-HCl, pH=7.5; 0.10M MgCl$_2$; and 10 mM dithiothreitol) and 3 units of NdeI enzyme for 1 hour at 37° C. The reaction mixture was extracted with phenol/chloroform and the DNA precipitated with ethanol. The NdeI-digested plasmid pL110 DNA was dissolved in 50 μl of 1× Klenow buffer (40 mM KPO$_4$, pH=7.5; 6.6 mM MgCl$_2$; 1.0 mM 2-mercaptoethanol; 33 μM dATP; 33 μM dCTP; 33 μM dGTP; and 33 μM TTP). Two μl (~10 units, New England Biolabs) of the large fragment of *E. coli* DNA polymerase I, known as Klenow, were added to and mixed with the DNA, and the resulting reaction was incubated at 16° C. for 1 hour. The reaction was terminated by phenol extraction and the DNA conventionally purified. The NdeI-digested, Klenow-treated DNA was then ligated with T4 DNA ligase at 4° C. for 16 hours. The resulting DNA was used to conventionally transform *E. coli* K12 strain RV308 (NRRL B-15624). Transformants were selected on L-agar plates containing 100 μg/ml ampicillin and plasmids isolated from resistant colonies by the rapid alkaline extraction procedure described by Birnboim and Doly. A plasmid (pL110A in FIG. 13) lacking an NdeI site was selected.

b. Construction of Phage pL110B by Site-Specific Mutagenesis

Figure 13:
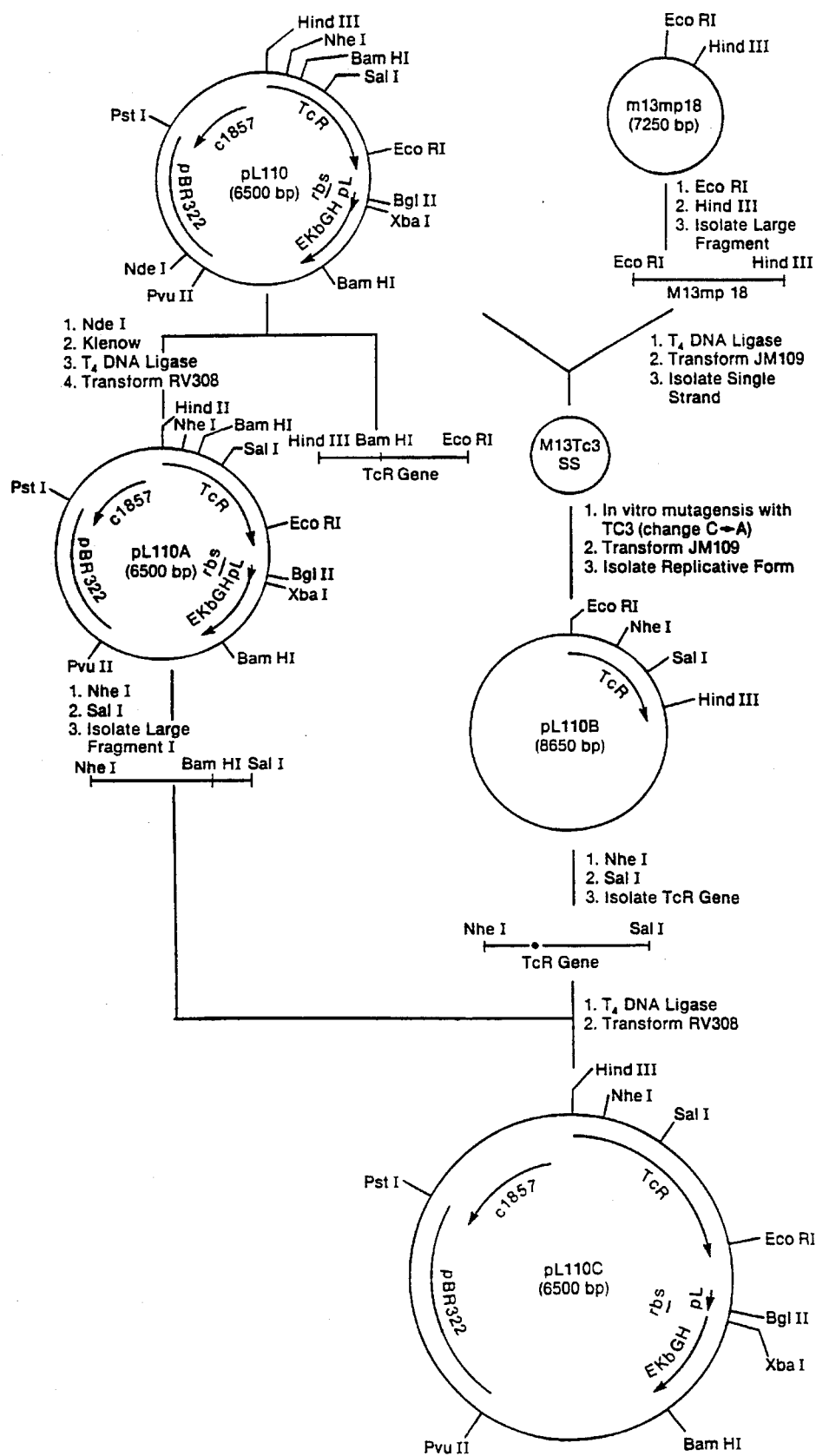
FIG. 13—A schematic outline of the construction of plasmid pL110C.

The protocol for eliminating the BamHI site in the tetracycline resistance-conferring gene by site-specific mutagenesis is shown on the right hand side of FIG. 13 of the accompanying drawings.

b(i) Construction of Phage M13Tc3

Plasmid pL110 served as the source of the tetracycline resistance-conferring gene. About 50 μg of plasmid pL110 in 50 μl of TE buffer were added to 25 μl of 10×HindIII buffer and 170 μl of H$_2$O. About 5 μl (~50 units) of restriction enzyme HindIII were added to the solution of plasmid pL110 DNA, and the resulting reaction was incubated at 37° C. for 2 hours. About 13 μl of 2M Tris.HCl, pH=7.4, and 5 μl (~50 units) of restriction enzyme EcoRI were added to the Hind-III-digested plasmid pL110 DNA, and the reaction was incubated for 2 more hours at 37° C. The reaction was stopped by extracting the reaction mixture with TE-saturated phenol; the phenol was removed by chloroform extractions.

The EcoRI-HindIII-digested plasmid pL110 DNA was then collected by precipitation and centrifugation, loaded into a 1% agarose gel, and the large ~4.3 kb EcoRI-HindIII restriction fragment was isolated and purified.

About 5 μg of phage m13mp18 (New England Biolabs) were dissolved in 50 μl of TE buffer and then digested with HindIII and EcoRI as described above. The HindIII-EcoRI-cut phage M13mp18 DNA was purified as described for pL110 except that an ~7.25 kb restriction fragment was isolated and purified.

About 100 nanograms of the ~4.3 kb HindIII-EcoRI fragment of plasmid pL110 were mixed with about 100 nanograms of the ~7.25 kb HindIII-EcoRI fragment of phage M13mp18, 2 μl of 10×ligase buffer, 1 μl (~100 units) of T4 DNA ligase, and 14 μl of H$_2$O. The ligation reaction was incubated at 15° C. for 1.5 hours; the ligated DNA constituted the desired phage m13Tc3 DNA. A restriction site and function map of phage m13Tc3 is presented in FIG. 13 of the accompanying drawings.

One ml of an overnight culture of E. coli K12 JM109 (E. coli K12 JM101, available from New England Biolabs, can be used instead of E. coli K12 JM109) was used to inoculate 50 ml of L broth, and the resulting culture was incubated at 37° C. with aeration until the O.D.$_{660}$ was between 0.3 and 0.4. The cells were resuspended in 25 ml of 10 mM NaCl, incubated on ice for 10 minutes, and collected by centrifugation. The cells were resuspended in 1.25 ml of 75 mM CaCl$_2$; a 200 μl aliquot of the cells was removed, added to 10 μl of the ligated DNA prepared above, and incubated on ice for about 40 minutes. The cell-DNA mixture was then incubated at 42° C. for 2 minutes, and varying aliquots (1, 10, and 100 μl) were removed and added to 3 ml of top agar (L broth with 0.5% agar kept molten at 45° C.) that also contained 50 μl of 2% X-Gal 50 μl of 100 mM IPTG, and 200 μl of E. coli K12 JM109 in logarithmic growth phase. The cell-top agar mixture was then plated on L-agar plates containing 40 μg/ml X-Gal (5-bromo-4-chloro-3-indolyl-β-D-thiogalactoside) and 0.1 mM IPTG (isopropyl-β-D-thiogalactoside), and the plates were incubated at 37° C. overnight.

The following morning, several clear, as opposed to blue, plaques were individually used to inoculate 2 ml of L broth, and the resulting cultures were incubated at 37° C. with aeration for 2 hours. The absence of blue color indicates the desired DNA insertion occurred. Then, the cultures were centrifuged, and 200 μl of the resulting supernatant were added to 10 ml cultures (O.D.$_{550}$=0.5) of E. coli K12 JM109 growing at 37° C. with aeration. These cultures were incubated for another 30 minutes at 37° C.; then, the cells were pelleted by centrifugation and used to prepare the replicative-form of the recombinant phage they contained. Double-stranded, replicative form phage DNA was isolated from the cells using a scaled-down version of the procedure described in Example 28A1. Transformants containing phage m13Tc3 DNA were identified by restriction enzyme analysis of their phage DNA.

b(ii) preparation of Single-Stranded Phage m13Tc3 DNA

One and one-half ml of an overnight culture of E. coli K12 JM109/m13Tc3 were centrifuged, and 100 μl of the phage m13Tc3-containing supernatant were used to inoculate a 25 ml culture of E. coli JM109 at an O.D.$_{660}$ of about 0.4–0.5. The culture was incubated for 6 hours at 37° C. with aeration, at which time the culture was centrifuged and the resulting supernatant, about 20 ml, transferred to a new tube. About 2 ml of a solution containing 20% polyethylene glycol (PEG) 6000 and 14.6% NaCl were added to the supernatant, which was then incubated on ice for 20 minutes.

The supernatant was centrifuged for 25 minutes at 7000 rpm, and the resulting pellet, which contained single-stranded phage m13Tc3 DNA, was resuspended in 500 μl of TE buffer. The DNA solution was extracted twice with TE-saturated phenol and twice with chloroform. The single-stranded DNA was then precipitated using NaOAc and ethanol and centrifuged. The resulting pellet was washed with 70% ethanol, dried, and then dissolved in 60 μl of H$_2$O.

b(iii) Mutagenesis

The single-stranded DNA fragment used in the mutagenesis was synthesized on an automated DNA synthesizer. The fragment has the sequence, 5'-CCCGTCCTGTG-GATACTCTACGCCGA-3', and is homologous to the region surrounding the BamHI site (5'-GGATCC-3') in the tetracycline resistance-conferring gene from plasmid pBR322, except that the A residue second from the 5' end (or third from the 3' end) is a C in plasmid pBR322. This change does not alter the amino acid composition of the tetracycline resistance-conferring protein but eliminates the BamHI site.

About 10 picomoles of the mutagenic primer and the M13 universal primer (Bethesda Research Laboratories (BRL), P.O. Box 6009, Gaithersburg, Md. 20760) were individually treated with 10 units (BRL) of T4 polynucleotide kinase in 20 μl of 1×kinase buffer (60 mM Tris-HCl, pH=7.8; 15 mM 2-mercaptoethanol; 10 mM MgCl$_2$; and 0.41 μM ATP) for 30 minutes at 37° C. The kinase-treated DNAs were used in the mutagenesis procedure described below.

The annealing reaction was carried out mixing together 300 nanograms (1.2 μl) of single-stranded phage m13Tc3, 1 picomole (2 μl) of the universal primer, 1 picomole (2 μl) of the mutagenic primer, 2 μl of 10× annealing buffer (100 mM Tris-HCl, pH=7.5; 1 mM EDTA; and 500 mM NaCl), and 12.8 μl of H$_2$O. The reaction was incubated at 80° C. for 2 minutes, at 50° C. for 5 minutes, and then allowed to cool to room temperature.

The extension reaction was carried out by adding 5 μl of 10×extension buffer (500 mM Tris-HCl, pH=8; 1 mM EDTA; and 120 mM MgCl$_2$); 5 μl of 2 mM dATP; 1 μl of a solution 6 mM in each of dGTP, TTP, and dCTP; 1 μl (~2 units, Pharmacia P-L Biochemicals, 800 Centennial Avenue, Piscataway, N.J. 08854) of Klenow enzyme; 1 μl (100 units) of T4 DNA ligase; and 17 μl of H$_2$O to the mixture of annealed DNA. The extension reaction was incubated at room temperature for 1 hour, then at 37° C. for 2.5 hours, and then overnight at 4° C.

The reaction was stopped by two extractions with TE-saturated phenol, which were followed by two extractions with CHCl$_3$. The DNA was precipitated with ethanol and NaOAc. The DNA was collected by centrifugation and resuspended in 50 μl of H$_2$O, and 6 μl of 10×S1 buffer were then added to the solution of DNA.

The solution of DNA was split equally into three tubes. About 200 units (Miles Laboratories) of S1 nuclease were added to two of the tubes. One S1 reaction was incubated at room temperature for 5 minutes, the other for 10 minutes. The reactions were stopped by extracting the reaction mixture twice with TE-saturated phenol. The phenol extractions were followed by two extractions with chloroform; then, the DNA was precipitated from the reaction mixture with NaOAc and ethanol. The untreated sample of DNA served as a negative control. The S1-treated samples were kept separate from each other throughout the remainder of the procedure but gave similar results.

The DNA pellets were resuspended in 20 μl of H$_2$O, and 10 μl of the resulting solution were used to transform E. coli K12 JM109 (E. coli K12 JM101 could also be used) in accordance with the procedure used during the construction of phage m13Tc3, except that no IPTG or X-Gal was added to the plates.

Double-stranded replicative form DNA from about 48 plaques was isolated as described above and screened for the presence of a BamHI restriction site. Isolates without a BamHI site were further screened by preparing single-stranded DNA as described above. The single-stranded DNA was sequenced using the dideoxy sequencing method (J. H. Smith, 1980, *Methods in Enzymology* 65: 560–580). The desired isolate was designated pL110B (FIG. 13).

c. Construction of Plasmid pL110C

About 50 μg of the replicative form of phage pL110B DNA were digested in 250 μl of 1×NheI buffer (50 mM NaCl; 6 mM Tris.HCl, pH=7.5; 6 mM $MgCl_2$; and 6 mM β-mercaptoethanol) containing ~50 units of NheI restriction enzyme at 37° C. for 2 hours. Five μl of 5M NaCl were then added to the NheI-digested phage pL110B DNA, followed by 5 μl (~50 units) of SalI restriction enzyme. Digestion was continued for 2 hours at 37° C. The desired ~422 bp NheI-SalI fragment containing the mutated region of the tetracycline resistance-conferring gene was then isolated from an acrylamide gel, according to well known standard procedures.

Plasmid pL110A DNA was digested with NheI and SalI under identical conditions, except that plasmid pL110A was substituted for phage pL110B. The ~6.1 kb NheI-SalI restriction fragment of plasmid pL110A was purified from agarose.

The desired plasmid pL110C was constructed by ligating together 100 nanograms each of the NheI-SalI fragments of pL110A (~6.1 kb) and pL110B (~422 bp) using conventional procedures. A restriction site and function map of plasmid pL110C is presented in FIG. 13 of the accompanying drawings. The desired plasmid pL110C confers tetracycline resistance to 10 μg/ml tetracycline in *E. coli* but lacks a BamHI site in the tetracycline resistance-conferring gene.

11. Construction of Plasmid pCZR111

Plasmid pL110C contains a single ClaI restriction site which was removed by running the following reactions. About 1 μg of plasmid pL110C was digested with ClaI in substantial accordance with the teaching of Example 28A2, except restriction enzyme ClaI and 10×ClaI Buffer (500 mM NaCl, 100 mM Tris-HCl (pH 7.9) and 100 mM $MgCl_2$) were used. The ClaI-digested DNA was then treated with Klenow in substantial accordance with the teaching of Example 28A5, except only dCTP, rather than all four dNTPs, was added.

The DNA was then precipitated and resuspended in 50 μl of Mung Bean Nuclease Buffer (50 mM Sodium Acetate (pH 5.0), 30 mM NaCl and 1 mM $ZnSO_4$). One unit of Mung Bean Nuclease (commercially available from New England Biolabs) was added and the reaction was incubated at 30° C. for 30 minutes. The tube was then placed in ice and NaCl was added to 0.2M, then the mixture was phenol/chloroform extracted, ethanol precipitated and resuspended in 10 mM Tris-HCl (pH 8.0). The DNA was then self-ligated and transformed into *E. coli* cells in substantial accordance with the teaching of Examples 28A3 and 28A4. The resultant plasmid was designated plasmid pCZR111.

12. Construction of Plasmid pCZR126S

About 26 ug of plasmid pCZR111 was digested with XbaI as follows. 10×XbaI buffer consists of 600 mM Tris-HCl, 100 mM $MgCl_2$, 1M NaCl, and 10 mM 2-mercaptoethanol, pH 7.5 (at 37° C.). 50 ul of 10×XbaI buffer, 15 ul of Xba I (10U/ul), and 185 ul of $H_2O$ were added to the 250 ul of water containing about 25 ug of plasmid pCZR111. The digestion proceeded at 37° C. for 1 hour. XbaI digested pCZR111 was then extracted in phenol, a 1/10 volume 3M $CH_3COO$-Na was added, 3 volumes of ethanol were added; the mixture was incubated in a dry ice-ethanol bath for 5 minutes, and then centrifuged. The precipitated DNA was resuspended in 50 ul $H_2O$.

The XbaI digested plasmid pCZR111 was digested with BamHI as follows. 0.2 ul of BamHI (10 U/ul), 10 ul of BamHI buffer (100mM Tris-HCl, 50mM $MgCl_2$, 1M NaCl, and 10mM 2-Mercaptoethanol, pH 8.0 [at 37° C.]), and 90 ul of $H_2O$ was added to the 50 ul of XbaI digested pL110 obtained hereinabove. The digest proceeded for 5 minutes at 37° C. The digested pCZR111 was extracted in phenol, a 1/10 volumes of $CH_3COONa+$ was added, followed by addition of 3 volumes of ethanol. Precipitated DNA was resuspended in 50 ul of 10mM Tris, 1 mM EDTA, pH 8.0 buffer.

The XbaI and BamHI digested pCZR111 was then loaded onto an agarose gel and the DNA band at about 5.8 kb was isolated. Plasmid pCZR126S was produced by ligating the ~5.8 kb fragment of pCZR111 to an XbaI to NdeI linker and a synthetic gene encoding EK-bovine growth hormone, which contains an NdeI site on its 5' end and a BamHI site on its 3' end. The XbaI to NdeI sequence was produced using standard oligonucleotide sequence methodology and consists of the following sequence:

```
5' CTAGAGGGTATTAATAATGTATATTGATTTTAATAAGGAGGAATAATCA 3'
   ||||||||||||||||||||||||||||||||||||||||||||||||
   TCCCATAATTATTACATATAACTAAAATTATTCCTCCTTATTAGTAT 5'
```

The above sequence was constructed by chemical synthesis of both strands, followed by mixing to allow hybridization. The gene encoding EK bGH was constructed from 16 chemically synthesized pieces of single-stranded DNA, ranging from 71 to 83 nucleotides long, which together comprise both complementary strands of the entire gene. The synthesis was done using an Applied Biosystems (ABS) machine and consists of the following sequence:

```
5'  TATGTTCCCATTGGATGATGATGATAAGTTCCCAGCCATGTCCTT
    |||||||||||||||||||||||||||||||||||||||||||||
    ACAAGGGTAACCTACTACTACTATTCAAGGGTCGGTACAGGAA

GTCCGGCCTGTTTGCCAACGCTGTGCTCCGGGCTCAGCACCTGCATCAGCTGGCTGCTGA
    ||||||||||||||||||||||||||||||||||||||||||||||||||||||||||||
    CAGGCCGGACAAACGGTTGCGACACGAGGCCCGAGTCGTGGACGTAGTCGACCGACGACT
```

```
CACCTTCAAAGAGTTTGAGCGCACCTACATCCCGGAGGGACAGAGATACTCCATCCAGAA
||||||||||||||||||||||||||||||||||||||||||||||||||||||||||||
GTGGAAGTTTCTCAAACTCGCGTGGATGTAGGGCCTCCCTGTCTCTATGAGGTAGGTCTT

CACCCAGGTTGCCTTCTGCTTCTCTGAAACCATCCCGGCCCCACGGGCAAGAATGAGGC
||||||||||||||||||||||||||||||||||||||||||||||||||||||||||
GTGGGTGCAACGGAAGACGAAGAGACTTTGGTAGGGCCGGGGGTGCCCGTTCTTACTCCG

CCAGCAGAAATCAGACTTGGAGCTGCTTCGCATCTCACTGCTCCTCATCCAGTCGTGGCT
||||||||||||||||||||||||||||||||||||||||||||||||||||||||||||
GGTCGTCTTTAGTCTGAACCTCGACGAAGCGTAGAGTGACGAGGAGTAGGTCAGCACCGA

TGGGCCCCTGCAGTTCCTCAGCAGAGTCTTCACCAACAGCTTGGTGTTTGGCACCTCGGA
||||||||||||||||||||||||||||||||||||||||||||||||||||||||||||
ACCCGGGGACGTCAAGGAGTCGTCTCAGAAGTGGTTGTCGAACCACAAACCGTGGAGCCT

CCGTGTCTATGAGAAGCTGAAGGACCTGGAGGAAGGCATCCTGGCCCTGATGCGGGAGCT
||||||||||||||||||||||||||||||||||||||||||||||||||||||||||||
GGCACAGATACTCTTCGACTTCCTGGACCTCCTTCCGTAGGACCGGGACTACGCCCTCGA

GGAAGATGGCACCCCCCGGGCTGGGCAGATCCTCAAGCAGACCTATGACAAATTTGACAC
||||||||||||||||||||||||||||||||||||||||||||||||||||||||||||
CCTTCTACCGTGGGGGGCCCGACCCGTCTAGGAGTTCGTCTGGATACTGTTTAAACTGTG

AAACATGCGCAGTGACGACGCGCTGCTCAAGAACTACGGTCTGCTCTCCTGCTTCCGGAA
||||||||||||||||||||||||||||||||||||||||||||||||||||||||||||
TTTGTACGCGTCACTGCTGCGCGACGAGTTCTTGATGCCAGACGAGAGGACGAAGGCCTT

GGACCTGCATAAGACGGAGACGTACCTGAGGGTCATGAAGTGCCGCCGCTTCGGGGAGGC
||||||||||||||||||||||||||||||||||||||||||||||||||||||||||||
CCTGGACGTATTCTGCCTCTGCATGGACTCCCAGTACTTCACGGCGGCGAAGCCCCTCCG

CAGCTGTGCCTTCTAG 3'
||||||||||||||||
GTCGACACGGAAGATCCTAG 5'
```

Figure 14:
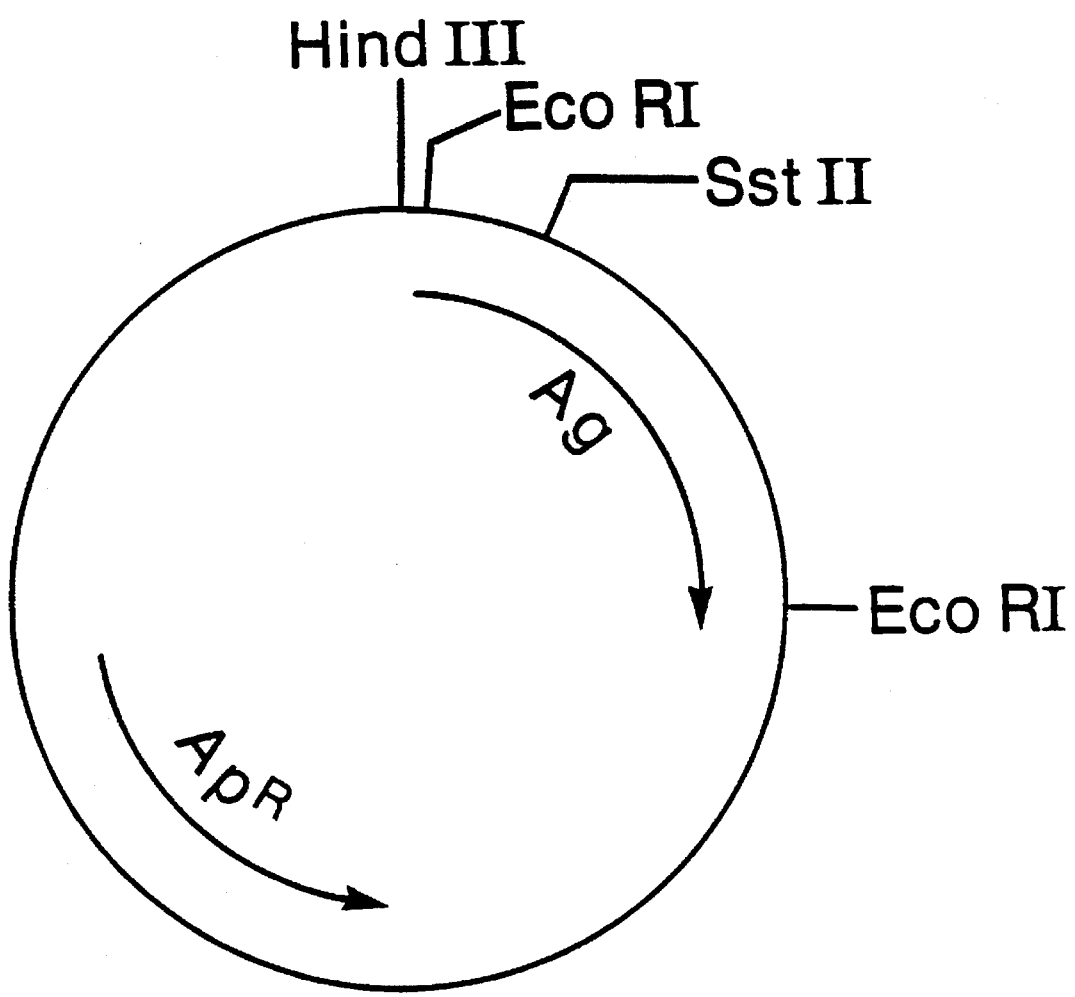
FIG. 14—A restriction site and function map of plasmid pCZR126S.

Construction of plasmid pCZR126S was accomplished by ligation of the following site components: ~0.28 ug of the 5.8 kb fragment obtained from plasmid pL110 after complete digestion with XbaI and partial digestion with BamHI in a total volume of 2 ul, ~0.18 ug of the synthetic gene encoding a bovine growth factor derivative which has a 5' termini corresponding to a XbaI site and a 3' termini corresponding to a BamHI site in a total volume of 2.5 ul, 8.75 picomoles of the chemically synthesized XbaI to NdeI linker in 1 ul. The plasmid components were added to 6 ul of 5×ligation buffer: 250 mM Tris-HCl, 50 mM MgCl$_2$, 5 mM ATP, 5 mM DTT, 25% v/v polyethylene glycol 8,000, pH 7.6, 2 ul of ligase, and 16.5 ul of H$_2$O. The ligation mixture was incubated overnight at 16° C. The circularized plasmid pCZR126S was then used to transform E. coli RV308 cells in substantial accord with the method of Example 28A3. A restriction site and function map of plasmid pCZR126S is presented in FIG. 14 of the accompanying drawings.

B. Construction of Human Proinsulin Expression Plasmid pRB172

1. Construction of plasmid pRB145

The human proinsulin gene was first custom synthesized and cloned into pUC18 plasmid (commercially available from BRL). The gene was synthesized using standard techniques and comprises the sequence:

```
         HindIII    NdeI                                              DraIII
           |         |                                                  |
    5'   AGCTTCAT  ATGTATTTTGTTAACCAACACCTGTGCGGCTCCCACCTG  GTGGAAGCTCT

AGTA   TACATAAAACAATTGGTTGTGGACACGCCGAGGGTGGAC  CACCTTCGAGA

GTACCTGGTGTGCGGTGAACGTGGCTTCTTCTACACCCCGAAGACCCGCCGTGAGGCA

CATGGACCACACGCCACTTGCACCGAAGAAGATGTGGGGCTTCTGGGCGGCACTCCGT

AvaII                                 XmaI
               |                                    |
         GAG  GACCTGCAGGTGGGTCAGGTGGAGCTGGGCGGTGGS  CCGGGTGCAGGCAGCCTGC

CTC  CTGGACGTCCACCCAGTCCACCTCGACCCGCCACCG  GGCCCACGTCCGTCGGACG

AGCCGCTGGCCCTGGAGGGGTTCCCTGCAGAAGCGTGGCATTGTGGAACAATGCTGTAC

TCGGCGACCGGGACCTCCCCAAGGGACGTCTTCGCACCGTAACACCTTGTTACGACATG

BamHI
                                                                  |
         CAGCATCTGCTCCCTGTACCAGCTGGAGAACTACTGCAACTAG  GATCCG          3'

GTCGTAGACGAGGGACATGGTCGACCTCTTGATGACGTTGATC  CTAGGCTTAA       5'
                                                                 |
                                                               EcoRI
```

One of the clones having the correct sequence was selected for the production of cesium chloride purified DNA. The plasmid was isolated by the standard procedure [see, for example, *Molecular Cloning, A Laboratory Manual*, (1982) ed. by Maniatis, T; Fritsch, E. F. and Sambrook, J., Cold Spring Harbour Laboratory Publications, New York the entire teaching of which is herein incorporated by reference]. About 6 µl (20 µg) of this plasmid DNA was added to 20 µl of 10×NdeI buffer (150 mm NaCl, 10 mM Tris-HCl (pH 7.8), 6 mM $MgCl_2$, 6 mM 2-mercaptoethanol, 100 µg/ml BSA), 5 µl NdeI restriction enzyme (~40 units) and 169 µl $H_2O$. After mixing, the reaction was incubated at 37° C. for 2 hours. The DNA was precipitated by making the mix 0.3M NaOAc, adding three volumes of ethanol, mixing and chilling to −70° C. and centrifuging. The DNA pellet was washed with 70% ethanol (1 ml), dried and dissolved in 20 µl of 10×BamHI buffer (150 mm NaCl, 6 mM Tris-HCl (pH 7.9), 6 mM $MgCl_2$, 100 µg/ml BSA), 2 µl of BamHI restriction enzyme (40 units) and 178 µl $H_2O$. After gentle mixing, the reaction was incubated at 37° C. for 2 hours. The DNA was again precipitated with three volumes of ethanol as above and electrophoresed on a 1% low melting agarose gel (FMC, sea plaque agarose). The desired DNA fragment corresponding to about 270 bp was sliced from the gel and then DNA was recovered by melting the agarose and passing through an Elutip-d column (Schleicher & Schuell, Keene, N. H.) according to the procedure recommended by the vendor. After precipitation and drying, the DNA was stored in 30 µl of 10 mM Tris-HCl pH 8.0.

About 15 µg of plasmid pCZR126S (from Example 28A12) was suspended in 20 µl of 10×NdeI buffer, 5 µl of NdeI restriction enzyme (40 units) and $H_2O$ (175 µl), gently mixed and incubated at 37° C. for 2 hours. After the incubation, the DNA was precipitated with three volumes of ethanol as above, dried and then resuspended in 20 µl of 10×BamHI buffer, 2 µl of BamHI restriction enzyme (40 units) and 178 µl water. After gentle mixing, the reaction was incubated at 37° C. for 2 hours. The DNA was again precipitated with three volumes of ethanol and electrophoresed on a 1% low-melting agarose gel. The larger fragment corresponding to the vector DNA was sliced from this gel and the DNA was recovered by the Elutip-d column procedure as described above. After precipitation and drying the vector DNA was stored in 35 µl of 10 mm Tris-HCl pH 8.0.

About 2.5 µl of the vector DNA was mixed with 12 µl of the purified human insulin gene fragment from above, 4 µl of 10 mM ATP, 0.5 µl of 1M dithiothreitol, 5 µl of 10×ligase buffer (500 mM Tris-HCl pH 7.6, and 100 mM $MgCl_2$), 26 µl of water and 0.5 µl of $T_4$ DNA Ligase (Pharmacia, 3.5 units). The reaction was incubated at 4° C. for 16 hours. The ligated mixture was diluted with 50 µl of 10 mM Tris-HCl (pH 7.6) and 3 µl of 1M $CaCl_2$ and then subsequently transformed into *E. coli* K12 RV308 in substantial accordance with the teaching of Example 28A3. The cells were plated on TY plates supplemented with 5 µg/ml tetracycline then incubated overnight at 32° C.

Figure 16:
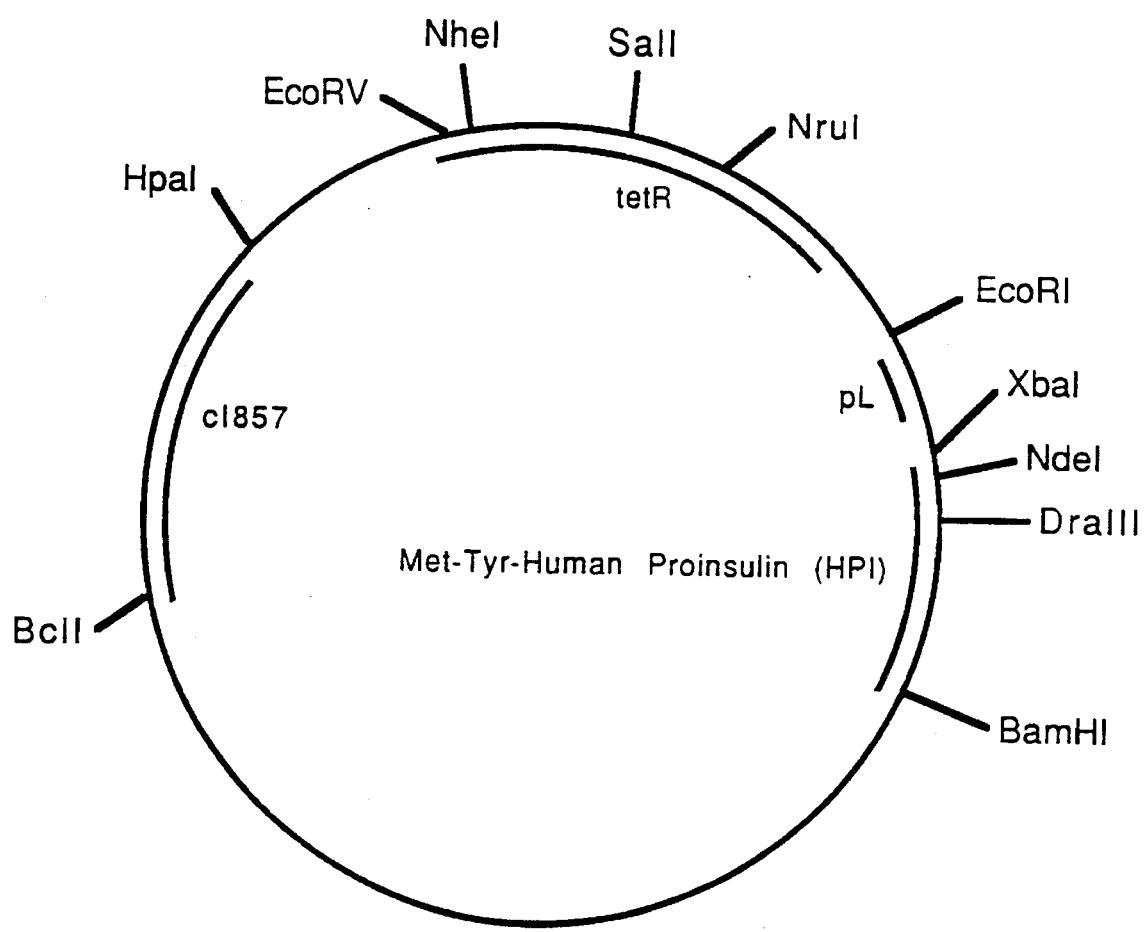
FIG. 16—A restriction site and function map of plasmid pRB145.

Plasmids from 3 mL cultures were isolated from tetracycline resistant colonies by the rapid alkaline extraction procedure described in Molecular Cloning, A Laboratory Manual (1982) ed. by Maniatis, T., Fritsch, E. F., and Sambrook, J., Cold Spring Harbor publications, New York, (pages 368–369). The presence of the correct human proinsulin gene fragment was found by miniscreen procedure using polyacrylamide gel electrophoresis to analyze the XbaI/BamHI digested fragment. Those plasmids with the correct size (about 315 bp) inserts were selected for amplification and purification. The plasmid containing the human proinsulin gene was pRB145. A restriction site and function map of plasmid pRB145 is presented in FIG. 16 of the accompanying drawings.

2. Construction of plasmid pRB164A

About 30 µg of plasmid pRB145 was suspended in 20 µl of 10×NdeI buffer, 5 µl of NdeI restriction enzyme (New England Biolabs, 40 units), and 175 µl $H_2O$ gently mixed and incubated at 37° C. for 1 hour. Two µl of BamHI restriction enzyme (New England Biolabs, 40 units) was then added to the reaction mixture and the incubation at 37° C. was continued for another 2 hours. The DNA was precipitated with three volumes of ethanol and 0.3M NaOAc and electrophoresed on a 1% low melting agarose gel. The smaller (about 270 bp) NdeI/BamHI restriction fragment encoding the human proinsulin gene was sliced from the gel and the DNA was recovered by passing through an Elutip-d column as described previously. After precipitation and drying, the DNA was stored in 30 µl of 10 mM Tris pH 8.0.

To this DNA (30 µl) was then added 20 µl of 10×AvaII buffer (50 mM NaCl, 6 mM Tris-HCl, pH 8.0, 10 mM $MgCl_2$, 6 mM 2-mercaptoethanol, 100 µg/ml BSA), 5 µl of AvaII restriction enzyme (New England Biolabs, 20 units), and 175 µl of $H_2O$. After gently mixing, this reaction was incubated at 37° C. for 2 hours. The DNA was precipitated with three volumes of ethanol and 3M NaOAc (20 µl) and then electrophoresed on a 1.2% low melting agarose gel. The larger AvaII/BamHI restriction fragment (about 156 bp) was sliced from the gel and then DNA was recovered by passing through an Elutip-d column as described above. After precipitation and drying, the DNA was stored in 30 µl of 10 mM tris pH 8.0.

The DNA (~115 bp) corresponding to the NdeI/AvaII restriction fragment of human proinsulin gene was synthetically prepared. The first step consisted of synthesis of four single stranded deoxyribooligonucleotides by the DNA synthesizer (Applied Biosystems, model 380B). The nucleotide sequences of these four oligonucleotides are 1. TATGCGTATGTTTGTTAACCAACACCTGTGCGGCTCCCACCTG
   GTGGAAGCTCTGTACCT     (60 mer)

2. GGTGTGCGGTGAACGTGGCTTCTTCTACACCAAGCCGACVC
   CGCCGTGAGGCAGAG     (55 mer)

3. CACCAGGTACAGAGCTTCCACCAGGTGGGAGCC
   GCACAGGTGTTGGTTAACAAACATACGCA     (62 mer)

4. GTCCTCTGCCTCACGGCGGGTCGGCTTGGTGTAGAA
   GAAGCCACGTTCACCGCA     (54 mer)

After purifying each oligonucleotide by polyacrylamide gel electrophoresis, oligonucleotides two and three were phosphorylated according to the teachings of Brown, E. L., Belagaje, R., Ryan, M. J., and Khorana, H. G. (1979) *Methods in Enzymology*, Ed. by Wu, R., Academic Press, N.Y. 68, 109–151 the entire teaching of which is herein incorporated by reference. The phosphorylated oligonucleotides two and three (~715 pmoles of each) were then mixed with oligonucleotides one and two (~860 pmoles), annealed and ligated in a buffer (200 μl) containing 50 mM Tris-HCl (pH 7.6), 10 mM MgCl$_2$, 10 mMDTT, 50 μM ATP and 20 units of T4 DNA ligase (Pharmacia) for 16 hours at 4° C. The ligation product was purified on a 15% polyacrylamide gel. The DNA was recovered from the gel slice electrophoretically followed by desalting on a Sephadex G-50 column. The yield of the desired ligated product was 485 pmoles.

About 100 pmoles of this DNA were phosphorylated in a buffer (50 μl) containing 50 mM Tris (pH 7.6), 10 mM MgCl$_2$, 10 mM DTT and ATP, as described in Brown, E. L. et al., (1979), *Methods in Enzymology* 68, 109–151 the teaching of which is herein incorporated by reference. After filtration through a column of Sephadex G-50, the DNA was stored in 50 μl of 10 mM Tris, pH 8.0.

Figure 17:
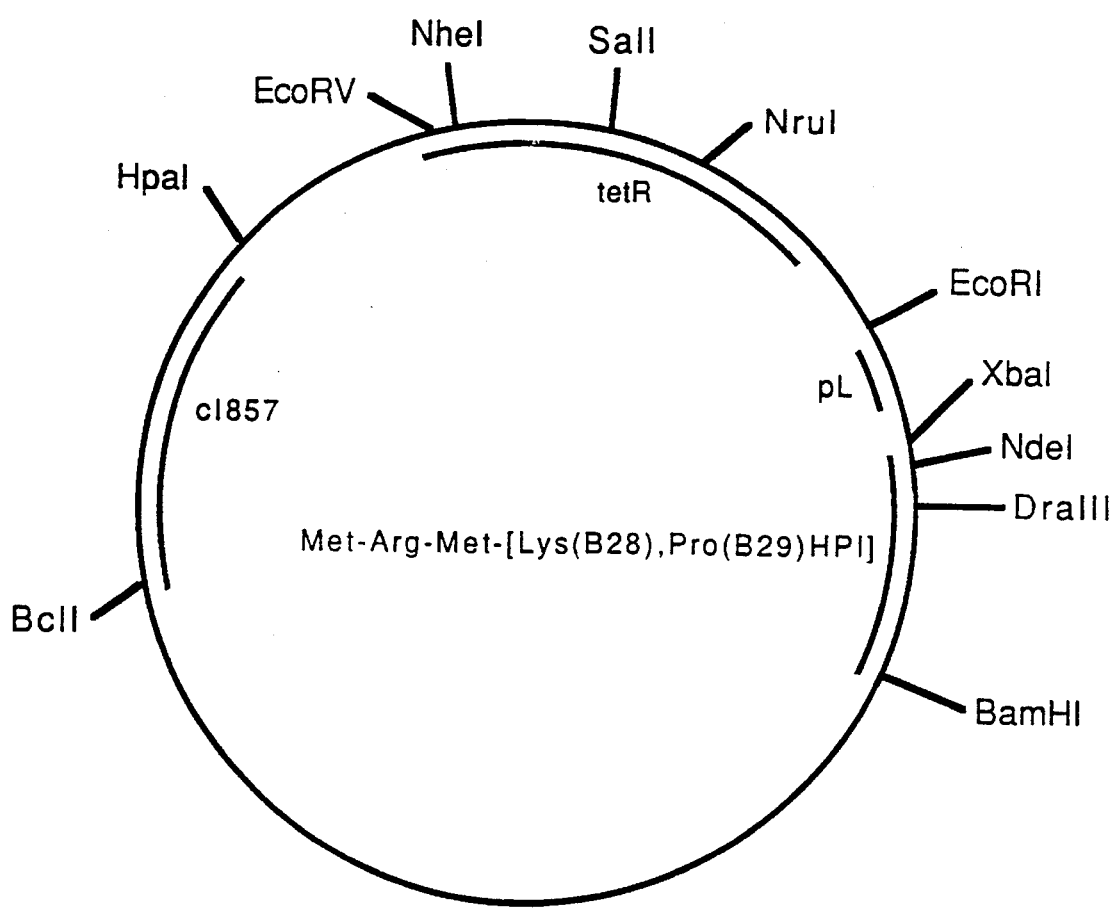
FIG. 17—A restriction site and function map of plasmid pRB164A.

About 2.5 μl of the vector DNA (NdeI-BamHI digested pCZR126S) was mixed with 18 μl of AvaII/BamHI restriction fragment from plasmid pRB145 and 10 μl (10 pmoles) NdeI/AvaII synthetic linker just constructed in a buffer (50 μl) containing 50 mM Tris (pH 7.6), 10 mM MgCl$_2$, 10 mMDTT, 800 μl ATP and 3.5 units of T$_4$ DNA ligase. The reaction was incubated at 4° C. overnight and then transformed into *E. coli* K12 RV308 in accordance with the procedure of Example 28A3. The desired transformant *E. coli* K12 RV308/pRB164A was identified by analysis of its plasmid DNA. The proper transformant was grown at 30° C. in TY media containing 5 μg/ml tetracycline to an O.D.$_{550}$ of about 0.2 (early log phase) and then shifted to 42° C. for 3 to 3.5 hours to induce the synthesis of the human proinsulin. The cells were pelleted and lysed by the addition of sample buffer (0.125M Tris-HCl (pH 6.8), 2% SDS, 30% glycerol, 1M 2-mercaptoethanol, 6M urea). Samples were heated to 97° C. for 2 minutes prior to loading on an acrylamide gel. Bands were easily visualized by staining with Coomassie Brilliant Blue dye. A scanning gel densitometer was used to quantitate the percentages of cell protein. A restriction site and function map of plasmid pRB164A is presented in FIG. 17 of the accompanying drawings.

3. Construction of plasmid pRB172

About 25 μg of plasmid pRB145 was suspended in 15 μl of 10×DraIII buffer (200 mM NaCl, 50 mM Tris-HCl (pH 7.5), 10 mM MgCl$_2$, 1 mM DTT, 10 μg/ml BSA) 6 μl of DraIII restriction enzyme (Boehringer Mannheim, 27 units) and 129 μl of H$_2$O, gently mixed and incubated at 37° C. for 6 hours. After the incubation, the DNA was precipitated, dried and resuspended in 10 μl of 10× XbaI buffer (150 mM NaCl, 6 mM Tris-HCl pH 7.9, 6 mM MgCl$_2$, 7 mM 2-mercaptoethanol, 100 μg/ml BSA), 3 μl of XbaI restriction enzyme (Boehringer Mannheim, 36 units) and 77 μl of H$_2$O. The reaction was gently mixed and incubated at 37° C. for 4 hours. The DNA was again precipitated with three volumes of ethanol and NaOAc and electrophoresed on a 1% low melting agarose gel. The lower band corresponding to the about 85 bp XbaI/DraIII restriction fragment of human proinsulin gene was sliced from the gel and the DNA was recovered by the Elutip-d column procedure. After precipitation and drying, the DNA was stored in 30 μl of 10 mM Tris pH 8.0.

About 15 μg of plasmid pRB164A was cut with the restriction enzyme DraIII and XbaI in accordance with the procedure described above. The upper band corresponding to the XbaI/DraIII vector fragment was isolated from the agarose gel by the Elutip-d column procedure. After precipitation and drying, the DNA was stored in 30 μl of 10 mM Tris pH 8.0.

About 5 μl of the XbaI/DraIII digested pRB164A vector DNA was mixed with 5 μl of the XbaI/DraIII restriction fragment from plasmid pBR145 in a buffer (50 μl) containing 50 mM Tris-HCl (pH 7.6), 10 mM MgCl$_2$, 10 mMDTT, 800 μM ATP and 6 units of T4 DNA ligase. The reaction was incubated at 4° C. overnight and used to transform *E. coli* K12/RV308 cells made competent by a standard CaCl$_2$ treatment.

Figure 18:
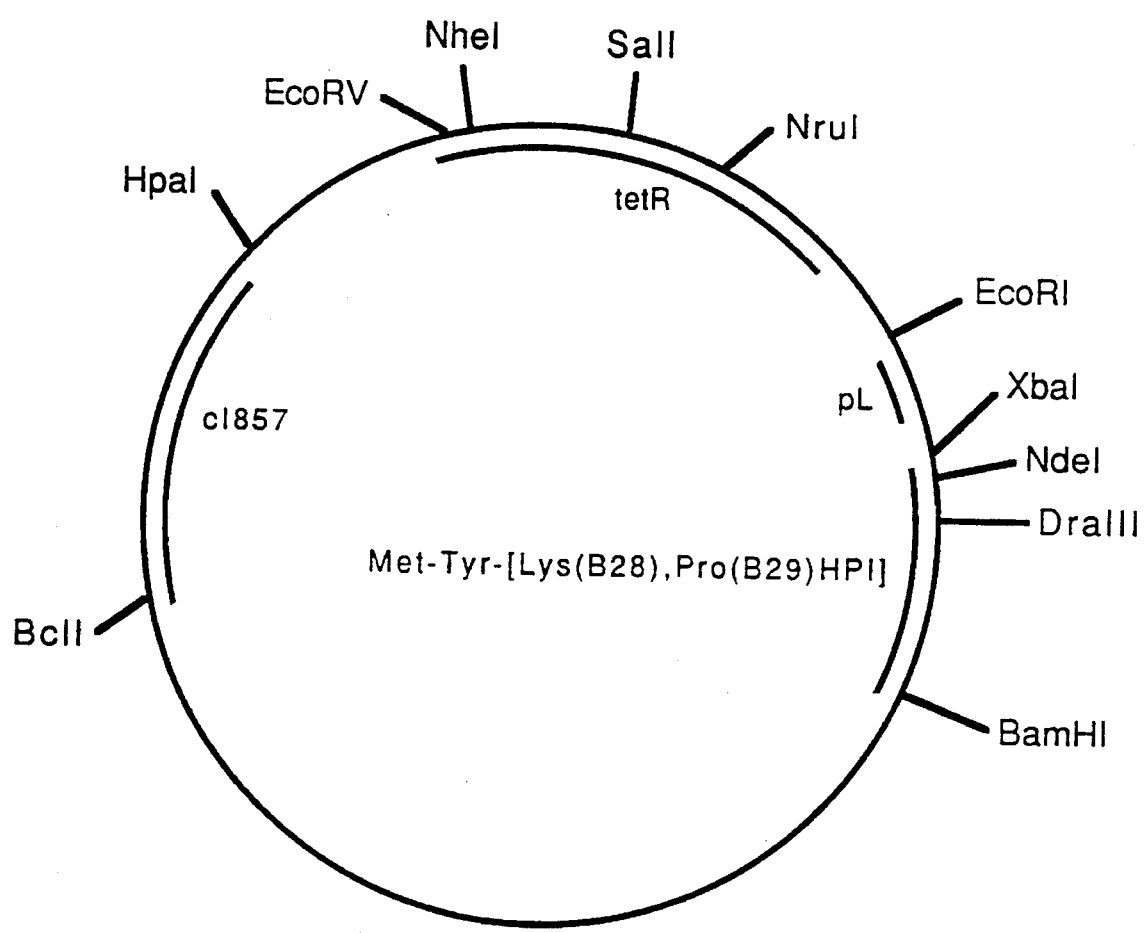
FIG. 18—A restriction site and function map of plasmid pRB172.

Transformants were selected on TY agar plates containing 5 μg/ml tetracycline. Plasmids were isolated from tetracycline resistant colonies by the rapid alkaline extraction procedure and analyzed by digestion with XbaI and BamHI restriction endonucleases. DNA from positive clones was sequenced using the sequenase system (U.S. Biochemicals). Those plasmids with the correct desired sequence were selected for amplification and purification. In this manner, the *E. coli* K12 RV308/pRB172 transformant was isolated. Expression and accumulation of human proinsulin harboring this plasmid was analyzed by visualization of the total cellular protein following electrophoretic separation in a 15% polyacylamide matrix. A restriction site and function map of plasmid pRB172 is presented in FIG. 18 of the accompanying drawings.

C. Construction of Escherichia coli RV308/pRB173 and pRB174

About 20 μg of plasmid pRB172 or pRB145 was suspended in 20 μl of 10×XbaI buffer (150 mm NaCl, 6 mM Tris-HCl, pH 7.9, 6 mM MgCl$_2$, 7 mM 2-mercaptoethanol, 100 μg/ml BSA) 2 μl of XbaI restriction enzyme (Boehringer Mannheim, 24 units) was added, gently mixed and incubated at 37° C. for 4 hours. After the incubation, the DNA was precipitated, dried and resuspended in 10 μl of 10×BamHI buffer (100 mM NaCl, 10 mM Tris-HCl (pH 8.0), 5 mM MgCl$_2$, 1 mM 2-mercaptoethanol, 100 μg/ml BSA), 5 μl of BamHI restriction enzyme Boehringer Manheim (40 units) and 75 μl of H$_2$O. The reaction was gently mixed and incubated at 37° C. for 4 hours. The DNA was again precipitated with ethanol and NaOAc and electrophoresed on a 1% low melting agarose gel. The about 320 bp XbaI/BamHI restriction fragment corresponding to the human proinsulin gene was isolated from the gel by the Elutip-d column procedure. After precipitation and drying, the DNA was resuspended in 20 μl of 10×XmaI buffer (25 mM NaCl, 10 mM Tris-HCl (pH 7.5), 10 mM MgCl$_2$, 10 mM 2-mercaptoethanol, 100 μg/ml BSA), 10 μl of XmaI restriction enzyme (New England Biolabs 10 units) and 170 μl of water. The reaction was gently mixed and incubated at 37° C. for 4 hours. After the incubation, the DNA was precipitated with ethanol and NaOAc and electrophoresed on a 1% low melting agarose gel. The larger DNA corresponding to the about 200 bp XbaI/XmaI restriction fragment was sliced from the gel and the DNA was recovered by the Elutip-d column as described before. The DNA was stored in 30 μl of 10 mM Tris pH 8.0.

The 51 bp DNA corresponding to an XmaI/BamHI restriction fragment of human proinsulin gene was constructed synthetically as follows. Two single stranded deoxyribooligonucleotides:

```
CCGGGTGCAGGCAGCCTGCAGCCGCTGGCCCTGGAGGGTTCCCTGCAGTAG      (51 mer)  and

GATCCTACTGCAGGGAACCCTCCAGGGCCAGCGGCTGCAGGCTGCCTGCAC      (51 mer)
``` were synthesized on an applied Biosystems DNA Synthesizer (model 380B) and purified by polyacylamide gel electrophoresis in presence of 7M urea. After isolation, the two oligonucleotides were phosphorylated according to the teachings from Brown, E. L., Belagaje, R., Ryan, M. J., and Khorana, H. G. (1979) *Methods in Enzymology*, Ed. by Wu, R., Academic Press, N.Y., 68, 109–151, and annealed to form the desired linker.

About 10 μg of plasmid pCZR126S (from Example 28A12) was suspended in 20 μl of 10×XbaI buffer (150 mM NaCl, 6 mM Tris-HCl (pH 7.9), 6 mM MgCl$_2$, 7 mM 2-mercaptoethanol, 100 μg/ml BSA) 2 μl of XbaI restriction enzyme (Boehringer Mannheim, 24 units) and 178 μl of water. The reaction was gently mixed and incubated at 37° C. for 2 hours. After this incubation, 4 μl of 5M NaCl and 2 μl of BamHI restriction enzyme (New England Biolabs, 20 units) were added, and the incubation was continued for another 2 hours at 37° C. The DNA was then precipitated with ethanol and NaOAc by the standard procedure and electrophoresed on a 1% low melting agarose gel. The upper band corresponding to XbaI/BamHI vector DNA was isolated with a Elutip-d column. After precipitation and drying, the DNA was stored in 30 μl of 10 mM Tris, pH 8.0.

Figure 19:
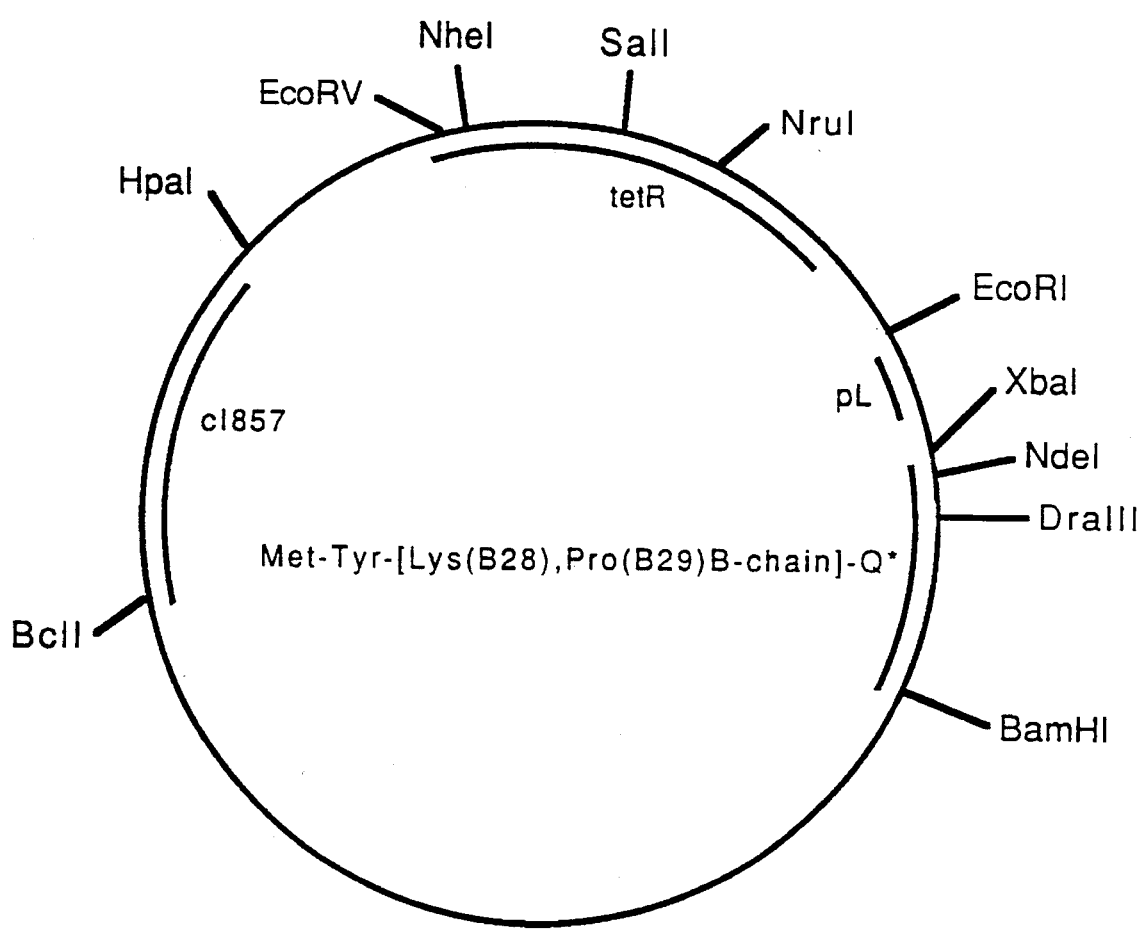
FIG. 19—A restriction site and function map of plasmid pRB173.

About 5 μl of the XbaI/BamHI-digested pCZR126S vector DNA was mixed with 10 μl of the XbaI/XmaI restriction fragment from pRB145 or pRB172 and 4 μl of the kinased XmaI/BamHI linker prepared above in a buffer (50 μl) containing 50 μM Tris (pH 7.6), 10 mM MgCl$_2$, 10 mMDTT, 800 μM ATP and 6 units of T$_4$ DNA ligase. The reaction was incubated at 4° C. overnight and used to transform *E. coli* K12 RV308 strain in accordance with the procedure of Example 28A3. The desired transformants, *E. coli* K12 RV308/pRB173 (if made from the pRB172 vector fragment) and *E. coli* K12 RV308/pRB174 (if made from the pRB145 vector fragment) were identified by analysis of their plasmid DNA and protein production before and after induction at 42° C. A restriction site and function map of plasmid pRB173 is presented in FIG. 19 of the accompanying drawings.

About 200 ng of plasmid DNA from the mini-prep were also transformed into *E. coli* L201 cells and the transformants were selected on 2×TY agar plates containing 15 μg/ml tetracycline. The proteins expressed by the transformants were analyzed and the desired transformants were confirmed by their production of human proinsulin. In this matter, *E. coli* L201/pRB173 and *E. coli* L201/pRB174 were isolated.

D. Construction of Escherichia coli K12 RV308/pRB175, pRB176, pRB177 and pRB178

About 12 μg of plasmid pRB172 was suspended in 15 μl of 10×NdeI buffer (100 mM NaCl, 50 mM Tris-HCl (pH 7.5), 10 mM MgCl$_2$, 1 mM DTT, 100 μg/ml BSA), 2.5 μl of NdeI restriction enzyme (20 units) and 133 μl of water. The reaction was gently mixed and incubated at 37° C. overnight. After the incubation, the DNA was precipitated with ethanol and NaOAc by the standard procedure, dried and resuspended in 15 μl of 10×DraIII buffer (50 mM Tris-HCl (pH 7.5), 200 mM NaCl, 10 mM MgCl$_2$, 1 mM DTT) 5 μl of DraIII restriction enzyme (20 units) and 130 μl of H$_2$O. After gently mixing, the reaction was incubated at 37° C. overnight. The DNA was again precipitated with ethanol and NaOAc as above and electrophoresed on a 1% low melting agarose. The desired larger restriction fragment was sliced from the gel and the DNA was recovered by the Elutip-d column procedure. The DNA was stored in 30 μl of 10 mM Tris HCl pH 8.0.

The following DNA linkers were chemically synthesized by the Applied Biosystems DNA Synthesizer (model 380B):

```
(i)    5' TATGTACGACCAACACCTGTGCGGCTCCCATCTG 3'

3'     ACATGCTGGTTGTGGACACGCCGAGGGTA   5'     for pRB175

(ii)   5' TATGTACGACGTTAACCAACACCTGTGCGGCTCCCATCTG 3'

3'     ACATGCTGCAATTGGTTGTGGACACGCCGAGGGTA   5'   for pRB176

(iii)  5' TATGTATAACCAACACCTGTGCGGCTCCCATCTG 3'

3'     ACATATTGGTTGTGGACACGCCGAGGGTA   5'      for pRB177

(iv)   5' TATGTACGTTAACCAACACCTGTGCGGCTCCCATCTG 3'

3'     ACATGCAATTGGTTGTGGACACGCCGAGGGTA   5'     for pRB178
```

After purifying each oligonucleotide by polyacrylamide gel electrophoresis, they were phosphorylated according to the teachings mentioned previously and annealed in order to facilitate the ligation and construction of the human proinsulin gene analog-encoding DNA fragments. The linkers (i) to (iv) were used to construct the plasmids pRB175, pRB176, pRB177 and pRB178 respectively.

Figure 20:
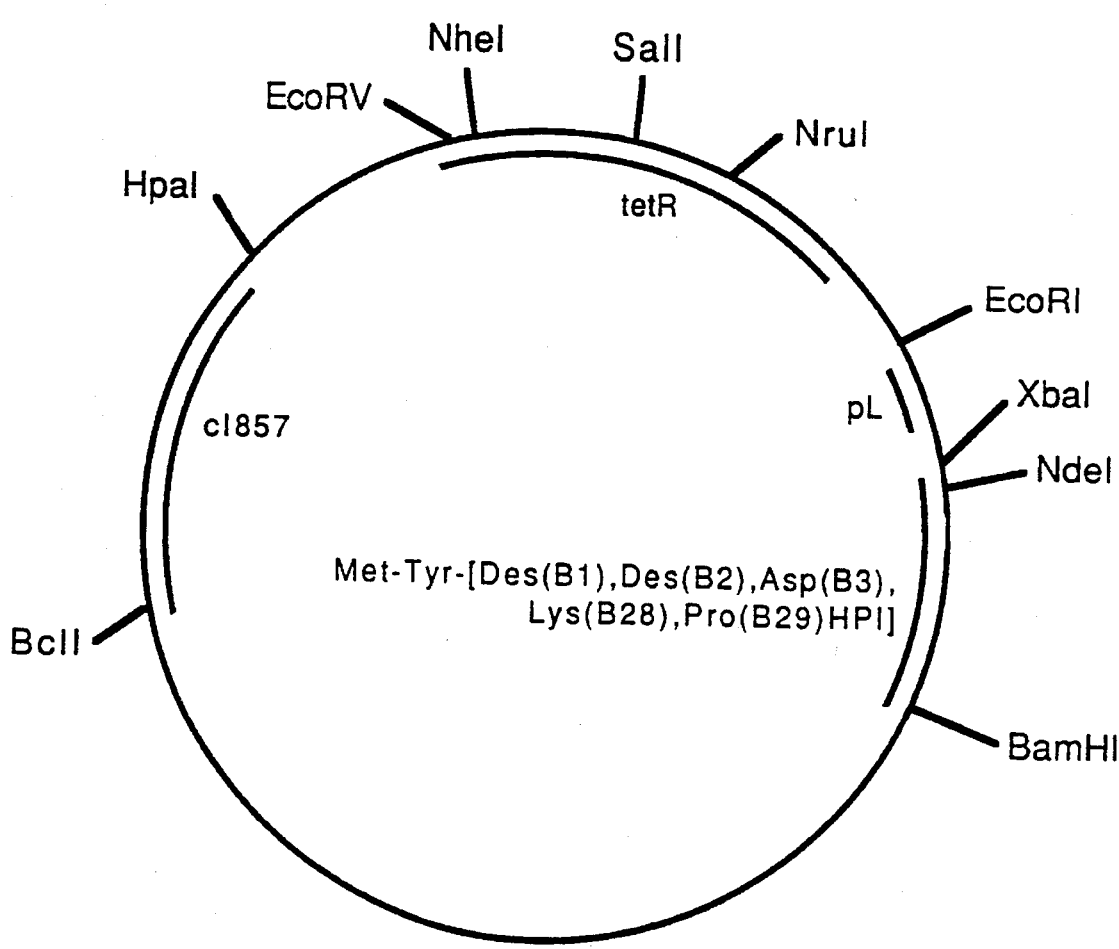
FIG. 20—A restriction site and function map of plasmid pRB175.

About 3 μl of the NdeI/DraIII-digested pRB172 vector DNA fragment was mixed with 4 μl of each of the separate kinased linkers (i-iv) in a buffer (50 μl) containing 50 μM Tris-HCl (pH 7.6), 10 mM MgCl$_2$, 10 mM DTT, 800 μM ATP and 6 units of T$_4$ DNA ligase. The reaction was incubated at 4° C. overnight and this mixture was used to transform *E. coli* K12 RV308 cells in accordance with the procedure of Example 28A3. The desired transformants, *E. coli* K12 RV308/pRB175, *E. coli* K12 RV308/pRB176, *E. coli* RV308/pRB177 and *E. coli* K12 RV308/pRB178 were identified by analysis of their plasmid DNA and protein production before and after induction of the cells at 42° C. A restriction site and function map of plasmid pRB175 is presented in FIG. 20 of the accompanying drawings.

TABLE I

Human Preinsulin Analogs

| Analog | Plasmid | % Protein |
| --- | --- | --- |
| Met-Tyr-Human Proinsulin (HPI) | pRB145 | 11.3 |
| Met-Arg-Met-[Lys(B28),Pro(B29)HPI] | pRB164A | 10.5 |
| Met-Tyr-[Lys(B28),Pro(B29)HPI] | pRB172 | 7.3 |
| Met-Tyr[Lys(B28),Pro(B29)B-chain]-Q* | pRB173 | ND |
| Met-Tyr-[B-chain]-Q* | pRB174 | ND |
| Met-Tyr-[Des(B1),Des(B2),Asp(B3), Lys(B28),Pro(B29)HPI] | pRB175 | 8.5 |
| Met-Tyr-[Asp(B1),Lys(B28), Pro(B29)HPI] | pRB176 | 9.3 |
| Met-Tyr-[Des(B1),Des(B2),Lys(B28), Pro(B29)HPI] | pRB177 | 9.4 |
| Met-Tyr-[Des(B1),Lys(B28), Pro(B29)HPI] | pRB178 | 8.5 |

*Q = -Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gla-Pro-Leu-Ala-Leu-Glu-Gly-Ser-Leu-Gln-;

E. A stock culture of *E. coli* K12 RV308/pRB172 was formed into a permanent stock culture in the following manner.

Isolated colonies are spotted on the following phenotype plates: L-agar+5 mcg./ml Tc (tetracycline), L-agar+Sm (streptomycin sulfate), M-9 medium agar (a salt based medium containing $MgSO_4$, thiamine, HYCASE, and glucose), and M-9 medium agar without glucose and with lactose. One L-agar/Tc plate is incubated at 42° C., and the remaining plates are incubated at 30° C. for 24 hours. A phenotypically correct colony selected from the 30° C. L-agar/Tc plate is used to inoculate a flask containing 50 ml L-broth (contains tryptone, yeast extract, NaCl, and glucose) plus 5 mcg./ml Tc medium. The flask is incubated at 30° C. with shaking for 7 hours. The material in the flask (1.2 ml) is dispensed into bio-freeze vials and frozen in vapor-phase liquid nitrogen. The material then is thawed, and 1 ml is used to inoculate a flask containing 50 ml of L-broth plus 5 mcg./ml Tc. The flask is incubated at 30° C. with shaking for 4 hours. Two flasks containing 500 ml of BG-7 medium (contains $MgSO_4$, thiamine, glucose, Tc, and trace salts) are inoculated with 1 ml each from the foregoing, and the flasks are incubated with shaking for 9 hours at 30° C.

A 150-liter fermenter containing 80 liters of medium (contains citric acid, ferrous ammonium sulfate, $K_2HPO_4$, $NH_4Cl$, $NaH_2PO_4$, $CaCl_2$, $MgSO_4$, glucose, and trace inorganic salts) is inoculated with 1 liter of the BG-7 medium broth from above. The fermenter is operated at 30° C. until the carbon dioxide evolution rate reaches 1.0 mM/l/min. At that point, 50 liters of broth are transferred to the production fermenter to provide the cell inoculum.

A 2500-liter fermenter containing 1500 liters of the same medium used in the 150-liter fermenter is operated at 30° C. until the carbon dioxide evolution rate reaches 1.0 mMol/l/min, and then the temperature is raised to 40C. Operation is continued for an additional 8 hours. The broth is then heat inactivated at 61° C. for 7 minutes. The following yield data were obtained from the heat inactivated broth: Cell Yield, 13.1 grams/l dry weight; Product Potency, 273 mcg. Desformylate/ml of broth; Specific Activity (e.g. grams product/gram of cell), 2.1 percent; Percent Formylated Product, 13 percent.

Fermentation broth is transferred into a stainless steel holding tank and the temperature maintained between 2° and 8° C. The whole broth is then centrifuged or filtered to collect the *E. coli* cells such that a solids dry weight of approximately 15 to 20 percent is obtained. The collected cell solids are reslurried in process water. The cells are then disrupted using high pressure homogenization or other suitable methods to achieve lysis of 90 to 99 percent of the cells. The homogenized slurry is diluted to 5 percent dry weight with process water. The pH of the diluted disrupted cell slurry is adjusted to between pH 7 and 10 by adding sodium hydroxide. The inclusion bodies (granules) are separated from the cell debris by differential centrifugation. The resulting concentrate is from 15 to 20 percent solids.

The inclusion bodies are solubilized at alkaline pH in the presence of cysteine and urea. These solubilized granules are subjected to cation exchange chromatography on SP Sepharose-superflow in order to resolve the mixed disulfide form of the proinsulin analog from the bulk of granular material.

The methionyl-tyrosine extension of the amino terminus of the proinsulin analog is removed by incubation with cathepsin C, a dipeptidylaminopeptidase. The cathepsin cleavage reaction is terminated by sulfitolysis with potassium tetrathionate and cysteine at pH 8.8. Following solvent-exchange across Sephadex G-25, the resulting S-sulphonate of the proinsulin analog is allowed to fold by incubation at pH 10.6 in the presence of cysteine. The folding process is quenched by adjusting the pH to 2.4. Properly folded proinsulin analog is resolved from improperly folded material as well as contaminants remaining from the cathepsin C cleavage step by hydrophobic interaction chromatography on SP20SS resin. This separation occurs across an acetone gradient so the organic solvent must be removed from the mainstream pool by evaporation before further processing.

Following evaporation of the organic solvent, properly folded proinsulin analog is incubated with trypsin and carboxypeptidase B. These enzymes excise the C peptide of the proinsulin analog and generate Lys(B28), Pro(B29) human insulin. The insulin analog is then further purified by cation exchange chromatography on S-Sepharose followed by high performance reverse phase chromatography on a 10 μm C-8 resin. Acetonitrile is removed from the reverse phase mainstream by solvent exchange across Sephadex G-25 and the resulting material is concentrated using a spiral wound ultrafiltration system. Concentrated material is subjected to size exclusion chromatography on Sephadex G-50 resin and lyophilized to dryness.

EXAMPLE 29

Asp(B10), Asp(B28), Pro(B29) Human Insulin

A. Preparation of Asp(B10), Asp(B28), Pro(B29) Human Insulin B-Chain.

An Applied Biosystems 430A peptide synthesizer (including software revision 1.4) was used to prepare a crude peptidyl resin. 0.5 Millimoles (mMol) of the starting solid phase resin (t-BOC-Thr(Bzl)OCH$_2$ Pam resin) was used (0.72 mMol/g×77 g). All amino acids used were BOC protected and, except for glutamic acid, aspartic acid, and histidine, all were used directly as received (i.e., in cartridges from Applied Biosystems, Inc.; each cartridge contained approximately 2 mmol of protected amino acid). Glutamic acid, aspartic acid, and histidine were obtained from commercial sources and transferred to cartridges such that each cartridge contained approximately 2 mmol of the desired protected amino acid. The crude peptidyl resin was dried under vacuum at room temperature for 5 hours and its weight compared to the starting weight to assure reasonable weight gain. A small portion of sample was submitted for amino acid analysis to ensure that the desired amino acids were added in the correct proportions.

The peptide was cleaved from the peptidyl resin and side-chain deprotected by stirring for approximately 1 hour at 0° C. in a solution of 10 parts (ml/g) HF (containing 5% v/v p-thiocresol and 5% v/v m-cresol) to 1 part peptidyl resin. After removal of most of the HF by vacuum the peptide was precipitated in ethyl ether. After several rinses with ethyl ether followed by vacuum filtration, the peptide was dissolved in approximately 200 ml of 8M guanidine HCl, pH 11, containing 0.1M tris, 35 mg/ml $Na_2SO_3$ and 25 mg/ml $Na_2S_4O_6$. The solution was adjusted to pH 8.8 with 5N NaOH and allowed to stir vigorously for 3 hours at room temperature.

The resulting S-sulfonated peptide solution was loaded onto a 5×215 cm column of Sephadex G-25 (coarse) at room temperature. The sample was eluted at 21 ml/min at room temperature using 50 mM ammonium bicarbonate. The effluent was monitored at 276 nm and a pool of the desired effluent, 1110 ml, was made, frozen and lyophilized.

B. Combination of Asp(B10), Asp(B28), Pro(B29) Human Insulin B-Chain with Human Insulin A-Chain.

The combination of the A and B Chains was accomplished by the procedure of Chance et al., supra. 3.37 g. of the recombinant DNA-derived A-chain S-sulfonate and 1.3 g of the synthetic Asp(B10), Asp(B28), Pro(B29) B-chain S-sulfonate were each dissolved in 337 ml and 67 ml, respectively, of 0.1M glycine buffer at ambient temperature, each adjusted to pH 10.5 with 5N NaOH and then cooled to 5° C. A dithiothreitol (DTT) solution at 15.5 mg/ml was prepared in 0.1M glycine buffer at ambient temperature, adjusted to pH 10.5 with 5N NaOH and then cooled to 5° C.

The A- and B-chain solutions were combined, then 29.3 ml of the DTT solution were quickly added ($SH/SSO_3^- = 1.05$). The reaction solution was stirred at 4° C. in a 1000 ml glass beaker for 21 hours at 4° C. Glacial acetic acid (100 ml) was added, and the solution was allowed to stand at 4° C. for one hour.

The resultant precipitated mixture was centrifuged for 30 minutes at 2000 rpm at 4° C. The supernatant was combined with 35 ml acetonitrile and further purified by reversed-phase HPLC (using a 2.12×30 cm DuPont C8 column eluted at room temperature, 2.6 ml/min., using a linear gradient of increasing acetonitrile in 0.1M $NaH_2PO_4$, pH 2.2). The effluent was monitored at 280 nm. Selected fractions were assayed by analytical HPLC and the desired fractions pooled and diluted two-fold with Milli-Q $H_2O$, then loaded onto a Vydac C18 HPLC column 2.2×25 cm) and eluted with a linear gradient of increasing acetonitrile in 0.5% aqueous TFA. The effluent was monitored at 280 nm. Selected fractions were assayed by analytical HPLC. The appropriate fractions were pooled and lyophilized giving a yield of 230 mg of the insulin analog of greater than 91% purity by reversed-phase HPLC. The structure was verified by amino acid analysis (Table II) and mass spectroscopy (MS).

MS: 5772.3 (Theory: 5772.4).

EXAMPLE 30

Asp(B10), Val (B28), Pro(B29) Human Insulin

The titled insulin analog was prepared by enzymatic semisynthesis (reverse proteolysis) per examples 2–7 and 9–26 using Asp(B10) des-octapeptide (B23-30) human insulin and synthetic octapeptide Gly-Phe-Phe-Tyr-Thr-Val-Pro-Thr. The octapeptide was prepared by solid-phase peptide synthesis whereas the Asp(B10) des-octapeptide human insulin was derived from Asp(B10) human proinsulin by a trypsin hydrolysis reaction that removed sequence 23–65. The Asp(B10) proinsulin analog was prepared according to the methods outlined in Example 28 except that instead of the linkers (i–iv) listed on page 89 the following linker was used:

The Asp(B10) des-octapeptide human insulin was prepared as follows: 700 ml (9.8 grams) of folded Asp(B10) human proinsulin, in a pH 2.5 glycine buffer, was adjusted to pH 10.2 by adding 25 ml of ammonium hydroxide with stirring. The pH was then quickly adjusted to 9.10 with the addition of 20 ml of concentrated hydrochloric acid. To this solution was added 7 ml of a calcium chloride solution in water (14.7 mg/ml) followed by 70 ml of a 14 mg/ml solution of porcine trypsin in water giving an enzyme to substrate ratio of about 1:10 on a weight basis. The tryptic hydrolysis reaction was mixed well, then stored at 25° C. for 17 hours, at which point the reaction was stopped by adding 160 ml of glacial acetic acid giving a final pH of 3.09. 105 ml of acetonitrile was then added.

For isolation and purification of the resulting Asp(B10) des-octapeptide human insulin, the tryptic digest solution was then pumped onto a 5.5×30 cm. C-18 Vydac HPLC column at 25° C. Two buffers were prepared for this chromatography step: buffer A, consisting of 10 parts acetonitrile and 90 parts of a 0.5% TFA (trifluoroacaetic acid) solution, and buffer B, consisting of 50 parts acetonitrile and 50 parts 0.5% TFA. After briefly washing with buffer A, a linear gradient from 0–20% buffer B was pumped through the column at 2.4 ml/min. for 16 hours followed by a linear gradient of 20–70% buffer B at 8 ml/min. for 8 hours. A major peak containing the Asp(B10) des-octapeptide human insulin eluted at about the 50% buffer B level. Fractions containing the present material based on analytical reverse-phase HPLC were combined and lyophilized. Final weight recovery was 5.5 grams with an HPLC purity of 93%. The authenticity of the Asp(B10) des-octapeptide (B23-30) human insulin was verified by amino acid analysis, mass spectroscopy, and $NH_2$-terminal analysis.

For the preparation of the titled insulin analog, 725 mg of Asp(B10) des-octapeptide human insulin and 700 mg of synthetic octapeptide Gly-Phe-Phe-Tyr-Thr-Val-Pro-Thr were combined in 24 ml of a solution containing one part dimethyl sulfoxide, two parts 1,4-butanediol, and one part 0.35M tris buffer at 37° C. (final pH ~7). Porcine trypsin (143 mg) was added. The solution was mixed well and stirred occasionally for 120 minutes at 37° C.

The reaction was stopped at this time by adding the mixture to 226 ml of 0.1N HCl. The entire solution was pumped onto a 21×250 mm C-8 Zorbax column, and the products were eluted in an acetonitrile gradient in 0.1M sodium monobasic phosphate, pH 2 buffer.

The appropriate fractions, as determined by analytical HPLC, were pooled, diluted ten-fold with water, and pumped onto a 25×300 mm C-18 Vydac column. The desalted protein was eluted from the column with an acetonitrile gradient in 0.5% trifluoroacetic acid. The fractions containing the purified insulin analog were pooled and lyophilized to yield 133 mg. This sample was dissolved in 30 ml of 1M acetic acid and gel filtered on a 5×200 cm column of Sephadex G-50 (Superfine) eluted with 1M acetic acid at 4° C. and monitored at 276 nm. The main peak was lyophilized yielding approximately 115 mg of purified product. The structure was verified by amino acid analysis (Table II) and mass spectroscopy (MS).

MS: 5756.4 (Theory: 5756.4).

EXAMPLE 31

Asp(B10), Glu(B28), Pro(B29) Human Insulin

The titled insulin analog was prepared by enzymatic semisynthesis (reverse proteolysis) per Examples 2–7, 9–26 and 30 using Asp(B10) des-octapeptide (B23-30) human insulin and synthetic octapeptide Gly-Phe-Phe-Tyr-Thr-Glu-Pro-Thr. The octapeptide was prepared by solid-phase peptide synthesis whereas the Asp(B10) des-octapeptide human insulin was derived from Asp(B10) human proinsulin by a trypsin hydrolysis reaction that removed sequence 23–65 as described in Example 30.

For preparation of the titled insulin analog, 450 mg of Asp(B10) des-octapeptide human insulin and 450 mg of synthetic octapeptide Gly-Phe-Phe-Tyr-Thr-Glu-Pro-Thr were combined in 15 ml of a solution containing one part dimethylsulfoxide, two parts 1,4-butanediol, and one part 0.35M tris buffer at 37° C. (pH not adjusted). Porcine trypsin (90 mg) was added. The solution was mixed well and stirred occasionally for 150 minutes at 37° C. The proteins were precipitated by cold acetone, washed with diethyl ether, dried with a stream of nitrogen, and dissolved in about 50 ml 0.01N HCl containing enough guanidine. HCl to facilitate dissolution. This sample solution was gel filtered on a 5×200 cm column of Sephadex G-50 (Superfine) eluted with 1M acetic acid at 4° C. The effluent was monitored at 276 nm and by reverse-phase HPLC. Fractions containing the titled product were pooled (~200 ml), diluted to 500 ml with water, pumped onto a 21×250 mm C-8 Zorbax column, and the products eluted in an acetonitrile gradient in 0.1M sodium phosphate, pH 2 buffer. The appropriate fractions containing the titled insulin analog, as determined by analytical HPLC, were pooled, diluted five-fold with water, and pumped onto a 25× 300 mm C-18 Vydac column. The desalted protein was eluted with an acetonitrile gradient in 0.5% trifluoroacetic acid. Fractions containing the purified insulin analog were pooled and lyophilized to yield 72 mg. The structure was verified by amino acid analysis (Table II) and mass spectroscopy (MS).

MS: 5786.3 (Theory: 5786.4)

EXAMPLE 32

Asp(B10), Gln(B28), Pro(B29) Human Insulin

The titled insulin analog was prepared by enzymatic semisynthesis (reverse proteolysis) per Examples 2–7, 9–26, 30 and 31 using Asp(B10) des-octapeptide (B23-30) human insulin and synthetic octapeptide Gly-Phe-Phe-Tyr-Thr-Gln-Pro-Thr. The octapeptide was prepared by solid-phase peptide synthesis whereas the Asp(B10) des-octapeptide human insulin was derived from Asp(B10) human proinsulin by a trypsin hydrolysis reaction that removed sequence 23–65 as described in Example 30.

For preparation of the titled insulin analog, 450 mg of Asp(B10) des-octapeptide human insulin and 450 mg of synthetic octapeptide Gly-Phe-Phe-Tyr-Thr-Gln-Pro-Thr were combined in 15 ml of a solution containing one part dimethyl sulfoxide, two parts 1,4-butanediol, and one part 0.35M tris buffer at 37° C. (pH not adjusted). Porcine trypsin (90 mg) was added. The solution was mixed well and stirred occasionally for 150 minutes at 37° C. The proteins were precipitated by cold acetone, washed with diethyl ether, dried with a stream of nitrogen, and dissolved in about 80 ml 0.01N HCl containing enough guanidine. HCl to facilitate dissolution. This sample solution was gel filtered on a 5×200 cm column of Sephadex G-50 (Superfine) and eluted with 1M acetic acid at 4° C. The effluent was monitored at 276 nm and by reverse-phase HPLC. Fractions containing the titled product were pooled (~210 ml), diluted to 250 ml with water, pumped onto a 21×250 mm C-8 Zorbax column, and the products eluted in an acetonitrile gradient in 0.1M sodium phosphate, pH 2 buffer. The appropriate fractions containing the titled insulin analog, as determined by analytical HPLC, were pooled, diluted three-fold with water, and pumped onto a 25×300 mm C-18 Vydac column. The desalted protein was eluted with an acetonitrile gradient in 0.5% trifluoroacetic acid. Fractions containing the purified insulin analog were pooled and lyophilized to yield 77 mg. The structure was verified by amino acid analysis (Table II) and mass spectroscopy (MS).

MS: 5785.9 (Theory: 5785.4)

In Table II following are provided the amino acid analyses of compounds of the foregoing examples.

TABLE II

| Amino Acid Analysis on Human Insulin Analogs[1,2] | | | | | | | | | |
|---|---|---|---|---|---|---|---|---|---|
| | Example No. | | | | | | | | |
| | 2 | 3 | 4 | 5 | 6 | 7 | 8 | 9 | 10 |
| Amino Acid Residue | | | | | | | | | |
| Asp | 3.00(3) | 3.00(3) | 3.00(3) | 3.00(3) | 4.00(4) | 4.00(4) | 4.00(4) | 3.00(3) | 3.00(3) |
| Thr | 2.82(3) | 2.81(3) | 2.64(3) | 2.80(3) | 2.80(3) | 2.94(3) | 2.81(3) | 2.71(3) | 2.73(3) |
| Ser | 2.76(3) | 2.73(3) | 2.70(3) | 2.75(3) | 2.71(3) | 2.46(3) | 2.71(3) | 2.74(3) | 2.72(3) |
| Glu | 7.16(7) | 7.05(7) | 6.93(7) | 7.08(7) | 7.01(7) | 6.69(7) | 7.18(7) | 6.99(7) | 7.94(8) |
| Pro | 1.02(1) | 1.11(1) | 0.92(1) | 0.98(1) | 1.01(1) | 0.98(1) | 1.02(1) | 1.09(1) | 0.98(1) |
| Gly | 3.93(4) | 4.00(4) | 3.85(4) | 3.99(4) | 4.02(4) | 3.97(4) | 4.01(4) | 3.95(4) | 3.90(4) |
| Ala | 1.01(1) | 1.04(1) | 1.93(2) | 1.02(1) | 1.05(1) | 1.05(1) | 1.03(1) | 1.03(1) | 1.02(1) |
| Cys(1/2) | 5.13(6) | —(6)[3] | 5.13(6) | 5.17(6) | 5.32(6) | 4.91(6) | 5.53(6) | 5.23(6) | 5.33(6) |
| Val | 3.45(4) | 3.44(4) | 3.49(4) | 3.51(4) | 3.41(4) | 3.67(4) | 3.54(4) | 3.45(4) | 3.48(4) |
| Ile | 1.47(2) | 1.47(2) | 1.49(2) | 1.58(2) | 1.44(2) | 1.65(2) | 1.68(2) | 1.48(2) | 1.47(2) |
| Leu | 6.04(6) | 6.01(6) | 5.86(6) | 6.19(6) | 6.06(6) | 5.67(6) | 5.99(6) | 6.02(6) | 5.98(6) |
| Tyr | 3.83(4) | 3.74(4) | 3.52(4) | 4.19(4) | 3.90(4) | 3.55(4) | 3.82(4) | 3.73(4) | 3.58(4) |
| Phe | 2.84(3) | 2.85(3) | 2.64(3) | 2.85(3) | 2.84(3) | 3.02(3) | 2.86(3) | 2.72(3) | 2.73(3) |

TABLE II-continued

Amino Acid Analysis on Human Insulin Analogs[1,2]

| | | | | | | | | | |
|---|---|---|---|---|---|---|---|---|---|
| His | 2.35(2) | 2.10(2) | 2.02(2) | 2.14(2) | 1.60(2) | 2.09(2) | 1.07(1) | 2.02(2) | 2.10(2) |
| Lys | 0.97(1) | | | | | | 0.97(1) | | |
| Arg | 0.99(1) | 0.90(1) | 0.88(1) | 1.96(2) | 0.91(1) | 0.81(1) | 0.91(1) | 0.89(1) | 0.98(1) |
| Aba | | —(1)[3] | | | | | | | |
| Cya | | | | | | | | 0.90(1) | |
| Nle | | | | | | | | | |
| Orn | | | | | | | | | |
| Nva | | | | | | | | | |
| Met | | | | | | | | | |
| Trp | | | | | | | | | |

| | Example No. | | | | | | | |
|---|---|---|---|---|---|---|---|---|
| | 11 | 12 | 13 | 14 | 15 | 16 | 17 | 18 |
| Amino Acid Residue | | | | | | | | |
| Asp | 3.00(3) | 3.00(3) | 3.00(3) | 3.00(3) | 3.00(3) | 3.00(3) | 3.00(3) | 3.00(3) |
| Thr | 2.76(3) | 3.59(3) | 2.80(3) | 2.80(3) | 2.70(3) | 2.83(3) | 3.03(3) | 2.80(3) |
| Ser | 2.69(3) | 2.64(3) | 2.43(3) | 2.78(3) | 2.87(3) | 2.78(3) | 2.68(3) | 2.72(3) |
| Glu | 8.04(8) | 6.84(7) | 6.89(7) | 7.09(7) | 7.04(7) | 7.08(7) | 6.99(7) | 7.01(7) |
| Pro | 1.11(1) | 1.48(1) | 1.09(1) | 1.12(1) | 0.93(1) | 1.16(1) | 1.14(1) | 1.02(1) |
| Gly | 4.04(4) | 5.70(5) | 3.89(4) | 4.03(4) | 3.98(4) | 4.00(4) | 4.08(4) | 3.92(4) |
| Ala | 1.05(1) | 1.14(1) | 1.04(1) | 1.05(1) | 1.08(1) | 1.04(1) | 1.07(1) | 1.03(1) |
| Cys(1/2) | 5.26(6) | 4.54(6) | 4.57(6) | 5.19(6) | 5.00(6) | 4.75(6) | 4.82(6) | 5.30(6) |
| Val | 3.60(4) | 3.52(4) | 3.58(4) | 3.43(4) | 3.41(4) | 3.51(4) | 3.63(4) | 3.51(4) |
| Ile | 1.62(2) | 1.82(2) | 1.70(2) | 2.36(3) | 1.44(2) | 1.51(2) | 1.75(2) | 1.55(2) |
| Leu | 5.99(6) | 5.79(6) | 5.95(6) | 5.98(6) | 6.89(7) | 6.10(6) | 5.98(6) | 6.11(6) |
| Tyr | 3.73(4) | 3.89(4) | 3.75(4) | 3.74(4) | 3.64(4) | 3.86(4) | 3.80(4) | 3.84(4) |
| Phe | 2.88(3) | 3.47(3) | 3.01(3) | 2.85(3) | 2.71(3) | 2.86(3) | 3.13(3) | 2.89(3) |
| His | 2.08(2) | 2.24(2) | 3.39(3) | 2.07(2) | 2.30(2) | 2.48(2) | 2.29(2) | 2.10(2) |
| Lys | | | | | | | | |
| Arg | 0.91(1) | 0.80(1) | 0.95(1) | 0.89(1) | 0.86(1) | 1.00(1) | 0.80(1) | 1.03(1) |
| Aba | | | | | | | | |
| Cya | | | | | | | | |
| Nle | | | | | | 0.93(1) | | |
| Orn | | | | | | | | 0.96(1) |
| Nva | | | | | | | | |
| Met | | | | | | | 0.98(1) | |
| Trp | | | | | | | | |

| | Example No. | | | | | | | | | |
|---|---|---|---|---|---|---|---|---|---|---|
| | 19 | 20 | 21 | 22 | 23 | 24 | 25 | 26 | 27 | 28 |
| Amino Acid Residue | | | | | | | | | | |
| Asp | 3.00(3) | 3.00(3) | 3.00(3) | 3.00(3) | 3.00(3) | 3.00(3) | 3.00(3) | 3.00(3) | 5.00(5) | 4.00(4) |
| Thr | 2.51(3) | 3.04(3) | 2.76(3) | 3.73(4) | 2.70(3) | 2.80(3) | 3.16(3) | 2.75(3) | 2.75(3) | 2.74(3) |
| Ser | 2.55(3) | 2.69(3) | 3.60(4) | 2.74(3) | 2.76(3) | 2.78(3) | 2.75(3) | 2.63(3) | 2.50(3) | 2.62(3) |
| Glu | 7.25(7) | 7.06(7) | 6.99(7) | 7.07(7) | 7.01(7) | 7.04(7) | 6.98(7) | 7.02(7) | 7.02(7) | 7.05(7) |
| Pro | 0.93(1) | 2.20(2) | 0.95(1) | 1.00(1) | 0.95(1) | 1.11(1) | 1.22(1) | 1.16(1) | 0.91(1) | 1.15(1) |
| Gly | 3.92(4) | 3.93(4) | 3.91(4) | 3.97(4) | 3.94(4) | 3.97(4) | 4.26(4) | 3.98(4) | 4.07(4) | 4.08(4) |
| Ala | 1.09(1) | 1.02(1) | 1.07(1) | 1.03(1) | 1.08(1) | 1.04(1) | 1.14(1) | 1.03(1) | 1.05(1) | 1.06(1) |
| Cys(1/2) | 4.53(6) | 5.57(6) | 4.31(6) | 5.01(6) | 4.05(6) | 5.17(6) | 4.81(6) | 5.16(6) | 5.31(6) | 4.97(6) |
| Val | 3.72(4) | 3.61(4) | 3.37(4) | 3.42(4) | 3.41(4) | 3.43(4) | 4.80(5) | 3.59(4) | 3.68(4) | 4.49(5) |
| Ile | 1.72(2) | 1.56(2) | 1.42(2) | 1.48(2) | 1.44(2) | 1.48(2) | 1.67(2) | 1.59(2) | 1.62(2) | 1.72(2) |
| Leu | 6.01(6) | 6.09(6) | 5.95(6) | 6.02(6) | 6.01(6) | 5.98(6) | 5.96(6) | 5.99(6) | 6.15(6) | 6.06(6) |
| Tyr | 3.55(4) | 3.93(4) | 3.60(4) | 3.72(4) | 3.78(4) | 4.67(5) | 3.77(4) | 3.75(4) | 3.85(4) | 3.84(4) |
| Phe | 3.59(4) | 3.13(3) | 2.76(3) | 2.85(3) | 2.74(3) | 2.83(3) | 3.28(3) | 2.87(3) | 3.06(3) | 2.97(3) |
| His | 2.14(2) | 2.10(2) | 2.55(2) | 2.32(2) | 2.82(2) | 2.08(2) | 2.25(2) | 2.02(2) | 1.12(1) | 1.09(1) |
| Lys | | | | | | | | | | |
| Arg | 0.87(1) | 1.02(1) | 0.85(1) | 0.92(1) | 1.05(1) | 0.86(1) | 1.02(1) | 0.87(1) | 1.03(1) | 0.98(1) |
| Aba | | | | | | | | | | |
| Cya | | | | | | | | | | |
| Nle | | | | | | | | | | |
| Orn | | | | | | | | | | |
| Nva | | | | | | | | 0.98(1) | | |
| Met | | | | | | | | | | |
| Trp | | | | | 0.89(1) | | | | | |

TABLE II-continued

Amino Acid Analysis on Human Insulin Analogs[1,2]

| | Example No. | |
|---|---|---|
| | 31 | 32 |
| Amino Acid Residue | | |
| Asp | 4.00(4) | 4.00(4) |
| Thr | 2.75(3) | 2.81(3) |
| Ser | 2.57(3) | 2.63(3) |
| Glu | 8.07(8) | 8.02(8) |
| Pro | 1.02(1) | 1.02(1) |
| Gly | 4.07(4) | 4.oo(4) |
| Ala | 1.06(1) | 1.03(1) |
| Cys(1/2) | 5.23(6) | 5.39(6) |
| Val | 3.73(4) | 3.65(4) |
| Ile | 1.76(2) | 1.76(2) |
| Leu | 6.07(6) | 6.11(6) |
| Tyr | 3.73(4) | 3.87(4) |
| Phe | 2.92(3) | 3.02(3) |
| His | 1.25(1) | 1.05(1) |
| Lys | | |
| Arg | 1.03(1) | 1.02(1) |
| Aba | | |
| Cya | | |
| Nle | | |
| Orn | | |
| Nva | | |
| Met | | |
| Trp | | |

[1]Molar unity based on aspartic acid.
[2]Number in parenthesis is theoretical amino acid content.
[3]Half-cystine plus aminobutyric acid totaled 6.49.

The physiological effects of the insulin analogs of the present invention were shown in the following in vivo assay system.

Normal male Sprague Dawley rats from the Charles River Laboratories (Portage, Mich.) were used as test animals. They were obtained at a weight range of 160–180 gms and maintained for one week in animal rooms at 75° F. with a controlled light cycle (lights on 7:00 a.m.–7:00 p.m., lights off 7:00 p.m.–7:00 a.m.) The animals were fed Purina rat chow 5001 ad libitum. Rats used for each assay were fasted for 16 hours before being used. They weighed about 200 gms when first used. On reaching a fasted weight of about 275 gm (over a period of three weeks), the animals were no longer used. One group of ten male rats was used each day for each compound tested (i.e., biosynthetic human insulin, porcine insulin and human insulin analog). Each group was used only once during the week. The ten rats were divided into two groups of five rats each. One group served as control and was given vehicle alone subcutaneously. The other group of five rats was given the compound to be tested. The proteins were dissolved in 0.05N HCl (pH 1.6) to provide a stock solution of 100 μgm per ml. From this, a number of dilutions were made in normal saline which was injected subcutaneously into the rats. A 100 μl sample of blood was taken from the tail vein of each rat at zero time and 30 minutes, 1 hour, 2 hours, 3 hours and 4 hours after administration. Glucose was determined colorimetrically by a glucose oxidase method (Sigma Chemical Co.). The percent change in blood glucose from the zero time value was calculated for each rat and the final results were expressed as the mean percent change±SEM in the experimental group corrected for the mean change in the control group for that day.

A dose-response curve was drawn from tests with 4 to 7 different concentrations of the compound tested using the maximal response at a given time (usually one or two hours after administration of the protein). From this curve an $ED_{50}$ value was determined as that subcutaneous dose (μg/kg) of the protein which gave half the maximal hypoglycemic response. The results are shown in Table III following.

TABLE III[a]

| Compound | $ED_{50}$[b] | Biological Activity[c] |
|---|---|---|
| Human Insulin (HI)[d] | 7.95 | 100 |
| Porcine Insulin | 7.70 | 103 |
| Lys(B28),Pro(B29)HI | 6.8 | 117 |
| Ala(B28),Pro(B29)HI | 15.0 | 53 |
| Asp(B28),Pro(B29)HI | 10.2 | 78 |
| Asp(B10),Lys(B28),Pro(B29)HI | 10.7 | 74 |
| Gln(B28),Pro(B29)HI | 6.6 | 120 |
| Gly(B28),Pro(B29)HI | 10.5 | 76 |
| Met(B28),Pro(B29)HI | 14.6 | 54 |
| Nle(B28),Pro(B29)HI | 7.0 | 114 |
| Orn(B28),Pro(B29)HI | 12.7 | 63 |
| Pro(B29)HI | 8.7 | 91 |
| Phe(B28),Pro(B29)HI | 9.7 | 82 |
| Val(B28),Pro(B29)HI | 8.7 | 91 |

[a]All values shown refer to blood samples taken one hour after administration of the compound shown
[b]Expressed in μg/kg, subcutaneous
[c]Relative to human insulin
[d]Biosynthetic human insulin The preceding table represents the results of an initial series of tests. More tests were then run on human insulin, Lys(B28) Pro(B29)HI and several additional insulin analogs. The following Table III-A represents the combined results of all tests.

TABLE III-A[a]

| Compound | $ED_{50}$[b] | Relative Hypoglycemic Activity (%)[c] |
|---|---|---|
| Human Insulin (HI)[d] | 7.75 | 100 |
| Porcine Insulin | 7.70 | 101 |
| Lys(B28),Pro(B29)HI | 7.18 | 108 |
| Aba(B28),Pro(B29)HI | 15.5 | 50 |
| Ala(B28),Pro(B29)HI | 15.0 | 52 |
| Arg(B28),Pro(B29)HI | 9.0 | 86 |
| Asn(B28),Pro(B29)HI | 10.4 | 75 |
| Asp(B28),Pro(B29)HI | 10.2 | 76 |
| Asp(B10),Asp(B28),Pro(B29)HI | 14.9 | 52 |
| Asp(B10),Gln(B28),Pro(B29)HI | 15.2 | 51 |
| Asp(B10),Glu(B28),Pro(B29)HI | 17.5 | 44 |
| Asp(B10),Lys(B28),Pro(B29)HI | 10.7 | 72 |
| Asp(B10),Val(B28),Pro(B29)HI | 13.5 | 57 |
| Cya(B28),Pro(B29)HI | 6.4 | 121 |
| Gln(B28),Pro(B29)HI | 6.6 | 117 |
| Glu(B28),Pro(B29)HI | 6.8 | 114 |
| Gly(B28),Pro(B29)HI | 10.5 | 74 |
| His(B28),Pro(B29)HI | 13.0 | 60 |
| Ile(B28),Pro(B29)HI | 9.6 | 81 |
| Leu(B28),Pro(B29)HI | 8.4 | 92 |
| Met(B28),Pro(B29)HI | 14.6 | 53 |
| Nle(B28),Pro(B29)HI | 7.0 | 111 |
| Nva(B28),Pro(B29)HI | 14.6 | 53 |
| Orn(B28),Pro(B29)HI | 12.7 | 61 |
| Phe(B28),Pro(B29)HI | 9.7 | 80 |
| Pro(B29)HI | 8.7 | 89 |
| Ser(B28),Pro(B29)HI | 10.3 | 75 |
| Thr(B28),Pro(B29)HI | 8.2 | 95 |
| Trp(B28),Pro(B29)HI | 7.5 | 103 |
| Tyr(B28),Pro(B29)HI | 6.2 | 125 |
| Val(B28),Pro(B29)HI | 8.7 | 89 |

[a]All values shown refer to blood samples taken one hour after administration of the compound shown except for Aba(B28),Pro(B29)HI,Asp(B10),Asp(B28),Pro(B29)HI, and His(B28),Pro(B29)HI, which were taken after 2 hours.
[b]Expressed in µg/kg, subcutaneous
[c]Relative to human insulin
[d]Biosynthetic human insulin As noted previously, the insulin analogs of the present invention have a reduced propensity to dimerize or otherwise self-associate to higher molecular weight forms. Thus, upon administration of one or more of said analogs, a rapid onset of activity is achieved. The insulin analogs of the present invention are effective in treating hyperglycemia by administering to a patient in need thereof an effective amount of an insulin analog of formula I. As used herein the term "effective amount" refers to that amount of one or more insulin analogs of the present invention needed to lower or maintain blood sugar levels either therapeutically or prophylactically. This amount typically may range from about 10 units up to about 60 units or more per day (or about 0.3 to about 2 mg assuming approximately 29 units per mg). However, it is to be understood that the amount of the insulin analog(s) actually administered will be determined by a physician in light of the relevant circumstances including the condition being treated (i.e., the cause of the hyperglycemia) the particular analog to be administered, the chosen parenteral route of administration, the age, weight and response of the individual patient and the severity of the patient's symptoms. Therefore, the above dosage ranges are not intended to limit the scope of the invention in any manner.

The insulin analogs of the invention are administered to a patient in need thereof (i.e., a patient suffering from hyperglycemia) by means of pharmaceutical compositions containing an effective amount of at least one insulin analog of formula I in combination with one or more pharmaceutically acceptable excipients or carriers. For these purposes, the pharmaceutical compositions may typically be formulated so as to contain about 100 units per ml or similar concentrations containing an effective amount of the insulin analog(s). These compositions are typically, though not necessarily, parenteral in nature and may be prepared by any of a variety of techniques using conventional excipients or carriers for parenteral products which are well known in the art. See, for example, *Remington's Pharmaceutical Sciences*, 17th Edition, Mack Publishing Company, Easton, PA, USA (1985) which is incorporated herein by reference. For example, dosage forms for parenteral administration may be prepared by suspending or dissolving the desired amount of at least one insulin analog of formula I in a non-toxic liquid vehicle suitable for injection such as an aqueous medium and sterilizing the suspension or solution. Alternatively, a measured amount of the compound may be placed in a vial and the vial and its contents sterilized and sealed. An accompanying vial or vehicle can be provided for purposes of mixing prior to administration. Pharmaceutical compositions adapted for parenteral administration employ diluents, excipients and carriers such as water and water-miscible organic solvents such as glycerin, sesame oil, groundnut oil, aqueous propylene glycol, N,N'-dimethylformamide and the like. Examples of such pharmaceutical compositions include sterile, isotonic, aqueous saline solutions of the insulin analogs of formula I which can be buffered with a pharmaceutically acceptable buffer and which are pyrogen free. Additionally, the parenteral pharmaceutical formulation may contain preservatives such as phenol or meta-cresol. Agents to adjust pH of the final product such as sodium hydroxide or hydrochloric acid may also be used.

The insulin analogs of the present invention may also be formulated into pharmaceutical compositions suitable for intranasal administration. Such compositions are disclosed in detail in European Patent Application 0200383 A3 which is incorporated herein by reference. Briefly, such compositions are formulated with one or more pharmaceutically acceptable diluents, a pharmaceutically acceptable amount of an alkali metal salt, the ammonium salt, or the free acid of a substantially zinc-free insulin, and optionally, an absorption enhancing amount of at least one absorption enhancing agent selected from the group consisting of (1) oleic acid or an ester or salt thereof, (2) a liquid form sorbitan fatty acid ester, (3) a liquid form polyoxyethylene derivative of a sorbitan fatty acid ester, and (4) a liquid form hydroxypolyoxyethylene-polyoxypropylene-polyoxyethylene copolymer.

To demonstrate the efficacy of intranasal administration of the insulin analog Lys(B28), Pro(B29) human insulin versus human sodium insulin the following study was conducted. Male beagle dogs weighing 10 to 12 kg were maintained in excellent physical condition prior to and during the course of the study. The dogs were fasted for 16 hours but had access to water to ensure against unexpected fluctuations in insulin levels. During the entire course of the study the dogs were anesthetized with sodium pentobarbitol and their body temperature maintained with heating pads to minimize glucose fluctuation. The insulin test samples (i.e., Lys(B28), Pro(B29) human insulin and human sodium insulin) were dissolved in distilled water and the pH of the solution was adjusted to 7.5 with sodium hydroxide. The final insulin concentration was 70 units per ml. An insulin dose of 0.8 units per kg of Lys(B28), Pro(B29) human insulin was administered to each of eight dogs and similarly, a dose of 0.8 units per kg of human sodium insulin was administered to each of four dogs. All doses were administered to the nasal cavity by delivering one spray per nostril with a metered-dose nebulizer and a modified nasal applicator. Blood samples were drawn from the jugular vein at 30, 15 and 0 minutes before administration and at 10, 20, 30, 45, 60, 90, 120, 180 and 240 minutes after administration for the measurement of blood glucose reduction. The results of this study are shown in Table IV.

TABLE IV[a]

| Time (min) | Lys(B28),Pro(B29)Human Insulin (% of Initial) | Human Sodium Insulin (% of Initial) |
|---|---|---|
| −30 | 95.4 ± 2.5 | 101.6 ± 2.4 |
| −15 | 98.2 ± 2.8 | 102.4 ± 2.9 |
| 0 | 100 | 100 |
| 10 | 95.4 ± 2.1 | 100.8 ± 1.9 |
| 20 | 83.5 ± 3.3 | 96.0 ± 2.1 |
| 30 | 72.2 ± 4.5 | 91.6 ± 2.8 |
| 45 | 61.6 ± 6.9 | 89.1 ± 2.3 |
| 60 | 60.0 ± 6.0 | 93.6 ± 4.5 |
| 90 | 71.6 ± 4.6 | 92.2 ± 1.6 |
| 120 | 76.1 ± 3.7 | 91.3 ± 2.8 |
| 180 | 91.2 ± 1.8 | 93.8 ± 1.8 |
| 240 | 85.4 ± 2.7 | 90.7 ± 2.8 |

[a]Blood Glucose levels: mean ± S.E.M.

Utilizing the protocol described above, a comparison of the blood glucose reduction profile of Lys(B28), Pro(B29) human insulin via intranasal administration was compared to both intravenous and subcutaneous administration of the analog as follows. For intravenous administration, the insulin solution containing the Lys(B28), Pro(B29) human insulin analog was administered by bolus injection (0.1 units per kg) into the saphenous vein of each of four dogs. Blood samples were drawn at 30, 15 and 0 minutes before administration and at 5, 10, 15, 20, 30, 45, 60, 90, 120, 180 and 240 minutes after administration. For subcutaneous administration, the insulin solution containing the Lys(B28), Pro(B29) human insulin analog was administered beneath the epidermis (0.2 units per kg) of the outer side of the flank of each of six dogs. Blood samples were drawn at the same protocol as described after nasal administration as described above. The results of this comparative study are shown in Table IV.

TABLE V[a]

| Time (min) | I.V. (% of initial) | S.C. (% of initial) | Nasal (% of initial) |
|---|---|---|---|
| −30 | 96.6 ± 6.5 | 95.6 ± 2.1 | 95.4 ± 2.5 |
| −15 | 101.3 ± 1.5 | 98.7 ± 2.7 | 98.2 ± 2.8 |
| 0 | 100 | 100 | 100 |
| 5 | 99.9 ± 2.5 | — | — |
| 10 | 84.8 ± 4.0 | 99.2 ± 4.8 | 95.4 ± 2.1 |
| 15 | 68.1 ± 2.7 | — | — |
| 20 | 54.5 ± 3.3 | 91.9 ± 2.4 | 83.5 ± 3.3 |
| 30 | 43.3 ± 2.8 | 81.6 ± 3.0 | 72.2 ± 4.5 |
| 45 | — | 55.8 ± 3.5 | 61.6 ± 6.9 |
| 60 | 55.3 ± 3.1 | 35.3 ± 3.1 | 60.6 ± 6.0 |
| 90 | 77.2 ± 6.4 | 39.5 ± 3.4 | 71.6 ± 4.6 |
| 120 | 85.2 ± 4.7 | 36.1 ± 2.6 | 76.1 ± 3.7 |
| 180 | 97.1 ± 6.4 | 64.5 ± 7.0 | 91.2 ± 1.8 |
| 240 | 100.0 ± 9.6 | 81.3 ± 2.4 | 85.4 ± 2.7 |

[a]Blood glucose levels: mean ± S.E.M.

We claim:

1. An insulin analog of the formula

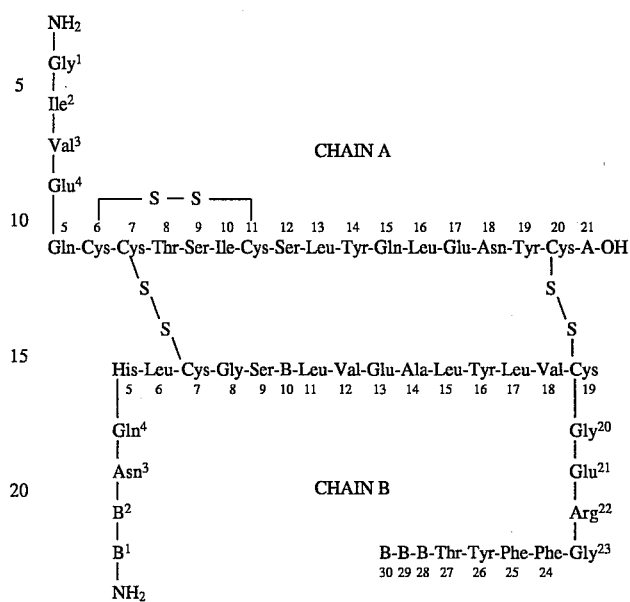

or a pharmaceutically acceptable salt thereof, wherein $A_{21}$ is Asn, or Ala;

$B_1$ is Phe, or is absent;

$B_2$ is Val, or is absent;

$B_{10}$ is His, or Asp;

$B_{28}$ is any amino acid;

$B_{29}$ is L-Pro, D-Pro, L-hydroxyproline, D-hydroxyproline;

and, $B_{30}$ is Thr, Ala, or is absent.

2. The insulin analog of claim 1 wherein $B_{28}$ is Asp, Val, Leu, Ile, Pro, Arg, His, Lys, Phe, Ala, Gly, norisoleucine, citrulline, or ornithine.

3. The insulin analog of claim 1 wherein $B_{28}$ is Lys.

4. The insulin analog of claim 1 wherein $A_{21}$ is Ala.

5. The insulin analog of claim 1 wherein $B_1$ is absent.

6. The insulin analog of claim 5 wherein $B_{10}$ is Asp.

7. The insulin analog of claim 5 wherein $B_2$ is absent.

8. The insulin analog of claim 6 wherein $B_2$ is absent.

9. The insulin analog of claim 1 wherein $B_{30}$ is absent.

10. The insulin analog of claim 1 wherein $B_{30}$ is Ala.

11. An insulin analog of the formula

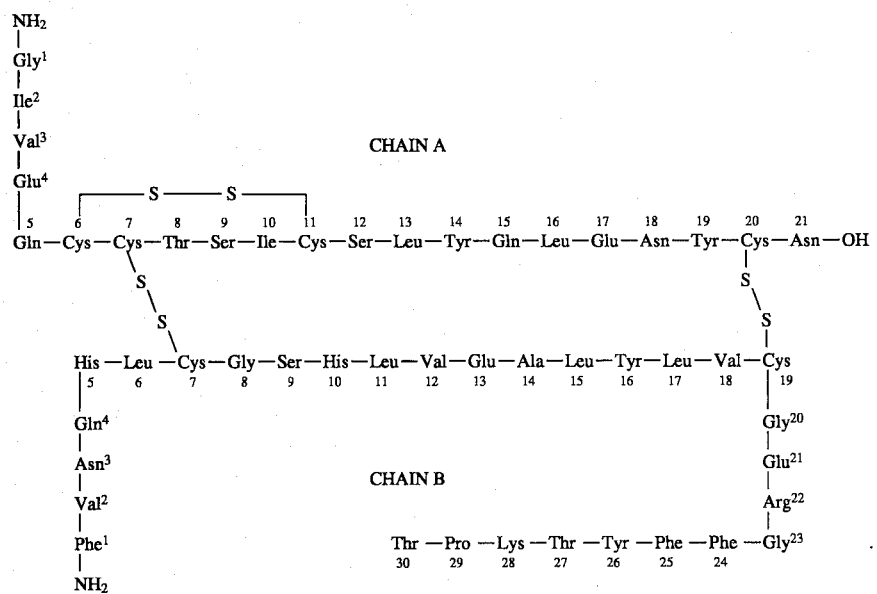

12. The insulin analog of claim 1 wherein $A_{21}$ is Ala, $B_1$ is Phe, $B_2$ is Val, $B_{10}$ is His, $B_{28}$ is Lys, $B_{29}$ is Pro, and $B_{30}$ is Thr.

13. The insulin analog of claim 1 wherein $A_{21}$ is Asn, $B_1$ is absent, $B_2$ is Val, $B_{10}$ is His, $B_{28}$ is Lys, $B_{29}$ is Pro, and $B_{30}$ is Thr.

14. The insulin analog of claim 1 wherein $A_{21}$ is Asn, $B_1$ is absent, $B_2$ is Val, $B_{10}$ is Asp, $B_{28}$ is Lys, $B_{29}$ is Pro, and $B_{30}$ is Thr.

15. The insulin analog of claim 1 wherein $A_{21}$ is Asn, $B_1$ is absent, $B_2$ is absent, $B_{10}$ is His, $B_{28}$ is Lys, $B_{29}$ is Pro, and $B_{30}$ is Thr.

16. The insulin analog of claim 1 wherein $A_{21}$ is Asn, $B_1$ is absent, $B_2$ is absent, $B_{10}$ is Asp, $B_{28}$ is Lys, B29 is Pro, and $B_{30}$ is Thr.

17. The insulin analog of claim 1 wherein $A_{21}$ is Asn, $B_1$ is Phe, $B_2$ is Val, $B_{10}$ is His, $B_{28}$ is Lys, $B_{29}$ is Pro, and $B_{30}$ is absent.

18. The insulin analog of claim 1 wherein $A_{21}$ is Asn, $B_1$ is Phe, $B_2$ is Val, $B_{10}$ is His, $B_{28}$ is Lys, $B_{29}$ is Pro, and $B_{30}$ is Ala.

19. The insulin analog of claim 1 wherein $A_{21}$ is Asn, $B_1$ is Phe, $B_2$ is Val, $B_{10}$ is His, $B_{28}$ is Pro, $B_{30}$ is Thr, and $B_{29}$ is selected from the group consisting of L-(N-methyllysine), D-lysine, L-(N-methylarginine), and D-arginine.

20. The insulin analog of claim 1 wherein $A_{21}$ is Asn, $B_1$ is Phe, $B_2$ is Val, $B_{10}$ is His, $B_{28}$ is Pro, $B_{30}$ is Thr, and $B_{29}$ is selected from the group consisting of L-(N-methyllysine), and D-lysine.

21. The insulin analog of claim 1 wherein $A_{21}$ is Ala, $B_1$ is Phe, $B_2$ is Val, $B_{10}$ is His, $B_{28}$ is Pro, $B_{30}$ is Thr, and $B_{29}$ is selected from the group consisting of L-(N-methyllysine), D-lysine, L-(N-methylarginine), and D-arginine.

22. The insulin analog of claim 1 wherein $A_{21}$ is Asn, $B_1$ is absent, $B_2$ is Val, $B_{10}$ is His, $B_{28}$ is Pro, $B_{30}$ is Thr, and $B_{29}$ is selected from the group consisting of L-(N-methyllysine), D-lysine, L-(N-methylarginine), and D-arginine.

23. The insulin analog of claim 1 wherein $A_{21}$ is Asn, $B_1$ is absent, $B_2$ is Val, $B_{10}$ is Asp, $B_{28}$ is Pro, $B_{30}$ is Thr, and $B_{29}$ is selected from the group consisting of L-(N-methyllysine), D-lysine, L-(N-methylarginine), and D-arginine.

24. The insulin analog of claim 1 wherein $A_{21}$ is Asn, $B_1$ is absent, $B_2$ is absent, $B_{10}$ is His, $B_{28}$ is Pro, $B_{30}$ is Thr, and $B_{29}$ is selected from the group consisting of L-(N-methyllysine), D-lysine, L-(N-methylarginine), and D-arginine.

25. The insulin analog of claim 1 wherein $A_{21}$ is Asn, $B_1$ is absent, $B_2$ is absent, $B_{10}$ is Asp, $B_{28}$ is Pro, $B_{30}$ is Thr, and $B_{29}$ is selected from the group consisting of L-(N-methyllysine), D-lysine, L-(N-methylarginine), and D-arginine.

26. The insulin analog of claim 1 wherein $A_{21}$ is Asn, $B_1$ is Phe, $B_2$ is Val, $B_{10}$ is His, $B_{28}$ is Pro, $B_{30}$ is absent, and $B_{29}$ is selected from the group consisting of L-(N-methyllysine), D-lysine, L-(N-methylarginine), and D-arginine.

27. The insulin analog of claim 1 wherein $A_{21}$ is Asn, $B_1$ is Phe, $B_2$ is Val, $B_{10}$ is His, $B_{28}$ is Pro, $B_{30}$ is Ala, and $B_{29}$ is selected from the group consisting of L-(N-methyllysine), D-lysine, L-(N-methylarginine), and D-arginine.

28. A method of treating hyperglycemia which comprises administering, to a patient in need thereof, an effective amount of an insulin analog according to claim 1.

29. A method of treating hyperglycemia which comprises administering, to a patient in need thereof, an effective amount of an insulin analog according to claim 2.

30. A method of treating hyperglycemia which comprises administering, to a patient in need thereof, an effective amount of an insulin analog according to claim 3.

31. A method of treating hyperglycemia which comprises administering, to a patient in need thereof, an effective amount of an insulin analog according to claim 4.

32. A method of treating hyperglycemia which comprises administering, to a patient in need thereof, an effective amount of an insulin analog according to claim 5.

33. A method of treating hyperglycemia which comprises administering, to a patient in need thereof, an effective amount of an insulin analog according to claim 6.

34. A method of treating hyperglycemia which comprises administering, to a patient in need thereof, an effective amount of an insulin analog according to claim 7.

35. A method of treating hyperglycemia which comprises administering, to a patient in need thereof, an effective amount of an insulin analog according to claim 8.

36. A method of treating hyperglycemia which comprises administering, to a patient in need thereof, an effective amount of an insulin analog according to claim 9.

37. A method of treating hyperglycemia which comprises administering, to a patient in need thereof, an effective amount of an insulin analog according to claim 10.

38. A method of treating hyperglycemia which comprises administering, to a patient in need thereof, an effective amount of an insulin analog of the formula

```
NH₂
|
Gly¹
|
Ile²
|
Val³
|
Glu⁴
|                                CHAIN A
|    ┌──S────S──┐
|5   6   7   8   9  10  11  12  13  14  15  16  17  18  19  20  21
Gln─Cys─Cys─Thr─Ser─Ile─Cys─Ser─Leu─Tyr─Gln─Leu─Glu─Asn─Tyr─Cys─Asn─OH
         \                                              |
          S                                             S
           \                                             \
            S                                             S
             \                                             |
His─Leu─Cys─Gly─Ser─His─Leu─Val─Glu─Ala─Leu─Tyr─Leu─Val─Cys
|5   6   7   8   9  10  11  12  13  14  15  16  17  18  |19
|                                                        Gly²⁰
Gln⁴                                                     |
|                                                        Glu²¹
Asn³              CHAIN B                                |
|                                                        Arg²²
Val²                                                     |
|                 Thr─Pro─Lys─Thr─Tyr─Phe─Phe─Gly²³
Phe¹              30   29   28   27   26   25   24
|
NH₂
```

39. A method of treating hyperglycemia which comprises administering, to a patient in need thereof, an effective amount of an insulin analog according to claim 12.

40. A method of treating hyperglycemia which comprises administering, to a patient in need thereof, an effective amount of an insulin analog according to claim 13.

41. A method of treating hyperglycemia which comprises administering, to a patient in need thereof, an effective amount of an insulin analog according to claim 14.

42. A method of treating hyperglycemia which comprises administering, to a patient in need thereof, an effective amount of an insulin analog according to claim 15.

43. A method of treating hyperglycemia which comprises administering, to a patient in need thereof, an effective amount of an insulin analog according to claim 16.

44. A method of treating hyperglycemia which comprises administering, to a patient in need thereof, an effective amount of an insulin analog according to claim 17.

45. A method of treating hyperglycemia which comprises administering, to a patient in need thereof, an effective amount of an insulin analog according to claim 18.

46. A method of treating hyperglycemia which comprises administering, to a patient in need thereof, an effective amount of an insulin analog according to claim 19.

47. A method of treating hyperglycemia which comprises administering, to a patient in need thereof, an effective amount of an insulin analog according to claim 20.

48. A method of treating hyperglycemia which comprises administering, to a patient in need thereof, an effective amount of an insulin analog according to claim 21.

49. A method of treating hyperglycemia which comprises administering, to a patient in need thereof, an effective amount of an insulin analog according to claim 22.

50. A method of treating hyperglycemia which comprises administering, to a patient in need thereof, an effective amount of an insulin analog according to claim 23.

51. A method of treating hyperglycemia which comprises administering, to a patient in need thereof, an effective amount of an insulin analog according to claim 24.

52. A method of treating hyperglycemia which comprises administering, to a patient in need thereof, an effective amount of an insulin analog according to claim 25.

53. A method of treating hyperglycemia which comprises administering, to a patient in need thereof, an effective amount of an, insulin analog according to claim 26.

54. A method of treating hyperglycemia which comprises administering, to a patient in need thereof, an effective amount of an insulin analog according to claim 27.

55. A pharmaceutical composition which comprises an insulin analog according to claim 1 in combination with a pharmaceutically acceptable carrier, diluent, or excipient.

56. A pharmaceutical composition which comprises an insulin analog according to claim 2 in combination with a pharmaceutically acceptable carrier, diluent, or excipient.

57. A pharmaceutical composition which comprises an insulin analog according to claim 3 in combination with a pharmaceutically acceptable carrier, diluent, or excipient.

58. A pharmaceutical composition which comprises an insulin analog according to claim 4 in combination with a pharmaceutically acceptable carrier, diluent, or excipient.

59. A pharmaceutical composition which comprises an insulin analog according to claim 5 in combination with a pharmaceutically acceptable carrier, diluent, or excipient.

60. A pharmaceutical composition which comprises an insulin analog according to claim 6 in combination with a pharmaceutically acceptable carrier, diluent, or excipient.

61. A pharmaceutical composition which comprises an insulin analog according to claim 7 in combination with a pharmaceutically acceptable carrier, diluent, or excipient.

62. A pharmaceutical composition which comprises an insulin analog according to claim 8 in combination with a pharmaceutically acceptable carrier, diluent, or excipient.

63. A pharmaceutical composition which comprises an insulin analog according to claim 9 in combination with a pharmaceutically acceptable carrier, diluent, or excipient.

64. A pharmaceutical composition which comprises an insulin analog according to claim 10 in combination with a pharmaceutically acceptable carrier, diluent, or excipient.

65. A pharmaceutical composition which comprises an insulin analog of the formula

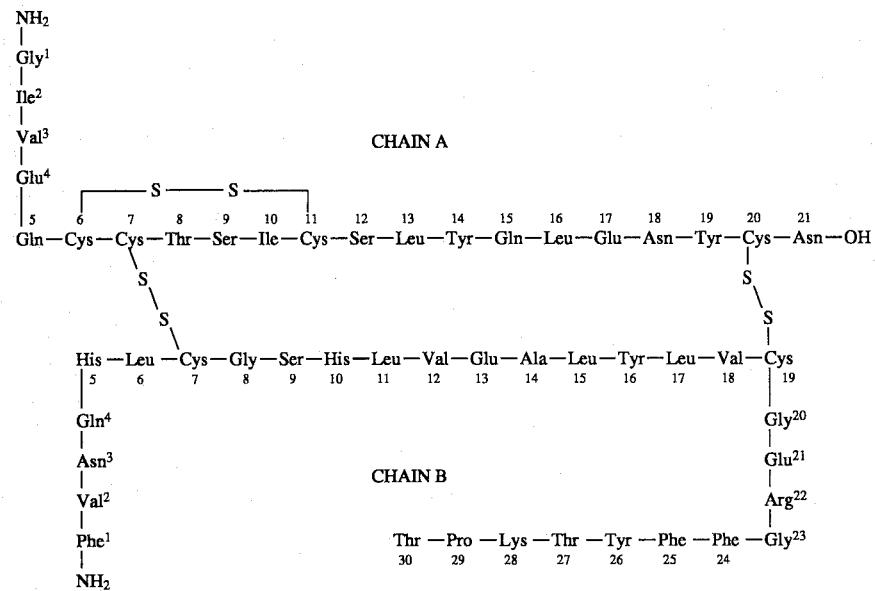

in combination with a pharmaceutically acceptable carrier, diluent, or excipient.

66. A pharmaceutical composition which comprises an insulin analog according to claim 12 in combination with a pharmaceutically acceptable carrier, diluent, or excipient.

67. A pharmaceutical composition which comprises an insulin analog according to claim 13 in combination with a pharmaceutically acceptable carrier, diluent, or excipient.

68. A pharmaceutical composition which comprises an insulin analog according to claim 14 in combination with a pharmaceutically acceptable carrier, diluent, or excipient.

69. A pharmaceutical composition which comprises an insulin analog according to claim 15 in combination with a pharmaceutically acceptable carrier, diluent, or excipient.

70. A pharmaceutical composition which comprises an insulin analog according to claim 16 in combination with a pharmaceutically acceptable carrier, diluent, or excipient.

71. A pharmaceutical composition which comprises an insulin analog according to claim 17 in combination with a pharmaceutically acceptable carrier, diluent, or excipient.

72. A pharmaceutical composition which comprises an insulin analog according to claim 18 in combination with a pharmaceutically acceptable carrier, diluent, or excipient.

73. A pharmaceutical composition which comprises an insulin analog according to claim 19 in combination with a pharmaceutically acceptable carrier, diluent, or excipient.

74. A pharmaceutical composition which comprises an insulin analog according to claim 20 in combination with a pharmaceutically acceptable carrier, diluent, or excipient.

75. A pharmaceutical composition which comprises an insulin analog according to claim 21 in combination with a pharmaceutically acceptable carrier, diluent, or excipient.

76. A pharmaceutical composition which comprises an insulin analog according to claim 22 in combination with a pharmaceutically acceptable carrier, diluent, or excipient.

77. A pharmaceutical composition which comprises an insulin analog according to claim 23 in combination with a pharmaceutically acceptable carrier, diluent, or excipient.

78. A pharmaceutical composition which comprises an insulin analog according to claim 24 in combination with a pharmaceutically acceptable carrier, diluent, or excipient.

79. A pharmaceutical composition which comprises an insulin analog according to claim 25 in combination with a pharmaceutically acceptable carrier, diluent, or excipient.

80. A pharmaceutical composition which comprises an insulin analog according to claim 26 in combination with a pharmaceutically acceptable carrier, diluent, or excipient.

81. A pharmaceutical composition which comprises an insulin analog according to claim 27 in combination with a pharmaceutically acceptable carrier, diluent, or excipient.

* * * * *

UNITED STATES PATENT AND TRADEMARK OFFICE
CERTIFICATE OF CORRECTION

PATENT NO. : 5,514,646
DATED : May 7, 1996
INVENTOR(S) : Ronald E. Chance, et al It is certified that error appears in the above-indentified patent and that said Letters Patent is hereby corrected as shown below:

Col. 10, line 13, "rag" should be corrected to --mg--.

Col. 12, line 15, "705" should be corrected to --.705--.

Col. 24, line 34, "xhoI" should be corrected to --XhoI--.

Col. 33/34, second sequence, line begining GAG, "S" at the end of the next set of letters after GAG, last letter should be corrected to --C--.

Col. 35/36, third line of sequence, delete last two letters "VC" and insert --C--.

Col. 47/48, third table, under column 20, fourth value down "7.06(7)" should be corrected to --7.06--.

Col. 47/48, third table, under column 24, fourth value down "7.04(7)" should be corrected to -- 7.04--.

Col. 47/48, third table, under column 25, fifth value down "1,22(1)" should be corrected to --1.22(1)--.

Signed and Sealed this

Eleventh Day of March, 1997

Attest:

BRUCE LEHMAN

*Attesting Officer*     *Commissioner of Patents and Trademarks*